(12) United States Patent
Katz et al.

(10) Patent No.: US 8,895,287 B2
(45) Date of Patent: Nov. 25, 2014

(54) METABOLICALLY ENGINEERED CELLS FOR THE PRODUCTION OF RESVERATROL OR AN OLIGOMERIC OR GLYCOSIDICALLY-BOUND DERIVATIVE THEREOF

(75) Inventors: Michael Katz, Malmö (SE); Hans Peter Smits, Holte (DK); Jochen Förster, Copenhagen (DK); Jens Bredal Nielsen, Charlottenlund (DK)

(73) Assignee: Evolva SA, Reinach (CH)

( * ) Notice: Subject to any disclaimer, the term of this patent is extended or adjusted under 35 U.S.C. 154(b) by 1397 days.

(21) Appl. No.: 11/816,847

(22) PCT Filed: Feb. 21, 2006

(86) PCT No.: PCT/EP2006/060154
§ 371 (c)(1),
(2), (4) Date: May 27, 2008

(87) PCT Pub. No.: WO2006/089898
PCT Pub. Date: Aug. 31, 2006

(65) Prior Publication Data
US 2008/0286844 A1    Nov. 20, 2008

(30) Foreign Application Priority Data

Feb. 22, 2005    (GB) .................................. 0503657.9

(51) Int. Cl.

| | | |
|---|---|---|
| C12N 1/20 | (2006.01) | |
| C12N 1/00 | (2006.01) | |
| C12P 7/22 | (2006.01) | |
| C07H 21/04 | (2006.01) | |
| C12P 7/42 | (2006.01) | |
| C12N 9/02 | (2006.01) | |
| C12N 9/10 | (2006.01) | |
| C12N 9/88 | (2006.01) | |
| C12N 9/00 | (2006.01) | |
| C12N 15/52 | (2006.01) | |

(52) U.S. Cl.
CPC .................. *C12P 7/42* (2013.01); *C12N 9/0042* (2013.01); *C12N 9/0073* (2013.01); *C12N 9/1029* (2013.01); *C12N 9/88* (2013.01); *C12N 9/93* (2013.01); *C12N 15/52* (2013.01); *C12P 7/22* (2013.01)
USPC ................ 435/252.3; 435/252.33; 435/254.2; 435/252.21; 435/254.22; 435/254.23; 435/254.3; 435/156; 536/23.2

(58) Field of Classification Search
None
See application file for complete search history.

(56) References Cited

U.S. PATENT DOCUMENTS

| | | |
|---|---|---|
| 6,521,748 B2 | 2/2003 | Tang |
| 7,604,968 B2 | 10/2009 | Schmidt-Dannert et al. |
| 2001/0053847 A1 | 12/2001 | Tang |
| 2004/0023357 A1 | 2/2004 | Breineg |
| 2004/0059103 A1 | 3/2004 | Huang et al. |
| 2009/0035839 A1 | 2/2009 | Katz et al. |

FOREIGN PATENT DOCUMENTS

| | | |
|---|---|---|
| WO | 0210407 A1 | 2/2002 |
| WO | 2006125000 A2 | 11/2006 |
| ZA | 20048194 | 10/2004 |

OTHER PUBLICATIONS

Becker et al., "Metabolic engineering of *Saccharomyces cerevisiae* for the synthesis of the wine-related antioxidant resveratrol," FEMS Yeast Research 4:79-85, 2003.*
Whisstock et al. Quaterly Reviews of Biophysics, 2003, "Prediction of protein function from protein sequence and structure", 36(3): 307-340.*
Punt et al. Trends in Biotechnol 20(5):200-206, 2002.*
Ro, et al. "Functional Characterization and Subcellular Localization of Poplar (*Populus trichocarpa* x *Populus deltoides*) Cinnamate 4-Hydroxylase." Plant Physiol. 126, 2001. pp. 317-329.
Ro, et al. "Reconstitution of the entry point of plant phenylpropanoid metabolism in yeast (*Saccharomyces cerevisiae*): implications for control of metabolic flux into the phenylpropanoid pathway." J. Biol. Chem. 279, 2004. pp. 2600-2607.
Rosler, et al. "Maize phenylalanine ammonia-lyase has tyrosine ammonia-lyase activity." Plant Physiol. 113, 1997. pp. 175-179.
Samappito, et al. "Aromatic and pyrone polyketides synthesized by a stilbene synthase from Rheum tataricum." Phytochemistry 62, 2003. pp. 313-323.
Sambrook, et al. (1989). "Molecular Cloning." Lab. Manual, 2nd edition, 1989. Cold Spring Harbor, N.Y.
Schoppner, et al. "Purification and properties of a stilbene synthase from induced cell suspension cultures of peanut." J. Biol. Chem. 259, 1984. pp. 6806-6811.
Seshime, et al. "Genomic evidences for the existence of a phenylpropanoid metabolic pathway in *Aspergillus oryzae*." Biochem Biophys Res Commun. 337, 2005. pp. 747-751.

(Continued)

*Primary Examiner* — Iqbal H Chowdhury
(74) *Attorney, Agent, or Firm* — McDonnell Boehnen Hulbert & Berghoff LLP

(57) ABSTRACT

A recombinant micro-organism producing resveratrol by a pathway in which phenylalanine ammonia lyase (PAL) produces trans-cinnamic acid from phenylalanine, cinnamate 4-hydroxylase (C4H) produces 4-coumaric acid from said trans-cinnamic acid, 4-coumarate-CoA ligase (4CL) produces 4-coumaroyl CoA from said 4-coumaric acid, and resveratrol synthase (VST) produces said resveratrol from said 4-coumaroyl CoA, or in which L-phenylalanine- or tyrosine-ammonia lyase (PAL/TAL) produces 4-coumaric acid, 4-coumarate-CoA ligase (4CL) produces 4-coumaroyl CoA from said 4-coumaric acid, and resveratrol synthase (VST) produces said resveratrol from said 4-coumaroyl CoA. The micro-organism may be a yeast, fungus or bacterium including *Saccharomyces cerevisiae*, *E. coli*, *Lactococcus lactis*, *Aspergillus niger*, or *Aspergillus oryzae*.

23 Claims, 7 Drawing Sheets

(56) References Cited

OTHER PUBLICATIONS

Urban, et al. "Cloning, Yeast Expression, and Characterization of the Coupling of Two Distantly Related *Arabidopsis thaliana* NADPH-Cytochrome 450 Reductases with P450 CYP73A5." J. Biol. Chem. 272, 1997. pp. 19176-19186.

Watts, et al. "Exploring recombinant flavonoid biosynthesis in metabolically engineered *Escherichia coli*." Chembiochem 5, 2004. pp. 500-507.

Allina, et al. "4-coumarate: Coenzyme A ligase in hybrid poplar. Properties of enzymes, cDNA cloning, and analysis of recombinant clones." Plant Physiol. 116, 1998. pp. 743-754.

Aoyama, et al. "NADPH-cytochrome P-450 reductase of yeast microsomes." Arch. Biochem. Biophys. 185, 1978. pp. 362-369.

Becker, et al. "Metabolic engineering of *Saccharomyces cerevisiae* for the synthesis of the wine-related antioxidant resveratrol." FEMS Yeast Res. 4, 2003. pp. 79-85.

Blanquet, et al. "Recombinant *Saccharomyces cerevisiae* Expressing P450 in Artificial Digestive Systems: a Model for Biodetoxication in the Human Digestive Environment." Applied and Environmental Microbiology, 2003. pp. 2884-2892.

Celotti, et al. "Resveratrol content of some wines obtained from dried Valpolicella grapes: Recioto and Amarone." Journal of Chromatography A 730, 1996. pp. 47-52.

Cochrane, et al. "The *Arabidopsis* phenylalanine ammonia lyase gene family: kinetic characterization of the four PAL isoforms." Phytochemistry 65, 2004. pp. 1557-1564.

Couzin. "Aging Research's Family Feud." Science 303, 2004. pp. 1276-1279.

Ehlting, et al. "Three 4-coumarate:coenzyme A ligases in *Arabidopsis thaliana* represents two evolutionary divergent classes in angiosperms." The plant journal 19, 1999. pp. 9-20.

Filpula, et al. "Nucleotide sequence of gene for phenylalanine ammonia-lyase from *Rhodotorula rubra*." Nucleic Acids Res. 16, 1988. pp. 11381.

Gehm, et al. "Resveratrol, a polyphenolic compound found in grapes and wine, is an agonist for the estrogen receptor." Proc. Natl. Acad. Sci. USA 94, 1997. pp. 14138-14143.

Gems, et al. "An autonomously replicating plasmid transforms *Aspergillus nidulans* at high frequency." Gene 98, 1991. pp. 61-67.

Hain, et al. "Disease resistance results from foreign phytoalexin expression in a novel plant" Nature 361, 1993. pp. 153-156.

Hwang, et al. "Production of plan-specfc flavanones by *Eschercha coli* containing an artificial gene cluser. Appl. Environ." Microbiol. 69, 2003. pp. 2699-2706.

Huang. "Diet for cancer prevention." Food Sci. 24, 1997. pp. 713-727.

Hart. "Role of Phytostilbenes in Decay and Disease Resistance." Annu. Rev. Phytopathology 19, 1981. pp. 437-458.

Hart, et al. "Role of Stilbenes in Resistance of Wood to Decay." Phytopathology 69, 1979. pp. 1138-1143.

Hall. "In Vino Vitalis? Compounds ActiVate Life-Extending Genes." Science 301, 2003. pp. 1165.

Hamberger, et al. "The 4-coumarate:CoA ligase gene family in *Arabidopsis thaliana* comprises one rare, sinapate-activating and three commonly occurring isoenzymes." Proc. Natl. Acad. Sci. USA. 101, 2004. pp. 2209-2214.

Jang, et al. "Cancer Chemopreventive Activity of Resveratrol, a Natural Product Derived from Grapes." Science 275, 1997. pp. 218-220.

Jeandet, et al. "Effect of Enological Practices on the Resveratrol Isomer Content of Wine J. Agric." Food Chem. 43, 1995. pp. 316-319.

Jeandet, et al. "Occurence of a resveratrol•- D-glucoside in wine: Preliminary studies." Vitis 33, 1994. pp. 183-184.

Koopmann, et al. "Regulation and Functional Expression of Cinnamate 4-Hydroxylase from Parsley." Plant Physiol. 119, 1999. pp. 49-55.

Kopp. "Resveratrol, a phytooestrogen found in red wine. A possible explanation for the conundrum of the "French Paradox"?" Eur. J. Endocrinol. 138, 1998. pp. 619-620.

Kyndt, et al. "Characterization of a bacterial tyrosine ammonia lyase, a biosynthetic enzyme for the photoactive yellow protein." FEBS Lett. 512, 2002. pp. 240-244.

Lagrange, et al. "Cloning of the *Bacillus pumilus* beta-xylosidase gene (xynB) and its expression in *Saccharomyces cerevisiae*. Appl. Microbiol." Biotechnol. 47, 1997. pp. 262-266.

Lin, et al. "Sequence and analysis of chromosome 2 of the plant *Arabidopsis thaliana*." Nature 402, 1999. pp. 761-768.

Lobo. "Benefits and risks of estrogen replacement therapy." Am. J. Obstet. Gynecol. 173, 1995. pp. 982-989.

Martin, et al. "Engineering a mevalonate pathway in *Escherichia coli* for production of terpenoids." Nature biotechnology 21, 2003. pp. 796-802.

Mizutani, et al. "Isolation of a cDNA and a genomic clone encoding cinnamate 4-hydroxylase from *Arabidopsis* and its expression manner in planta" Plant Physiol. 113, 19973 pp. 755-763.

Ro, et al. "Functional Characterization and Subcellular Localization of Poplar (*Populus trichocarpa* x *Populus deltoides*) Cinnamate 4-Hydroxylase." Plant Physiol. 126. 2001. pp. 317-329.

Citation Reserved.

Schoppner, et al. "Purification and properties of a stilbene synthase from induced cell suspension cultures of peanut," J. Biol. Chem. 259, 1984. pp. 6806-6811.

Jeandet, et al., "Phytoalexins from the Vitaeae: Biosynthesis, Phytoalexin Gene Expression in Transgenic Plants, Antifungal Activity, and Metabolism", *J. Agric. Food Chem.*, vol. 50, pp. 2731-2741, 2002.

Austin, et al., "An Aldol Switch Discovered in Stilbene Synthases Mediated Cyclization Specificity of Type III Polyketide Synthases", *Chemistry & Biology*, vol. 11, pp. 1179-1194, Sep. 2004.

Baedeker, et al., "Autocatalytic Peptide Cyclization during Chain Folding of Histidine Ammonia-Lyase", *Structure*, vol. 10, pp. 61-67, Jan. 2002.

Baedeker, et al., "Structures of two histidine ammonia-lyase modifications and implications for the catalytic mechanism", *Eur. J. Biochem.*, vol 269, pp. 1790-1797, 2002.

Costa, et al., "Characterization in vitro and in vivo of the putative multigene 4-coumarate:CoA ligase network in *Arabidopsis*: syringyl lignin and sinapate/sinapyl alcohol derivative formation", *Phytochemistry*, vol. 66, pp. 2072-2091, 2005.

Hasemann, et al., "Structure and function of cytochromes P450:a comparative analysis of three crystal structures", *Structure*, vol. 2, pp. 41-62, Jan. 1995.

Hubbard, et al., "NADPH-Cytochrome P450 Oxidoreductase", *The Journal of Biological Chemistry*, vol. 276, No. 31, pp. 29163-29170, 2001.

Melchior, et al., "Grapevine stilbene synthase cDNA only slightly differing from chalcone synthase cDNA is expressed in *Escherichia coli* into a catalytically active enzyme", *FEBS*, vol. 268, No. 1, pp. 17-20, Jul. 1990.

Mizutani, et al., "Two Isoforms of NADPH:Cytochrome P450 Reductase in *Arabidopsis thaliana*", *Plant Physiol.*, vol. 116, pp. 357-367, 1998.

Nisimoto, Yukio, "Localization Cytochrome c-binding Domain on NADPH-Cytochrome P-450 Reductase", *The Journal of Biological Chemistry*, vol. 261, No. 30, pp. 14232-14239, 1986.

Porter, et al., "NADPH-Cytochrome P-450 Oxidoreductase: Flavin Mononucleotide and Flavin Adenine Dinucleotide Domains Evolved from Different Flavoproteins", *Biochemistry*, vol. 25, pp. 1682-1687, 1986.

Ritter, et al., "Structural Basis for the Entrance into the Phenylpropanoid Metabolism Catalyzed by Phenylalanine Ammonia-Lyase", *The Plant Cell*, vol. 16, pp. 3426-3436, Dec. 2004.

Röther, et al ., An active site homology model of phenylalanine ammonia-lyase from *Petroselinum crispum*, *Eur. J. Biochem.*, vol. 269, pp. 3065-3075, 2002.

Rupasinghe, et al., "Common active site architecture and binding strategy of four phenylpropanoid P450s from *Arabidopsis thaliana* as revealsed by molecular modeling", *Protein Engineering*, vol. 16, No. 10, pp. 721-731, 2003.

(56) References Cited

OTHER PUBLICATIONS

Schneider, et al., "The substrate specificity-determining amino acid cod of 4-coumarate:CoA ligase", *PNAS*, vol. 100, No. 14, pp. 8601-8606, Jul. 2003.

Schuster, et al., "Serine-202 is the putative precursor of the active site dehydroalanine of phenylalanine ammonia lyase", *FEBS Letters*, vol. 349, pp. 252-254, 1994.

Schwede, et al., "Crystal Structure of Histidine Ammonia-Lyase Revealing a Novel Polypeptide Modification as the Catalytic Electrophile", *Biochemistry*, vol. 38, pp. 5355-5361, 1999.

Stuible, et al., "Identification of the Substrate Specificity-conferring Amino Acid Residues of 4-Coumarate:Coenzyme A Ligase Allows the Rational Design of Mutant Enzymes with New Catalytic Properties", *The Journal of Biological Chemistry*, vol. 276, No. 29, pp. 26893-26897, 2001.

Suh, et al., "Identification of amino acid residues important in the cyclization reactions of chalcone and stilbene synthases", *Biochem. J.*, vol. 350, pp. 229-235, 2000.

Uhlmann, et al., "Molecular Cloning and Expression of 4-Coumarate:Coenzyme A Ligase, an Enzyme Involved in the Resistance Response of Soybean (*Glycine max* L.) against Pathogen Attack", *Plant Physiol.*, vol. 102, pp. 1147-1156, 1993.

Wang, et al., "Three-dimensional structure of NADPH-cytochrome P450 reductase: Prototype for FMN- and FAD-containing enzymes", *Proc. Natl. Acad. Sci. USA*, vol. 94, pp. 8411-8416, Aug. 1997.

Yabusaki, et al ., "Primary Structure of *Saccharomyces cerevisiae* NADPH-Cytochrome P450 Reductase Deduced from Nucleotide Sequence of Its Cloned Gene", *J. Biochem.*, vol. 103, pp. 1004-1010, 1988.

* cited by examiner

SEQUENCE LISTING

```
<160> NUMBER OF SEQ ID NOS: 38

<210> SEQ ID NO 1
<211> LENGTH: 2154
<212> TYPE: DNA
<213> ORGANISM: Arabidopsis thaliana

<400> SEQUENCE: 1
atggatcaaa tcgaagcaat gttgtgcggc ggaggagaga agacaaaagt ggcggttact      60
acgaagactt tggcagatcc attgaattgg ggtttagcag cggatcaaat gaaaggaagt     120
catttagatg aagtgaagaa gatggtcgaa gagtatcgta gaccagtcgt gaatcttggc     180
ggagaaacac tgacgatcgg acaagttgct gccatctcca ccgtaggagg cagcgttaag     240
gttgagttag cggagacttc aagagccggt gtgaaagcta gcagtgattg ggttatggag     300
agcatgaaca aggtactgac agttacggac gtcaccaccg gctttggtgc tacttctcac     360
cggagaacca aaaacggcac cgcattacaa acagaactca ttagattttt gaacgccgga     420
atattcggaa acacgaagga gacatgtcac acactgccgc aatccgccac aagagccgcc     480
atgctcgtca gagtcaacac tcttctccaa ggatactccg ggatccgatt cgagatcctc     540
gaagcgatta caagtctcct caaccacaac atctctccgt cactacctct ccgtggaacc     600
attaccgcct ccggcgatct cgttcctctc tcttacatcg ccggacttct caccggccgt     660
cctaattcca aagccaccgg tcccgacggt gaatcgctaa ccgcgaaaga agcttttgag     720
aaagccggaa tcagtactgg attcttcgat ttacaaccta aggaaggttt agctctcgtt     780
aatggcacgg cggttggatc tggaatggcg tcgatggttc tattcgaagc gaatgtccaa     840
```

```
gcggtgttag cggaggtttt atcagcgatc ttcgcggagg ttatgagcgg gaaacctgag    900
tttaccgatc atctgactca tcgtttaaaa catcatcccg acaaatcga agcggcggcg    960 ataatggagc acatactcga cggaagctca tacatgaaat tagctcaaaa ggttcacgag   1020
atggatccat tgcagaaacc aaaacaagat cgttacgctc ttcgtacatc tcctcaatgg   1080
ctaggtcctc aaattgaagt aatccgtcaa gctacgaaat cgatagagcg tgaaatcaac   1140
tccgttaacg ataatccgtt gatcgatgtt tcgaggaaca aggcgattca cggtggtaac   1200
ttccaaggaa caccaatcgg agtttctatg gataacacga gattggcgat gctgcgatt    1260 gggaagctaa tgtttgctca attctctgag cttgttaatg atttctacaa caatggactt   1320
ccttcgaatc taactgcttc gagtaatcca agtttggatt atggattcaa aggagcagag   1380
attgctatgg cttcttattg ttctgagctt caatacttgg ctaatccagt cacaagccat   1440
gttcaatcag ctgagcaaca taatcaagat gtgaactctc ttggtttgat ctcgtctcgt   1500
aaaacatctg aagctgtgga tattcttaag ctaatgtcaa caacgttcct tgtggggata   1560
tgtcaagctg ttgatttgag acatttggag gagaatctga caaaactgt gaagaacaca    1620 gtttctcaag ttgctaagaa agtgttaacc actggaatca acggtgagtt acatccgtca   1680
aggttttgcg agaaggactt gcttaaggtt gttgatcgtg agcaagtgtt cacgtatgtg   1740
gatgatcctt gtagcgctac gtacccgttg atgcagagac taagacaagt tattgttgat   1800
cacgctttgt ccaacggtga gactgagaag aatgcagtga cttcgatctt tcaaaagatt   1860
ggagcttttg aagaggagct taaggctgtg cttccaaagg aagttgaagc ggctagagcg   1920
gcttatggga atggaactgc gccgattcct aaccggatta aggaatgtag gtcgtatccg   1980
ttgtataggt tcgtgaggga agagcttgga acgaagttgt tgactggaga aaaggttgtg   2040
tctccgggag aggagtttga taaggtcttc actgctatgt gtgaaggtaa acttattgat   2100
ccgttgatgg attgtctcaa ggaatggaac ggagctccga ttccgatttg ctaa          2154
```

<210> SEQ ID NO 2
<211> LENGTH: 717
<212> TYPE: PRT
<213> ORGANISM: Arabidopsis thaliana

<400> SEQUENCE: 2

```
Met Asp Gln Ile Glu Ala Met Leu Cys Gly Gly Gly Glu Lys Thr Lys
1               5                  10                  15

Val Ala Val Thr Thr Lys Thr Leu Ala Asp Pro Leu Asn Trp Gly Leu
            20                  25                  30

Ala Ala Asp Gln Met Lys Gly Ser His Leu Asp Glu Val Lys Lys Met
        35                  40                  45

Val Glu Glu Tyr Arg Arg Pro Val Val Asn Leu Gly Gly Glu Thr Leu
    50                  55                  60

Thr Ile Gly Gln Val Ala Ala Ile Ser Thr Val Gly Gly Ser Val Lys
65                  70                  75                  80

Val Glu Leu Ala Glu Thr Ser Arg Ala Gly Val Lys Ala Ser Ser Asp
                85                  90                  95

Trp Val Met Glu Ser Met Asn Lys Gly Thr Asp Ser Tyr Gly Val Thr
            100                 105                 110

Thr Gly Phe Gly Ala Thr Ser His Arg Arg Thr Lys Asn Gly Thr Ala
        115                 120                 125

Leu Gln Thr Glu Leu Ile Arg Phe Leu Asn Ala Gly Ile Phe Gly Asn
    130                 135                 140
```

```
Thr Lys Glu Thr Cys His Thr Leu Pro Gln Ser Ala Thr Arg Ala Ala
145                 150                 155                 160

Met Leu Val Arg Val Asn Thr Leu Leu Gln Gly Tyr Ser Gly Ile Arg
            165                 170                 175

Phe Glu Ile Leu Glu Ala Ile Thr Ser Leu Leu Asn His Asn Ile Ser
                180                 185                 190

Pro Ser Leu Pro Leu Arg Gly Thr Ile Thr Ala Ser Gly Asp Leu Val
        195                 200                 205

Pro Leu Ser Tyr Ile Ala Gly Leu Leu Thr Gly Arg Pro Asn Ser Lys
        210                 215                 220

Ala Thr Gly Pro Asp Gly Glu Ser Leu Thr Ala Lys Glu Ala Phe Glu
225                 230                 235                 240

Lys Ala Gly Ile Ser Thr Gly Phe Phe Asp Leu Gln Pro Lys Glu Gly
                245                 250                 255

Leu Ala Leu Val Asn Gly Thr Ala Val Gly Ser Gly Met Ala Ser Met
            260                 265                 270

Val Leu Phe Glu Ala Asn Val Gln Ala Val Leu Ala Glu Val Leu Ser
        275                 280                 285

Ala Ile Phe Ala Glu Val Met Ser Gly Lys Pro Glu Phe Thr Asp His
290                 295                 300

Leu Thr His Arg Leu Lys His His Pro Gly Gln Ile Glu Ala Ala Ala
305                 310                 315                 320

Ile Met Glu His Ile Leu Asp Gly Ser Ser Tyr Met Lys Leu Ala Gln
                325                 330                 335

Lys Val His Glu Met Asp Pro Leu Gln Lys Pro Lys Asn Asp Arg Tyr
            340                 345                 350

Ala Leu Arg Thr Ser Pro Gln Trp Leu Gly Pro Gln Ile Glu Val Ile
        355                 360                 365

Arg Gln Ala Thr Lys Ser Ile Glu Arg Glu Ile Asn Ser Val Asn Asp
        370                 375                 380

Asn Pro Leu Ile Asp Val Ser Arg Asn Lys Ala Ile His Gly Gly Asn
385                 390                 395                 400

Phe Gln Gly Thr Pro Ile Gly Val Ser Met Asp Asn Thr Arg Leu Ala
                405                 410                 415

Ile Ala Ala Ile Gly Lys Leu Met Phe Ala Gln Phe Ser Glu Leu Val
            420                 425                 430

Asn Asp Phe Tyr Asn Asn Gly Leu Pro Ser Asn Leu Thr Ala Ser Ser
            435                 440                 445

Asn Pro Ser Leu Asp Tyr Gly Phe Lys Gly Ala Glu Ile Ala Met Ala
        450                 455                 460

Ser Tyr Cys Ser Glu Leu Gln Tyr Leu Ala Asn Pro Val Thr Ser His
465                 470                 475                 480

Val Gln Ser Ala Glu Gln His Asn Gln Asp Val Asn Ser Leu Gly Leu
            485                 490                 495

Ile Ser Ser Arg Lys Thr Ser Glu Ala Val Asp Ile Leu Lys Leu Met
        500                 505                 510

Ser Thr Thr Phe Leu Val Gly Ile Cys Gln Ala Val Asp Leu Arg His
            515                 520                 525

Leu Glu Glu Asn Leu Arg Gln Thr Val Lys Asn Thr Val Ser Gln Val
        530                 535                 540

Ala Lys Lys Val Leu Thr Thr Gly Ile Asn Gly Glu Leu His Pro Ser
545                 550                 555                 560

Arg Phe Cys Glu Lys Asp Leu Leu Lys Val Val Asp Arg Glu Gln Val
```

```
                  565                 570                 575
Phe Thr Tyr Val Asp Asp Pro Cys Ser Ala Thr Tyr Pro Leu Met Gln
                580                 585                 590

Arg Leu Arg Gln Val Ile Val Asp His Ala Leu Ser Asn Gly Glu Thr
                595                 600                 605

Glu Lys Asn Ala Val Thr Ser Ile Phe Gln Lys Ile Gly Ala Phe Glu
    610                 615                 620

Glu Glu Leu Lys Ala Val Leu Pro Lys Glu Val Glu Ala Ala Arg Ala
625                 630                 635                 640

Ala Tyr Gly Asn Gly Thr Ala Pro Ile Pro Asn Arg Ile Lys Glu Cys
                645                 650                 655

Arg Ser Tyr Pro Leu Tyr Arg Phe Val Arg Glu Leu Gly Thr Lys
                660                 665                 670

Leu Leu Thr Gly Glu Lys Val Val Ser Pro Gly Glu Glu Phe Asp Lys
                675                 680                 685

Val Phe Thr Ala Met Cys Glu Gly Lys Leu Ile Asp Pro Leu Met Asp
        690                 695                 700

Cys Leu Lys Glu Trp Asn Gly Ala Pro Ile Pro Ile Cys
705                 710                 715

<210> SEQ ID NO 3
<211> LENGTH: 1518
<212> TYPE: DNA
<213> ORGANISM: Arabidopsis thaliana

<400> SEQUENCE: 3
atggacctcc tcttgctgga gaagtcttta atcgccgtct tcgtggcggt gattctcgcc      60
acggtgattt caaagctccg cggcaagaaa ttgaagctac ctccaggtcc tataccaatt     120
ccgatcttcg gaaactggct tcaagtcgga gatgatctca accaccgtaa tctcgtcgat     180
tacgctaaga aattcggcga tctcttcctc ctccgtatgg gtcagcgaaa cctagtcgtc     240
gtctcctcac cggatctaac aaaggaagtg ctcctcactc aaggcgttga gtttggatcc     300
agaacgagaa acgtcgtgtt cgacattttc accgggaaag gtcaagatat ggtgttcact     360
gtttacggcg agcattggag gaagatgaga agaatcatga cggttccttt cttcaccaac     420
aaagttgttc aacagaatcg tgaaggttgg gagtttgaag cagctagtgt tgttgaagat     480
gttaagaaga atccagattc tgctacgaaa ggaatcgtgt tgaggaaacg tttgcaattg     540
atgatgtata caatatgtt ccgtatcatg ttcgatagaa gatttgagag tgaggatgat     600
cctcttttcc ttaggcttaa ggctttgaat ggtgagagaa gtcgattagc tcagagcttt     660
gagtataact atggagattt cattcctatc cttagaccat tcctcagagg ctatttgaag     720
atttgtcaag atgtgaaaga tcgaagaatc gctcttttca agaagtactt tgttgatgag     780
aggaagcaaa ttgcgagttc taagcctaca ggtagtgaag gattgaaatg tgccattgat     840
cacatccttg aagctgagca aagggagaaa tcaacgagg acaatgttct ttacatcgtc     900
gagaacatca atgtcgccgc gattgagaca cattgtggt ctatcgagtg gggaattgca     960
gagctagtga accatcctga atccagagt aagctaagga cgaactcga cacagttctt    1020 ggaccgggtg tgcaagtcac cgagcctgat cttcacaaac ttccatacct tcaagctgtg    1080
gttaaggaga ctcttcgtct gagaatggcg attcctctcc tcgtgcctca catgaacctc    1140
catgatgcga agctcgctgg ctacgatatc ccagcagaaa gcaaaatcct tgttaatgct    1200
tggtggctag caaacaaccc caacagctgg aagaagcctg aagagtttag accagagagg    1260
```

-continued

```
ttctttgaag aagaatcgca cgtggaagct aacggtaatg acttcaggta tgtgccattt    1320
ggtgttggac gtcgaagctg tcccgggatt atattggcat tgcctatttt ggggatcacc    1380
attggtagga tggtccagaa cttcgagctt cttcctcctc aggacagtc taaagtggat     1440 actagtgaga aggtggaca attcagcttg cacatcctta accactccat aatcgttatg     1500
aaaccaagga actgttaa                                                  1518
```

<210> SEQ ID NO 4
<211> LENGTH: 505
<212> TYPE: PRT
<213> ORGANISM: Arabidopsis thaliana

<400> SEQUENCE: 4

```
Met Asp Leu Leu Leu Glu Lys Ser Leu Ile Ala Val Phe Val Ala
1               5                   10                  15

Val Ile Leu Ala Thr Val Ile Ser Lys Leu Arg Gly Lys Lys Leu Lys
            20                  25                  30

Leu Pro Pro Gly Pro Ile Pro Ile Pro Ile Phe Gly Asn Trp Leu Gln
            35                  40                  45

Val Gly Asp Asp Leu Asn His Arg Asn Leu Val Asp Tyr Ala Lys Lys
65          50                  55                  60

Phe Gly Asp Leu Phe Leu Leu Arg Met Gly Gln Arg Asn Leu Val Val
65                  70                  75                  80

Val Ser Ser Pro Asp Leu Thr Lys Glu Val Leu Leu Thr Gln Gly Val
                85                  90                  95

Glu Phe Gly Ser Arg Thr Arg Asn Val Val Phe Asp Ile Phe Thr Gly
                100                 105                 110

Lys Gly Gln Asp Met Val Phe Thr Val Tyr Gly Glu His Trp Arg Lys
            115                 120                 125

Met Arg Arg Ile Met Thr Val Pro Phe Phe Thr Asn Lys Val Val Gln
130                 135                 140

Gln Asn Arg Glu Gly Trp Glu Phe Glu Ala Ala Ser Val Val Glu Asp
145                 150                 155                 160

Val Lys Lys Asn Pro Asp Ser Ala Thr Lys Gly Ile Val Leu Arg Lys
                165                 170                 175

Arg Leu Gln Leu Met Met Tyr Asn Asn Met Phe Arg Ile Met Phe Asp
            180                 185                 190

Arg Arg Phe Glu Ser Glu Asp Asp Pro Leu Phe Leu Arg Leu Lys Ala
            195                 200                 205

Leu Asn Gly Glu Arg Ser Arg Leu Ala Gln Ser Phe Glu Tyr Asn Tyr
    210                 215                 220

Gly Asp Phe Ile Pro Ile Leu Arg Pro Phe Leu Arg Gly Tyr Leu Lys
225                 230                 235                 240

Ile Cys Gln Asp Val Lys Asp Arg Arg Ile Ala Leu Phe Lys Lys Tyr
                245                 250                 255

Phe Val Asp Glu Arg Lys Gln Ile Ala Ser Ser Lys Pro Thr Gly Ser
            260                 265                 270

Glu Gly Leu Lys Cys Ala Ile Asp His Ile Leu Glu Ala Glu Gln Lys
        275                 280                 285

Gly Glu Ile Asn Glu Asp Asn Val Leu Tyr Ile Val Glu Asn Ile Asn
    290                 295                 300

Val Ala Ala Ile Glu Thr Thr Leu Trp Ser Ile Glu Trp Gly Ile Ala
305                 310                 315                 320

Glu Leu Val Asn His Pro Glu Ile Gln Ser Lys Leu Arg Asn Glu Leu
```

|     |     | 325 |     |     |     | 330 |     |     |     | 335 |     |
| --- | --- | --- | --- | --- | --- | --- | --- | --- | --- | --- | --- |
| Asp | Thr | Val | Leu | Gly | Pro | Gly | Val | Gln | Val | Thr | Glu | Pro | Asp | Leu | His |
|     |     |     | 340 |     |     |     | 345 |     |     |     | 350 |

Lys Leu Pro Tyr Leu Gln Ala Val Val Lys Glu Thr Leu Arg Leu Arg
            355                 360                 365

Met Ala Ile Pro Leu Leu Val Pro His Met Asn Leu His Asp Ala Lys
        370                 375                 380

Leu Ala Gly Tyr Asp Ile Pro Ala Glu Ser Lys Ile Leu Val Asn Ala
385                 390                 395                 400

Trp Trp Leu Ala Asn Asn Pro Asn Ser Trp Lys Lys Pro Glu Glu Phe
                405                 410                 415

Arg Pro Glu Arg Phe Glu Glu Ser His Val Glu Ala Asn Gly
            420                 425                 430

Asn Asp Phe Arg Tyr Val Pro Phe Gly Val Gly Arg Arg Ser Cys Pro
                435                 440                 445

Gly Ile Ile Leu Ala Leu Pro Ile Leu Gly Ile Thr Ile Gly Arg Met
450                 455                 460

Val Gln Asn Phe Glu Leu Leu Pro Pro Gly Gln Ser Lys Val Asp
465                 470                 475                 480

Thr Ser Glu Lys Gly Gly Gln Phe Ser Leu His Ile Leu Asn His Ser
                485                 490                 495

Ile Ile Val Met Lys Pro Arg Asn Cys
            500                 505

<210> SEQ ID NO 5
<211> LENGTH: 1686
<212> TYPE: DNA
<213> ORGANISM: Arabidopsis thaliana

<400> SEQUENCE: 5

```
atggcgccac aagaacaagc agtttctcag gtgatggaga acagagcaa caacaacaac        60
agtgacgtca ttttccgatc aaagttaccg gatatttaca tcccgaacca cctatctctc       120
cacgactaca tcttccaaaa catctccgaa ttcgccacta gccttgcct aatcaacgga        180
ccaaccggcc acgtgtacac ttactccgac gtccacgtca tctcccgcca aatcgccgcc       240
aattttcaca actcggcgt taaccaaaac gacgtcgtca tgctcctcct cccaaactgt       300
cccgaattcg tcctctcttt cctcgccgcc tccttccgcg cgcaaccgc caccgccgca       360
aaccctttct tcactccggc ggagatagct aaacaagcca agcctccaa caccaaactc       420
ataatcaccg aagctcgtta cgtcgacaaa atcaaaccac ttcaaaacga cgacggagta       480
gtcatcgtct gcatcgacga caacgaatcc gtgccaatcc ctgaaggctg cctccgcttc       540
accgagttga ctcagtcgac aaccgaggca tcagaagtca tcgactcggt ggagatttca       600
ccggacgacg tggtggcact accttactcc tctggcacga cgggattacc aaaaggagtg       660
atgctgactc acaagggact agtcacgagc gttgctcagc aagtcgacgg cgagaacccg       720
aatctttatt tccacagcga tgacgtcata ctctgtgttt tgcccatgtt tcatatctac       780
gctttgaact cgatcatgtt gtgtggtctt agagttggtg cggcgattct gataatgccg       840
aagtttgaga tcaatctgct attggagctg atccagaggt gtaaagtgac ggtggctccg       900
atggttccgc cgattgtgtt ggccattgcg aagtcttcgg agacggagaa gtatgatttg       960
agctcgataa gagtggtgaa atctggtgct gctcctcttg gtaaagaact tgaagatgcc      1020
gttaatgcca gtttcctaa tgccaaactc ggtcagggat acggaatgac ggaagcaggt      1080
```

```
ccagtgctag caatgtcgtt aggttttgca aaggaacctt ttccggttaa gtcaggagct    1140
tgtggtactg ttgtaagaaa tgctgagatg aaaatagttg atccagacac cggagattct    1200
ctttcgagga atcaacccgg tgagatttgt attcgtggtc accagatcat gaaaggttac    1260
ctcaacaatc cggcagctac agcagagacc attgataaag acggttggct tcatactgga    1320
gatattggat tgatcgatga cgatgacgag cttttcatcg ttgatcgatt gaaagaactt    1380
atcaagtata aaggttttca ggtagctccg gctgagctag aggctttgct catcggtcat    1440
cctgacatta ctgatgttgc tgttgtcgca atgaaagaag aagcagctgg tgaagttcct    1500
gttgcatttg tggtgaaatc gaaggattcg gagttatcag aagatgatgt gaagcaattc    1560
gtgtcgaaac aggttgtgtt ttacaagaga atcaacaaag tgttcttcac tgaatccatt    1620
cctaaagctc catcagggaa gatattgagg aaagatctga gggcaaaact agcaaatgga    1680
ttgtga                                                               1686
```

<210> SEQ ID NO 6
<211> LENGTH: 561
<212> TYPE: PRT
<213> ORGANISM: Arabidopsis thaliana

<400> SEQUENCE: 6

```
Met Ala Pro Gln Glu Gln Ala Val Ser Gln Val Met Glu Lys Gln Ser
1               5                   10                  15

Asn Asn Asn Ser Asp Val Ile Phe Arg Ser Lys Leu Pro Asp Ile
            20                  25                  30

Tyr Ile Pro Asn His Leu Ser Leu His Asp Tyr Ile Phe Gln Asn Ile
        35                  40                  45

Ser Glu Phe Ala Thr Lys Pro Cys Leu Ile Asn Gly Pro Thr Gly His
    50                  55                  60

Val Tyr Thr Tyr Ser Asp Val His Val Ile Ser Arg Gln Ile Ala Ala
65                  70                  75                  80

Asn Phe His Lys Leu Gly Val Asn Gln Asn Asp Val Val Met Leu Leu
                85                  90                  95

Leu Pro Asn Cys Pro Glu Phe Val Leu Ser Phe Leu Ala Ala Ser Phe
            100                 105                 110

Arg Gly Ala Thr Ala Thr Ala Ala Asn Pro Phe Phe Thr Pro Ala Glu
        115                 120                 125

Ile Ala Lys Gln Ala Lys Ala Ser Asn Thr Lys Leu Ile Ile Thr Glu
    130                 135                 140

Ala Arg Tyr Val Asp Lys Ile Lys Pro Leu Gln Asn Asp Asp Gly Val
145                 150                 155                 160

Val Ile Val Cys Ile Asp Asp Asn Glu Ser Val Pro Ile Pro Glu Gly
                165                 170                 175

Cys Leu Arg Phe Thr Glu Leu Thr Gln Ser Thr Thr Glu Ala Ser Glu
            180                 185                 190

Val Ile Asp Ser Val Glu Ile Ser Pro Asp Val Val Ala Leu Pro
        195                 200                 205

Tyr Ser Ser Gly Thr Thr Gly Leu Pro Lys Gly Val Met Leu Thr His
    210                 215                 220

Lys Gly Leu Val Thr Ser Val Ala Gln Gln Val Asp Gly Glu Asn Pro
225                 230                 235                 240

Asn Leu Tyr Phe His Ser Asp Asp Val Ile Leu Cys Val Leu Pro Met
                245                 250                 255

Phe His Ile Tyr Ala Leu Asn Ser Ile Met Leu Cys Gly Leu Arg Val
```

| | | | | | | | 260 | | | 265 | | | 270 | | |
|---|---|---|---|---|---|---|---|---|---|---|---|---|---|---|---|

Gly Ala Ala Ile Leu Ile Met Pro Lys Phe Glu Ile Asn Leu Leu Leu
            275                 280                 285
Glu Leu Ile Gln Arg Cys Lys Val Thr Val Ala Pro Met Val Pro Pro
            290                 295                 300
Ile Val Leu Ala Ile Ala Lys Ser Ser Glu Thr Glu Lys Tyr Asp Leu
305                 310                 315                 320
Ser Ser Ile Arg Val Val Lys Ser Gly Ala Ala Pro Leu Gly Lys Glu
            325                 330                 335
Leu Glu Asp Ala Val Asn Ala Lys Phe Pro Asn Ala Lys Leu Gly Gln
            340                 345                 350
Gly Tyr Gly Met Thr Glu Ala Gly Pro Val Leu Ala Met Ser Leu Gly
            355                 360                 365
Phe Ala Lys Glu Pro Phe Pro Val Lys Ser Gly Ala Cys Gly Thr Val
            370                 375                 380
Val Arg Asn Ala Glu Met Lys Ile Val Asp Pro Asp Thr Gly Asp Ser
385                 390                 395                 400
Leu Ser Arg Asn Gln Pro Gly Glu Ile Cys Ile Arg Gly His Gln Ile
            405                 410                 415
Met Lys Gly Tyr Leu Asn Asn Pro Ala Ala Thr Ala Glu Thr Ile Asp
            420                 425                 430
Lys Asp Gly Trp Leu His Thr Gly Asp Ile Gly Leu Ile Asp Asp Asp
            435                 440                 445
Asp Glu Leu Phe Ile Val Asp Arg Leu Lys Glu Leu Ile Lys Tyr Lys
            450                 455                 460
Gly Phe Gln Val Ala Pro Ala Glu Leu Glu Ala Leu Leu Ile Gly His
465                 470                 475                 480
Pro Asp Ile Thr Asp Val Ala Val Val Ala Met Lys Glu Glu Ala Ala
            485                 490                 495
Gly Glu Val Pro Val Ala Phe Val Val Lys Ser Lys Asp Ser Glu Leu
            500                 505                 510
Ser Glu Asp Asp Val Lys Gln Phe Val Ser Lys Gln Val Val Phe Tyr
            515                 520                 525
Lys Arg Ile Asn Lys Val Phe Phe Thr Glu Ser Ile Pro Lys Ala Pro
            530                 535                 540
Ser Gly Lys Ile Leu Arg Lys Asp Leu Arg Ala Lys Leu Ala Asn Gly
545                 550                 555                 560
Leu

<210> SEQ ID NO 7
<211> LENGTH: 1176
<212> TYPE: DNA
<213> ORGANISM: Rheum tataricum

<400> SEQUENCE: 7
atggcaccgg aggagtccag gcatgctgaa actgcagtta acagagccgc caccgtcctg      60
gccatcggca ctgccaaccc gccaaactgc tactatcaag cggacttttcc tgacttctac     120 ttccgtgcca ccaacagcga ccacctcacg cacctcaagc aaaaatttaa gcgcatttgt     180
gagaaatcga tgattgaaaa acgttatctc catttgacgg aagaaattct caaggagaat     240
ccaaatattg cttccttcga ggcgccatca ttggatgtaa acataacat tcaagtgaaa      300 gaagtggtgc tgctcggaaa agaggcagct ttgaaggcca tcaatgagtg gggccaaccc     360
aagtcaaaga tcacgcgcct cattgtgtgt tgtattgccg gcgttgacat gcccggcgca     420

```
gactatcaac tcactaaact ccttggctta caactttctg ttaagcgatt tatgttttac      480
cacctaggat gctatgccgg tggcaccgtc cttcgccttg cgaaggacat agcagaaaac      540
aacaaggaag ctcgtgttct catcgttcgc tctgagatga cgccaatctg tttccgtggg      600
ccatccgaaa cccacataga ctccatggta gggcaagcaa tatttggtga cggtgctgcg      660
gctgttatag ttggtgcaaa tcccgaccta ccatcgaaa ggccgatttt cgagttgatt       720
tctacatccc aaactatcat acctgaatcc gatggtgcga ttgagggaca tttgcttgaa      780
gttggactca gtttccaact ctaccagact gttccctcat aatctctaa ttgtatcgaa       840 acttgtcttt caaggctttt cacacctctt aacattagtg attggaactc actattctgg      900
attgcacacc ctggtggccg tgctatcctt gacgatatcg aggctactgt tggtctcaag      960
aaggagaaac ttaaggcaac aagacaagtt ttgaacgact atgggaacat gtcaagtgct     1020 tgcgtattt tcatcatgga tgagatgagg aagaagtcgc tcgcaaacgg tcaagtaacc     1080
actggagaag gactcaagtg gggtgttctt tttgggttcg ggccaggtgt tactgtggaa     1140
actgtggttc taagcagtgt gccgctaatt acctga                              1176

<210> SEQ ID NO 8
<211> LENGTH: 391
<212> TYPE: PRT
<213> ORGANISM: Rheum tataricum

<400> SEQUENCE: 8

Met Ala Pro Glu Glu Ser Arg His Ala Glu Thr Ala Val Asn Arg Ala
1               5                   10                  15

Ala Thr Val Leu Ala Ile Gly Thr Ala Asn Pro Pro Asn Cys Tyr Tyr
                20                  25                  30

Gln Ala Asp Phe Pro Asp Phe Tyr Phe Arg Ala Thr Asn Ser Asp His
            35                  40                  45

Leu Thr His Leu Lys Gln Lys Phe Lys Arg Ile Cys Glu Lys Ser Met
        50                  55                  60

Ile Glu Lys Arg Tyr Leu His Leu Thr Glu Glu Ile Leu Lys Glu Asn
65                  70                  75                  80

Pro Asn Ile Ala Ser Phe Glu Ala Pro Ser Leu Asp Val Arg His Asn
                85                  90                  95

Ile Gln Val Lys Glu Val Val Leu Leu Gly Lys Glu Ala Ala Leu Lys
            100                 105                 110

Ala Ile Asn Glu Trp Gly Gln Pro Lys Ser Lys Ile Thr Arg Leu Ile
        115                 120                 125

Val Cys Cys Ile Ala Gly Val Asp Met Pro Gly Ala Asp Tyr Gln Leu
    130                 135                 140

Thr Lys Leu Leu Gly Leu Gln Leu Ser Val Lys Arg Phe Met Phe Tyr
145                 150                 155                 160

His Leu Gly Cys Tyr Ala Gly Gly Thr Val Leu Arg Leu Ala Lys Asp
                165                 170                 175

Ile Ala Glu Asn Asn Lys Glu Ala Arg Val Leu Ile Val Arg Ser Glu
            180                 185                 190

Met Thr Pro Ile Cys Phe Arg Gly Pro Ser Glu Thr His Ile Asp Ser
        195                 200                 205

Met Val Gly Gln Ala Ile Phe Gly Asp Gly Ala Ala Ala Val Ile Val
    210                 215                 220

Gly Ala Asn Pro Asp Leu Ser Ile Glu Arg Pro Ile Phe Glu Leu Ile
225                 230                 235                 240
```

```
Ser Thr Ser Gln Thr Ile Ile Pro Glu Ser Asp Gly Ala Ile Glu Gly
            245                 250                 255

His Leu Leu Glu Val Gly Leu Ser Phe Gln Leu Tyr Gln Thr Val Pro
        260                 265                 270

Ser Leu Ile Ser Asn Cys Ile Glu Thr Cys Leu Ser Lys Ala Phe Thr
    275                 280                 285

Pro Leu Asn Ile Ser Asp Trp Asn Ser Leu Phe Trp Ile Ala His Pro
290                 295                 300

Gly Gly Arg Ala Ile Leu Asp Asp Ile Glu Ala Thr Val Gly Leu Lys
305                 310                 315                 320

Lys Glu Lys Leu Lys Ala Thr Arg Gln Val Leu Asn Asp Tyr Gly Asn
                325                 330                 335

Met Ser Ser Ala Cys Val Phe Phe Ile Met Asp Glu Met Arg Lys Lys
            340                 345                 350

Ser Leu Ala Asn Gly Gln Val Thr Thr Gly Glu Gly Leu Lys Trp Gly
        355                 360                 365

Val Leu Phe Gly Phe Gly Pro Gly Val Thr Val Glu Thr Val Val Leu
    370                 375                 380

Ser Ser Val Pro Leu Ile Thr
385                 390

<210> SEQ ID NO 9
<211> LENGTH: 1176
<212> TYPE: DNA
<213> ORGANISM: Rheum tataricum

<400> SEQUENCE: 9
atggccccag aagagagcag gcacgcagaa acggccgtta acagagctgc aactgttttg      60
gctattggta cggccaatcc acccaattgt tactatcaag ctgactttcc tgatttttat     120
ttcagagcca caaatagcga tcatttgact catcttaagc aaaaatttaa aaggatatgc     180
gagaagtcca tgattgaaaa agatacttg caccttaccg aagagatctt aaaagaaaac     240
ccaaatatag cttcttttga agctccctcc ttagatgtac gtcacaacat tcaagtcaag     300
gaggtggttt tacttggtaa ggaagccgca ttgaaagcta taacgaatg gggacagcct     360 aaaagtaaga taaccagatt gatcgtatgt tgcatagctg gcgttgacat gcctggtgca     420
gattatcaac taacaaaatt gctgggtcta caattatccg taaaaaggtt tatgttctac     480
catttaggct gttacgctgg tggcacagtt ttaagactgg ctaaggatat agcagaaaat     540
aacaaggagg ctagagtctt aatagtgcgt agtgaaatga ctcctatttg ctttagaggt     600
ccatcagaaa cacatatcga cagcatggta ggtcaggcaa ttttcggtga tggtgctgca     660
gccgtaattg tgggagctaa tcctgattta agtatcgaaa gacctatttt tgaacttatt     720
tctacttcgc aaaccattat ccccgaatca gatggtgcaa ttgaaggcca tttattggag     780
gttggtttgt cctttcaatt gtatcagaca gtgccatctt taatttcaaa ctgtatagaa     840
acctgtctaa gtaaagcatt tacaccatta aacatttctg actggaattc tttgttctgg     900
attgctcatc caggtggaag agccatctta gatgacatcg aagctactgt gggactgaaa     960
aaggaaaaac taaagctac tagacaagtt ttaaatgact acggtaatat gtcatctgct    1020
tgtgtatttt tcattatgga tgagatgaga aaaagtcac ttgcaaatgg ccaggtcacg    1080
acaggtgagg gtctaaaatg gggagtccta ttcggattcg gcccaggtgt cactgttgaa    1140
accgttgtcc tgtcttcggt tccattgatc acttaa                              1176
```

<210> SEQ ID NO 10
<211> LENGTH: 391
<212> TYPE: PRT
<213> ORGANISM: Rheum tataricum

<400> SEQUENCE: 10

```
Met Ala Pro Glu Glu Ser Arg His Ala Glu Thr Ala Val Asn Arg Ala
 1               5                  10                  15

Ala Thr Val Leu Ala Ile Gly Thr Ala Asn Pro Pro Asn Cys Tyr Tyr
             20                  25                  30

Gln Ala Asp Phe Pro Asp Phe Tyr Arg Ala Thr Asn Ser Asp His
         35                  40                  45

Leu Thr His Leu Lys Gln Lys Phe Lys Arg Ile Cys Glu Lys Ser Met
 50                  55                  60

Ile Glu Lys Arg Tyr Leu His Leu Thr Glu Glu Ile Leu Lys Glu Asn
 65                  70                  75                  80

Pro Asn Ile Ala Ser Phe Glu Ala Pro Ser Leu Asp Val Arg His Asn
                 85                  90                  95

Ile Gln Val Lys Glu Val Val Leu Leu Gly Lys Glu Ala Ala Leu Lys
             100                 105                 110

Ala Ile Asn Glu Trp Gly Gln Pro Lys Ser Lys Ile Thr Arg Leu Ile
             115                 120                 125

Val Cys Cys Ile Ala Gly Val Asp Met Pro Gly Ala Asp Tyr Gln Leu
130                 135                 140

Thr Lys Leu Leu Gly Leu Gln Leu Ser Val Lys Arg Phe Met Phe Tyr
145                 150                 155                 160

His Leu Gly Cys Tyr Ala Gly Gly Thr Val Leu Arg Leu Ala Lys Asp
                 165                 170                 175

Ile Ala Glu Asn Asn Lys Glu Ala Arg Val Leu Ile Val Arg Ser Glu
             180                 185                 190

Met Thr Pro Ile Cys Phe Arg Gly Pro Ser Glu Thr His Ile Asp Ser
             195                 200                 205

Met Val Gly Gln Ala Ile Phe Gly Asp Gly Ala Ala Ala Val Ile Val
210                 215                 220

Gly Ala Asn Pro Asp Leu Ser Ile Glu Arg Pro Ile Phe Glu Leu Ile
225                 230                 235                 240

Ser Thr Ser Gln Thr Ile Ile Pro Glu Ser Asp Gly Ala Ile Glu Gly
                 245                 250                 255

His Leu Leu Glu Val Gly Leu Ser Phe Gln Leu Tyr Gln Thr Val Pro
             260                 265                 270

Ser Leu Ile Ser Asn Cys Ile Glu Thr Cys Leu Ser Lys Ala Phe Thr
             275                 280                 285

Pro Leu Asn Ile Ser Asp Trp Asn Ser Leu Phe Trp Ile Ala His Pro
         290                 295                 300

Gly Gly Arg Ala Ile Leu Asp Asp Ile Glu Ala Thr Val Gly Leu Lys
305                 310                 315                 320

Lys Glu Lys Leu Lys Ala Thr Arg Gln Val Leu Asn Asp Tyr Gly Asn
                 325                 330                 335

Met Ser Ser Ala Cys Val Phe Phe Ile Met Asp Glu Met Arg Lys Lys
             340                 345                 350

Ser Leu Ala Asn Gly Gln Val Thr Thr Gly Glu Gly Leu Lys Trp Gly
         355                 360                 365

Val Leu Phe Gly Phe Gly Pro Gly Val Thr Val Glu Thr Val Val Leu
370                 375                 380
```

Ser Ser Val Pro Leu Ile Thr
385                 390

<210> SEQ ID NO 11
<211> LENGTH: 1596
<212> TYPE: DNA
<213> ORGANISM: Rhodobacter capsulatus

<400> SEQUENCE: 11

| | | | | | |
|---|---|---|---|---|---|
| atgaccctgc | agtcacagac | ggccaaggac | tgcctcgcgc | tggacggggc | gctgacactt | 60 |
| gtccaatgcg | aggccatcgc | gacacatcgc | agccggattt | cggtgacccc | cgcgctgcgc | 120 |
| gagcgctgcg | cgcgggccca | tgcccggctt | gagcacgcca | tcgccgagca | gcgccacatt | 180 |
| tacggcatca | ccaccggctt | cggcccgctg | gcgaaccgtc | tgatcggggc | cgatcagggg | 240 |
| gcggagctgc | agcagaacct | gatctatcat | ctggccaccg | gcgtcgggcc | gaaactgagc | 300 |
| tgggccgagg | cgcgggcgtt | gatgctggcg | cggctcaact | cgatcctgca | aggcgcgtcg | 360 |
| ggggcctcgc | cggagacgat | cgaccggatc | gttgcggtgc | tcaatgcggg | gtttgccccc | 420 |
| gaggttccgg | cgcagggaac | ggtgggcgcc | tcggcgatc | tgaccccgct | tgcgcatatg | 480 |
| gtgctggcgc | tgcaggacg | ggggcggatg | atcgaccct | cgggccgcgt | gcaggaggcc | 540 |
| ggggcggtga | tggatcggct | ctgcggcggt | ccgctgacgc | tggcggcccg | tgacgggctg | 600 |
| gcgctggtga | atggcacctc | ggcgatgacc | gcgattgcgg | ccctgaccgg | ggtcgaggcg | 660 |
| gcgcgggcga | tcgacgccgc | gcttcggcac | agcgcggtcc | tgatggaggt | cttgtccggt | 720 |
| catgccgaag | cctggcatcc | ggctttcgca | gagctgcgcc | cgcatccggg | gcagctgcgg | 780 |
| gcgaccgagc | ggctggcgca | ggcgctggat | ggggcggggc | gggtctgtcg | gaccctgacc | 840 |
| gcggcgcggc | ggctgaccgc | cgcggatctg | cggcccgaag | atcatccggc | caggatgcc | 900 |
| tacagtctgc | gcgtggtgcc | gcaactggtc | ggcgcggtct | gggacacgct | ggactggcac | 960 |
| gatcgtgtcg | tcacctgcga | gctcaattcc | gtcaccgaca | tccgatcttt | cccgagggc | 1020 |
| tgcgcggtgc | ccgccctgca | cggcggcaat | tcatgggcg | tgcatgtcgc | ccttgcctcc | 1080 |
| gatgcgctga | acgcggcgct | ggtgacgctg | gcgggcctgg | tcgagcgtca | gatcgcccgg | 1140 |
| ctgaccgacg | aaaagctgaa | caagggcctg | ccgccttcc | tgcacggggg | gcaggcgggg | 1200 |
| ctgcaatcgg | gcttcatggg | ggcgcaggtc | acggcgacgg | cgcttctggc | ggaaatgcgg | 1260 |
| gcgaatgcca | cgccggtttc | ggtgcagtcg | ctgtcgacca | atggcgccaa | tcaggatgtg | 1320 |
| gtctcgatgg | gaacgattgc | cgcgcggagg | gcgcgggcgc | agctgctgcc | cctgtcgcag | 1380 |
| atccaggcga | tcctggcgct | tgcccttgcc | caggcgatgg | atctgcttga | cgaccccgag | 1440 |
| ggcaggccg | gatggtcgct | tacgcgcgcg | gatctgcggg | accggatccg | gcggtctcg | 1500 |
| cccgggcttc | gcgccgacag | accgcttgcc | gggcatatcg | aagcggtggc | acagggtctg | 1560 |
| cgtcatccct | ccgccgccgc | cgatccccg | gcatga | | | 1596 |

<210> SEQ ID NO 12
<211> LENGTH: 531
<212> TYPE: PRT
<213> ORGANISM: Rhodobacter capsulatus

<400> SEQUENCE: 12

Met Thr Leu Gln Ser Gln Thr Ala Lys Asp Cys Leu Ala Leu Asp Gly
1               5                   10                  15

Ala Leu Thr Leu Val Gln Cys Glu Ala Ile Ala Thr His Arg Ser Arg
            20                  25                  30

```
Ile Ser Val Thr Pro Ala Leu Arg Glu Arg Cys Ala Arg Ala His Ala
        35                  40                  45

Arg Leu Glu His Ala Ile Ala Glu Gln Arg His Ile Tyr Gly Ile Thr
 50                  55                  60

Thr Gly Phe Gly Pro Leu Ala Asn Arg Leu Ile Gly Ala Asp Gln Gly
 65                  70                  75                  80

Ala Glu Leu Gln Gln Asn Leu Ile Tyr His Leu Ala Thr Gly Val Gly
                 85                  90                  95

Pro Lys Leu Ser Trp Ala Glu Ala Arg Ala Leu Met Leu Ala Arg Leu
                100                 105                 110

Asn Ser Ile Leu Gln Gly Ala Ser Gly Ala Ser Pro Glu Thr Ile Asp
            115                 120                 125

Arg Ile Val Ala Val Leu Asn Ala Gly Phe Ala Pro Glu Val Pro Ala
130                 135                 140

Gln Gly Thr Val Gly Ala Ser Gly Asp Leu Thr Pro Leu Ala His Met
145                 150                 155                 160

Val Leu Ala Leu Gln Gly Arg Gly Arg Met Ile Asp Pro Ser Gly Arg
                165                 170                 175

Val Gln Glu Ala Gly Ala Val Met Asp Arg Leu Cys Gly Gly Pro Leu
            180                 185                 190

Thr Leu Ala Ala Arg Asp Gly Leu Ala Leu Val Asn Gly Thr Ser Ala
        195                 200                 205

Met Thr Ala Ile Ala Ala Leu Thr Gly Val Glu Ala Ala Arg Ala Ile
210                 215                 220

Asp Ala Ala Leu Arg His Ser Ala Val Leu Met Glu Val Leu Ser Gly
225                 230                 235                 240

His Ala Glu Ala Trp His Pro Ala Phe Ala Glu Leu Arg Pro His Pro
                245                 250                 255

Gly Gln Leu Arg Ala Thr Glu Arg Leu Ala Gln Ala Leu Asp Gly Ala
            260                 265                 270

Gly Arg Val Cys Arg Thr Leu Thr Ala Ala Arg Arg Leu Thr Ala Ala
        275                 280                 285

Asp Leu Arg Pro Glu Asp His Pro Ala Gln Asp Ala Tyr Ser Leu Arg
290                 295                 300

Val Val Pro Gln Leu Val Gly Ala Val Trp Asp Thr Leu Asp Trp His
305                 310                 315                 320

Asp Arg Val Val Thr Cys Glu Leu Asn Ser Val Thr Asp Asn Pro Ile
                325                 330                 335

Phe Pro Glu Gly Cys Ala Val Pro Ala Leu His Gly Gly Asn Phe Met
            340                 345                 350

Gly Val His Val Ala Leu Ala Ser Asp Ala Leu Asn Ala Ala Leu Val
        355                 360                 365

Thr Leu Ala Gly Leu Val Glu Arg Gln Ile Ala Arg Leu Thr Asp Glu
370                 375                 380

Lys Leu Asn Lys Gly Leu Pro Ala Phe Leu His Gly Gly Gln Ala Gly
385                 390                 395                 400

Leu Gln Ser Gly Phe Met Gly Ala Gln Val Thr Ala Thr Ala Leu Leu
                405                 410                 415

Ala Glu Met Arg Ala Asn Ala Thr Pro Val Ser Val Gln Ser Leu Ser
            420                 425                 430

Thr Asn Gly Ala Asn Gln Asp Val Val Ser Met Gly Thr Ile Ala Ala
        435                 440                 445
```

Arg Arg Ala Arg Ala Gln Leu Leu Pro Leu Ser Gln Ile Gln Ala Ile
    450                 455                 460

Leu Ala Leu Ala Leu Ala Gln Ala Met Asp Leu Leu Asp Asp Pro Glu
465                 470                 475                 480

Gly Gln Ala Gly Trp Ser Leu Thr Ala Arg Asp Leu Arg Asp Arg Ile
                485                 490                 495

Arg Ala Val Ser Pro Gly Leu Arg Ala Asp Arg Pro Leu Ala Gly His
            500                 505                 510

Ile Glu Ala Val Ala Gln Gly Leu Arg His Pro Ser Ala Ala Ala Asp
        515                 520                 525

Pro Pro Ala
    530

<210> SEQ ID NO 13
<211> LENGTH: 1596
<212> TYPE: DNA
<213> ORGANISM: Rhodobacter capsulatus

<400> SEQUENCE: 13

```
atgaccctgc aatctcaaac agctaaagat tgtttggctt tggatggtgc cttgacatta      60
gttcaatgcg aagcgatagc aacccataga agtagaatct ctgtaacacc agccctacgt     120
gagagatgtg ctagagcaca tgctaggtta aacatgcaa tagccgaaca gcgacacata     180
tatgggataa cgacaggctt cgggccactt gctaacaggc tgatcggagc agaccagggt     240
gctgaattac aacagaacct tatctaccat ttggcaaccg gagttggccc caaattatca     300
tgggccgaag ccagagcttt aatgctcgct cgtttgaata gtatactaca aggtgcttct     360
ggtgctagcc ctgaaacaat tgataggatc gttgcagtct taaatgccgg atttgccccg     420
gaagtcccag cccaaggaac cgttggtgct tcgggtgact taactccgtt agcacacatg     480
gtattagcat tgcaaggcag aggtcgtatg attgatcctt cagggagagt tcaagaagcc     540
ggcgctgtca tggataggtt gtgtggaggc cctttaacat tggctgccag agatggcctc     600
gccttagtaa atggtacatc tgccatgaca gctattgccg cattgaccgg tgtggaggct     660
gcaagagcga ttgatgcagc gcttagacat tccgcagtct tgatggaggt cctgtcaggg     720
catgctgagg cttggcaccc tgcctttgcg gaattgcgtc cgcatccagg acaattacgc     780
gccactgaga ggttagctca agcattggac ggcgcaggta gagtctgccg gactcttaca     840
gccgctaggc gtctaactgc agctgatctg agaccagaag atcatccagc tcaagatgca     900
tattcacttc gagtagttcc tcagctggtt ggtgccgtat gggatacgtt ggattggcac     960
gacagggttg tgacttgcga acttaactcc gtgaccgaca tccaattttt ccccgagggt    1020
tgtgcggttc cagcactaca cggtggaaac tttatgggcg tacatgtggc actagcttct    1080
gacgctttaa atgcagcgtt ggttacatta gctggtctag ttgaaaggca gattgcaaga    1140
cttactgatg agaagttgaa taaggggtttg cctgcttttt tgcatggagg ccaagcaggt    1200
ttacaatcag gtttcatggg agctcaggtt actgctactg ctttgctagc ggaaatgaga    1260
gctaacgcga ctcccgtgtc cgttcaaagc ctcagcacca atggtgcaaa tcaagacgtg    1320
gtaagtatgg gtacgattgc cgcgagacga gcaagagctc aacttttacc tctgtctcaa    1380
atccaagcga ttttggcact ggctcttgca caagccatgg atctcctaga cgatcctgaa    1440
ggacaagccg ttggtccttt aacggcaaga gatttaagag accgtatacg ggctgtcagt    1500
ccagggttgc gcgcagatag accactacgc ggtcatattg aagctgtggc tcaaggtcta    1560
agacacccct cggcagctgc cgatccacct gcttaa                              1596
```

<210> SEQ ID NO 14
<211> LENGTH: 531
<212> TYPE: PRT
<213> ORGANISM: Rhodobacter capsulatus

<400> SEQUENCE: 14

```
Met Thr Leu Gln Ser Gln Thr Ala Lys Asp Cys Leu Ala Leu Asp Gly
1               5                   10                  15

Ala Leu Thr Leu Val Gln Cys Glu Ala Ile Ala Thr His Arg Ser Arg
            20                  25                  30

Ile Ser Val Thr Pro Ala Leu Arg Glu Arg Cys Ala Arg Ala His Ala
        35                  40                  45

Arg Leu Glu His Ala Ile Ala Glu Gln Arg His Ile Tyr Gly Ile Thr
    50                  55                  60

Thr Gly Phe Gly Pro Leu Ala Asn Arg Leu Ile Gly Ala Asp Gln Gly
65                  70                  75                  80

Ala Glu Leu Gln Gln Asn Leu Ile Tyr His Leu Ala Thr Gly Val Gly
                85                  90                  95

Pro Lys Leu Ser Trp Ala Glu Ala Arg Ala Leu Met Leu Ala Arg Leu
            100                 105                 110

Asn Ser Ile Leu Gln Gly Ala Ser Gly Ala Ser Pro Glu Thr Ile Asp
        115                 120                 125

Arg Ile Val Ala Val Leu Asn Ala Gly Phe Ala Pro Glu Val Pro Ala
    130                 135                 140

Gln Gly Thr Val Gly Ala Ser Gly Asp Leu Thr Pro Leu Ala His Met
145                 150                 155                 160

Val Leu Ala Leu Gln Gly Arg Gly Arg Met Ile Asp Pro Ser Gly Arg
                165                 170                 175

Val Gln Glu Ala Gly Ala Val Met Asp Arg Leu Cys Gly Gly Pro Leu
            180                 185                 190

Thr Leu Ala Ala Arg Asp Gly Leu Ala Leu Val Asn Gly Thr Ser Ala
        195                 200                 205

Met Thr Ala Ile Ala Ala Leu Thr Gly Val Glu Ala Ala Arg Ala Ile
    210                 215                 220

Asp Ala Ala Leu Arg His Ser Ala Val Leu Met Glu Val Leu Ser Gly
225                 230                 235                 240

His Ala Glu Ala Trp His Pro Ala Phe Ala Glu Leu Arg Pro His Pro
                245                 250                 255

Gly Gln Leu Arg Ala Thr Glu Arg Leu Ala Gln Ala Leu Asp Gly Ala
            260                 265                 270

Gly Arg Val Cys Arg Thr Leu Thr Ala Ala Arg Arg Leu Thr Ala Ala
        275                 280                 285

Asp Leu Arg Pro Glu Asp His Pro Ala Gln Asp Ala Tyr Ser Leu Arg
    290                 295                 300

Val Val Pro Gln Leu Val Gly Ala Val Trp Asp Thr Leu Asp Trp His
305                 310                 315                 320

Asp Arg Val Val Thr Cys Glu Leu Asn Ser Val Thr Asp Asn Pro Ile
                325                 330                 335

Phe Pro Glu Gly Cys Ala Val Pro Ala Leu His Gly Gly Asn Phe Met
            340                 345                 350

Gly Val His Val Ala Leu Ala Ser Asp Ala Leu Asn Ala Ala Leu Val
        355                 360                 365

Thr Leu Ala Gly Leu Val Glu Arg Gln Ile Ala Arg Leu Thr Asp Glu
```

```
                370             375             380
Lys Leu Asn Lys Gly Leu Pro Ala Phe Leu His Gly Gly Gln Ala Gly
385             390                 395                 400

Leu Gln Ser Gly Phe Met Gly Ala Gln Val Thr Ala Thr Ala Leu Leu
            405                 410                 415

Ala Glu Met Arg Ala Asn Ala Thr Pro Val Ser Val Gln Ser Leu Ser
                420                 425                 430

Thr Asn Gly Ala Asn Gln Asp Val Val Ser Met Gly Thr Ile Ala Ala
            435                 440                 445

Arg Arg Ala Arg Ala Gln Leu Leu Pro Leu Ser Gln Ile Gln Ala Ile
        450                 455                 460

Leu Ala Leu Ala Leu Ala Gln Ala Met Asp Leu Leu Asp Asp Pro Glu
465                 470                 475                 480

Gly Gln Ala Gly Trp Ser Leu Thr Ala Arg Asp Leu Arg Asp Arg Ile
                485                 490                 495

Arg Ala Val Ser Pro Gly Leu Arg Ala Asp Arg Pro Leu Ala Gly His
            500                 505                 510

Ile Glu Ala Val Ala Gln Gly Leu Arg His Pro Ser Ala Ala Ala Asp
        515                 520                 525

Pro Pro Ala
    530

<210> SEQ ID NO 15
<211> LENGTH: 2076
<212> TYPE: DNA
<213> ORGANISM: Saccharomyces cerevisiae

<400> SEQUENCE: 15
atgccgtttg aatagacaa caccgacttc actgtcctgg cggggctagt gcttgccgtg     60
ctactgtacg taaagagaaa ctccatcaag gaactgctga tgtccgatga cggagatatc    120
acagctgtca gctcgggcaa cagagacatt gctcaggtgg tgaccgaaaa caacaagaac    180
tacttggtgt tgtatgcgtc gcagactggg actgccgagg attacgccaa aaagttttcc    240
aaggagctgg tggccaagtt caacctaaac gtgatgtgcg cagatgttga gaactacgac    300
tttgagtcgc taaacgatgt gcccgtcata gtctcgattt ttatctctac atatggtgaa    360
ggagacttcc ccgacggggc ggtcaacttt gaagacttta tttgtaatgc ggaagcgggt    420
gcactatcga acctgaggta atatgtgttt ggtctgggaa attctactta tgaattcttt    480
aatggtgccg ccaagaaggc cgagaagcat ctctccgccg cgggcgctat cagactaggc    540
aagctcggtg aagctgatga tggtgcagga actacagacg aagattacat ggcctggaag    600
gactccatcc tggaggtttt gaaagacgaa ctgcatttgg acgaacagga agccaagttc    660
acctctcaat tccagtacac tgtgttgaac gaaatcactg actccatgtc gcttggtgaa    720
ccctctgctc actatttgcc ctcgcatcag ttgaaccgca acgcagacgg catccaattg    780
ggtcccttcg atttgtctca accgtatatt gcacccatcg tgaaatctcg gaactgttc    840 tcttccaatg accgtaattg catccactct gaatttgact tgtccggctc taacatcaag    900
tactccactg tgaccatctt gctgtttggg ccttccaacc cattggaaaa ggtcgaacag    960
ttcttatcca tattcaacct ggaccctgaa accattttg acttgaagcc cctggatccc   1020
accgtcaaag tgcccttccc aacgccaact actattggcg ctgctattaa acactatttg   1080
gaaattacag acctgtctc cagacaattg ttttcatctt tgattcagtt cgcccccaac   1140
gctgacgtca aggaaaaatt gactctgctt tcgaaagaca aggaccaatt cgccgtcgag   1200
```

```
ataacctcca aatatttcaa catcgcagat gctctgaaat atttgtctga tggcgccaaa    1260
tgggacaccg tacccatgca attcttggtc gaatcagttc cccaaatgac tcctcgttac    1320
tactctatct cttcctcttc tctgtctgaa agcaaaccg tccatgtcac ctccattgtg     1380
gaaaactttc ctaacccaga attgcctgat gctcctccag ttgttggtgt tacgactaac    1440
ttgttaagaa acattcaatt ggctcaaaac aatgttaaca ttgccgaaac taacctacct    1500
gttcactacg atttaaatgg cccacgtaaa cttttcgcca attacaaatt gcccgtccac    1560
gttcgtcgtt ctaacttcag attgccttcc aacccttcca ccccagttat catgatcggt    1620
ccaggtaccg tgttgcccc attccgtggg tttatcagag agcgtgtcgc gttcctcgaa     1680
tcacaaaaga agggcggtaa caacgtttcg ctaggtaagc atatactgtt ttatggatcc    1740
cgtaacactg atgatttctt gtaccaggac gaatggccag aatacgccaa aaaattggat    1800
ggttcgttcg aaatggtcgt ggcccattcc aggttgccaa acaccaaaaa agtttatgtt    1860
caagataaat taaaggatta cgaagaccaa gtatttgaaa tgattaacaa cggtgcattt    1920
atctacgtct gtggtgatgc aaagggtatg gccaagggtg tgtcaaccgc attggttggc    1980
atcttatccc gtggtaaatc cattaccact gatgaagcaa cagagctaat caagatgctc    2040
aagacttcag gtagatacca agaagatgtc tggtaa                              2076
```

<210> SEQ ID NO 16
<211> LENGTH: 691
<212> TYPE: PRT
<213> ORGANISM: Saccharomyces cerevisiae

<400> SEQUENCE: 16

```
Met Pro Phe Gly Ile Asp Asn Thr Asp Phe Thr Val Leu Ala Gly Leu
1               5                   10                  15

Val Leu Ala Val Leu Leu Tyr Val Lys Arg Asn Ser Ile Lys Glu Leu
            20                  25                  30

Leu Met Ser Asp Asp Gly Asp Ile Thr Ala Val Ser Ser Gly Asn Arg
        35                  40                  45

Asp Ile Ala Gln Val Val Thr Glu Asn Asn Lys Asn Tyr Leu Val Leu
    50                  55                  60

Tyr Ala Ser Gln Thr Gly Thr Ala Glu Asp Tyr Ala Lys Lys Phe Ser
65                  70                  75                  80

Lys Glu Leu Val Ala Lys Phe Asn Leu Asn Val Met Cys Ala Asp Val
                85                  90                  95

Glu Asn Tyr Asp Phe Glu Ser Leu Asn Asp Val Pro Val Ile Val Ser
            100                 105                 110

Ile Phe Ile Ser Thr Tyr Gly Glu Gly Asp Phe Pro Asp Gly Ala Val
        115                 120                 125

Asn Phe Glu Asp Phe Ile Cys Asn Ala Glu Ala Gly Ala Leu Ser Asn
    130                 135                 140

Leu Arg Tyr Asn Met Phe Gly Leu Gly Asn Ser Thr Tyr Glu Phe Phe
145                 150                 155                 160

Asn Gly Ala Ala Lys Lys Ala Glu Lys His Leu Ser Ala Ala Gly Ala
                165                 170                 175

Ile Arg Leu Gly Lys Leu Gly Glu Ala Asp Asp Gly Ala Gly Thr Thr
            180                 185                 190

Asp Glu Asp Tyr Met Ala Trp Lys Asp Ser Ile Leu Glu Val Leu Lys
        195                 200                 205

Asp Glu Leu His Leu Asp Glu Gln Glu Ala Lys Phe Thr Ser Gln Phe
```

```
            210                 215                 220
Gln Tyr Thr Val Leu Asn Glu Ile Thr Asp Ser Met Ser Leu Gly Glu
225                 230                 235                 240

Pro Ser Ala His Tyr Leu Pro Ser His Gln Leu Asn Arg Asn Ala Asp
                245                 250                 255

Gly Ile Gln Leu Gly Pro Phe Asp Leu Ser Gln Pro Tyr Ile Ala Pro
                260                 265                 270

Ile Val Lys Ser Arg Glu Leu Phe Ser Ser Asn Asp Arg Asn Cys Ile
            275                 280                 285

His Ser Glu Phe Asp Leu Ser Gly Ser Asn Ile Lys Tyr Ser Thr Gly
            290                 295                 300

Asp His Leu Ala Val Trp Pro Ser Asn Pro Leu Glu Lys Val Glu Gln
305                 310                 315                 320

Phe Leu Ser Ile Phe Asn Leu Asp Pro Glu Thr Ile Phe Asp Leu Lys
                325                 330                 335

Pro Leu Asp Pro Thr Val Lys Val Pro Phe Pro Thr Pro Thr Thr Ile
                340                 345                 350

Gly Ala Ala Ile Lys His Tyr Leu Glu Ile Thr Gly Pro Val Ser Arg
                355                 360                 365

Gln Leu Phe Ser Ser Leu Ile Gln Phe Ala Pro Asn Ala Asp Val Lys
                370                 375                 380

Glu Lys Leu Thr Leu Leu Ser Lys Asp Lys Asp Gln Phe Ala Val Glu
385                 390                 395                 400

Ile Thr Ser Lys Tyr Phe Asn Ile Ala Asp Ala Leu Lys Tyr Leu Ser
                405                 410                 415

Asp Gly Ala Lys Trp Asp Thr Val Pro Met Gln Phe Leu Val Glu Ser
                420                 425                 430

Val Pro Gln Met Thr Pro Arg Tyr Tyr Ser Ile Ser Ser Ser Ser Leu
                435                 440                 445

Ser Glu Lys Gln Thr Val His Val Thr Ser Ile Val Glu Asn Phe Pro
450                 455                 460

Asn Pro Glu Leu Pro Asp Ala Pro Pro Val Val Gly Val Thr Thr Asn
465                 470                 475                 480

Leu Leu Arg Asn Ile Gln Leu Ala Gln Asn Asn Val Asn Ile Ala Glu
                485                 490                 495

Thr Asn Leu Pro Val His Tyr Asp Leu Asn Gly Pro Arg Lys Leu Phe
                500                 505                 510

Ala Asn Tyr Lys Leu Pro Val His Val Arg Arg Ser Asn Phe Arg Leu
                515                 520                 525

Pro Ser Asn Pro Ser Thr Pro Val Ile Met Ile Gly Pro Gly Thr Gly
                530                 535                 540

Val Ala Pro Phe Arg Gly Phe Ile Arg Glu Arg Val Ala Phe Leu Glu
545                 550                 555                 560

Ser Gln Lys Lys Gly Gly Asn Asn Val Ser Leu Gly Lys His Ile Leu
                565                 570                 575

Phe Tyr Gly Ser Arg Asn Thr Asp Asp Phe Leu Tyr Gln Asp Glu Trp
                580                 585                 590

Pro Glu Tyr Ala Lys Lys Leu Asp Gly Ser Phe Glu Met Val Val Ala
                595                 600                 605

His Ser Arg Leu Pro Asn Thr Lys Lys Val Tyr Val Gln Asp Lys Leu
                610                 615                 620

Lys Asp Tyr Glu Asp Gln Val Phe Glu Met Ile Asn Asn Gly Ala Phe
625                 630                 635                 640
```

```
Ile Tyr Val Cys Gly Asp Ala Lys Gly Met Ala Lys Gly Val Ser Thr
                645                 650                 655

Ala Leu Val Gly Ile Leu Ser Arg Gly Lys Ser Ile Thr Thr Asp Glu
            660                 665                 670

Ala Thr Glu Leu Ile Lys Met Leu Lys Thr Ser Gly Arg Tyr Gln Glu
        675                 680                 685

Asp Val Trp
    690

<210> SEQ ID NO 17
<211> LENGTH: 2136
<212> TYPE: DNA
<213> ORGANISM: Arabidopsis thaliana

<400> SEQUENCE: 17
atgtcctctt cttcttcttc gtcaacctcc atgatcgatc tcatggcagc aatcatcaaa      60
ggagagcctg taattgtctc cgacccagct aatgcctccg cttacgagtc cgtagctgct     120
gaattatcct ctatgcttat agagaatcgt caattcgcca tgattgttac cacttccatt     180
gctgttctta ttggttgcat cgttatgctc gtttggagga atccggttc tgggaattca      240 aaacgtgtcg agcctcttaa gcctttggtt attaagcctc gtgaggaaga gattgatgat     300
gggcgtaaga agttaccat cttttttcggt acacaaactg gtactgctga aggttttgca     360
aaggctttag gagaagaagc taaagcaaga tatgaaaaga ccagattcaa aatcgttgat     420
ttggatgatt acgcggctga tgatgatgag tatgaggaga aattgaagaa agaggatgtg     480
gctttcttct tcttagccac atatggagat ggtgagccta ccgacaatgc agcgagattc     540
tacaaatggt tcaccgaggg gaatgacaga ggagaatggc ttaagaactt gaagtatgga     600
gtgtttggat taggaaacag acaatatgag catttttaata aggttgccaa agttgtagat     660
gacattcttg tcgaacaagg tgcacagcgt cttgtacaag ttggtcttgg agatgatgac     720
cagtgtattg aagatgactt taccgcttgg cgagaagcat tgtggcccga gcttgataca     780
atactgaggg aagaagggga tacagctgtt gccacaccat acactgcagc tgtgttagaa     840
tacagagttt ctattcacga ctctgaagat gccaaattca atgatataaa catggcaaat     900
gggaatggtt acactgtgtt tgatgctcaa catccttaca agcaaatgt cgctgttaaa      960 agggagcttc atactcccga gtctgatcgt tcttgtatcc atttggaatt tgacattgct    1020
ggaagtggac ttacgtatga aactggagat catgttggtg tactttgtga taacttaagt    1080
gaaactgtag atgaagctct tagattgctg atatgtcac ctgatactta tttctcactt     1140
cacgctgaaa agaagacgg cacaccaatc agcagctcac tgcctcctcc cttcccacct    1200
tgcaacttga aacagcgct acacgatat gcatgtcttt tgagttctcc aaagaagtct     1260
gctttagttg cgttggctgc tcatgcatct gatcctaccg aagcagaacg attaaaacac    1320
cttgcttcac ctgctggaaa ggatgaatat tcaaagtggg tagtagagag tcaaagaagt    1380
ctacttgagg tgatggccga gtttccttca gccaagccac cacttggtgt cttcttcgct    1440
ggagttgctc caaggttgca gcctaggttc tattcgatat catcatcgcc caagattgct    1500
gaaactagaa ttcacgtcac atgtgcactg gtttatgaga aatgccaac tggcaggatt     1560 cataagggag tgtgttccac ttggatgaag aatgctgtgc cttacgagaa gagtgaaaac    1620
tgttcctcgg cgccgatatt tgttaggcaa tccaacttca gcttccttc tgattctaag    1680 gtaccgatca tcatgatcgg tccagggact ggattagctc cattcagagg attccttcag    1740
```

```
gaaagactag cgttggtaga atctggtgtt gaacttgggc catcagtttt gttctttgga   1800
tgcagaaacc gtagaatgga tttcatctac gaggaagagc tccagcgatt tgttgagagt   1860
ggtgctctcg cagagctaag tgtcgccttc tctcgtgaag acccaccaa agaatacgta    1920 cagcacaaga tgatggacaa ggcttctgat atctggaata tgatctctca aggagcttat   1980
ttatatgttt gtggtgacgc caaaggcatg gcaagagatg ttcacagatc tctccacaca   2040
atagctcaag aacaggggtc aatggattca actaaagcag agggcttcgt gaagaatctg   2100
caaacgagtg gaagatatct tagagatgta tggtaa                             2136

<210> SEQ ID NO 18
<211> LENGTH: 711
<212> TYPE: PRT
<213> ORGANISM: Arabidopsis thaliana

<400> SEQUENCE: 18

Met Ser Ser Ser Ser Ser Ser Thr Ser Met Ile Asp Leu Met Ala
1               5                   10                  15

Ala Ile Ile Lys Gly Glu Pro Val Ile Val Ser Asp Pro Ala Asn Ala
            20                  25                  30

Ser Ala Tyr Glu Ser Val Ala Ala Glu Leu Ser Ser Met Leu Ile Glu
        35                  40                  45

Asn Arg Gln Phe Ala Met Ile Val Thr Thr Ser Ile Ala Val Leu Ile
    50                  55                  60

Gly Cys Ile Val Met Leu Val Trp Arg Arg Ser Gly Ser Gly Asn Ser
65                  70                  75                  80

Lys Arg Val Glu Pro Leu Lys Pro Leu Val Ile Lys Pro Arg Glu Glu
                85                  90                  95

Glu Ile Asp Asp Gly Arg Lys Lys Val Thr Ile Phe Pro Gly Thr Gln
            100                 105                 110

Thr Gly Thr Ala Glu Gly Phe Ala Lys Ala Leu Gly Glu Glu Ala Lys
        115                 120                 125

Ala Arg Tyr Glu Lys Thr Arg Phe Lys Ile Val Asp Leu Asp Asp Tyr
    130                 135                 140

Ala Ala Asp Asp Asp Glu Tyr Glu Glu Lys Leu Lys Lys Glu Asp Val
145                 150                 155                 160

Ala Phe Phe Phe Leu Ala Thr Tyr Gly Asp Gly Glu Pro Thr Asp Asn
                165                 170                 175

Ala Ala Arg Phe Tyr Lys Trp Phe Thr Glu Gly Asn Asp Arg Gly Glu
            180                 185                 190

Trp Leu Lys Asn Leu Lys Tyr Gly Val Phe Gly Leu Gly Asn Arg Gln
        195                 200                 205

Tyr Glu His Phe Asn Lys Val Ala Lys Val Val Asp Asp Ile Leu Val
    210                 215                 220

Glu Gln Gly Ala Gln Arg Leu Val Gln Val Gly Leu Gly Asp Asp Asp
225                 230                 235                 240

Gln Cys Ile Glu Asp Asp Phe Thr Ala Trp Arg Glu Ala Leu Trp Pro
                245                 250                 255

Glu Leu Asp Thr Ile Leu Arg Glu Glu Gly Asp Thr Ala Val Ala Thr
            260                 265                 270

Pro Tyr Thr Ala Ala Val Leu Glu Tyr Arg Val Ser Ile His Asp Ser
        275                 280                 285

Glu Asp Ala Lys Phe Asn Asp Ile Asn Met Ala Asn Gly Asn Gly Tyr
    290                 295                 300
```

-continued

```
Thr Val Phe Asp Ala Gln His Pro Tyr Lys Ala Asn Val Ala Val Lys
305                 310                 315                 320

Arg Glu Leu His Thr Pro Glu Ser Asp Arg Ser Cys Ile His Leu Glu
            325                 330                 335

Phe Asp Ile Ala Gly Ser Gly Leu Thr Tyr Glu Thr Gly Asp His Val
        340                 345                 350

Gly Val Leu Cys Asp Asn Leu Ser Glu Thr Val Asp Glu Ala Leu Arg
    355                 360                 365

Leu Leu Asp Met Ser Pro Asp Thr Tyr Phe Ser Leu His Ala Glu Lys
370                 375                 380

Glu Asp Gly Thr Pro Ile Ser Ser Ser Leu Pro Pro Phe Pro Pro
385                 390                 395                 400

Cys Asn Leu Arg Thr Ala Leu Thr Arg Tyr Ala Cys Leu Leu Ser Ser
            405                 410                 415

Pro Lys Lys Ser Ala Leu Val Ala Leu Ala Ala His Ala Ser Asp Pro
        420                 425                 430

Thr Glu Ala Glu Arg Leu Lys His Leu Ala Ser Pro Ala Gly Lys Asp
    435                 440                 445

Glu Tyr Ser Lys Trp Val Val Glu Ser Gln Arg Ser Leu Leu Glu Val
450                 455                 460

Met Ala Glu Phe Pro Ser Ala Lys Pro Pro Leu Gly Val Phe Phe Ala
465                 470                 475                 480

Gly Val Ala Pro Arg Leu Gln Pro Arg Phe Tyr Ser Ile Ser Ser Ser
            485                 490                 495

Pro Lys Ile Ala Glu Thr Arg Ile His Val Thr Cys Ala Leu Val Tyr
        500                 505                 510

Glu Lys Met Pro Thr Gly Arg Ile His Lys Gly Val Cys Ser Thr Trp
    515                 520                 525

Met Lys Asn Ala Val Pro Tyr Glu Lys Ser Glu Asn Cys Ser Ser Ala
530                 535                 540

Pro Ile Phe Val Arg Gln Ser Asn Phe Lys Leu Pro Ser Asp Ser Lys
545                 550                 555                 560

Val Pro Ile Ile Met Ile Gly Pro Gly Thr Gly Leu Ala Pro Phe Arg
            565                 570                 575

Gly Phe Leu Gln Glu Arg Leu Ala Leu Val Glu Ser Gly Val Glu Leu
        580                 585                 590

Gly Pro Ser Val Leu Phe Phe Gly Cys Arg Asn Arg Met Asp Phe
    595                 600                 605

Ile Tyr Glu Glu Glu Leu Gln Arg Phe Val Glu Ser Gly Ala Leu Ala
610                 615                 620

Glu Leu Ser Val Ala Phe Ser Arg Glu Gly Pro Thr Lys Glu Tyr Val
625                 630                 635                 640

Gln His Lys Met Met Asp Lys Ala Ser Asp Ile Trp Asn Met Ile Ser
            645                 650                 655

Gln Gly Ala Tyr Leu Tyr Val Cys Gly Asp Ala Lys Gly Met Ala Arg
        660                 665                 670

Asp Val His Arg Ser Leu His Thr Ile Ala Gln Glu Gln Gly Ser Met
    675                 680                 685

Asp Ser Thr Lys Ala Glu Gly Phe Val Lys Asn Leu Gln Thr Ser Gly
690                 695                 700

Arg Tyr Leu Arg Asp Val Trp
705                 710
```

```
<210> SEQ ID NO 19
<211> LENGTH: 33
<212> TYPE: DNA
<213> ORGANISM: Arabidopsis thaliana

<400> SEQUENCE: 19
cggaattctc atggatcaaa tcgaagcaat gtt                          33

<210> SEQ ID NO 20
<211> LENGTH: 29
<212> TYPE: DNA
<213> ORGANISM: Arabidopsis thaliana

<400> SEQUENCE: 20
cgactagttt agcaaatcgg aatcggagc                               29

<210> SEQ ID NO 21
<211> LENGTH: 30
<212> TYPE: DNA
<213> ORGANISM: Arabidopsis thaliana

<400> SEQUENCE: 21
cgctcgagat atggacctcc tcttgctgga                              30

<210> SEQ ID NO 22
<211> LENGTH: 32
<212> TYPE: DNA
<213> ORGANISM: Arabidopsis thaliana

<400> SEQUENCE: 22
cgggtacctt aacagttcct tggtttcata ac                           32

<210> SEQ ID NO 23
<211> LENGTH: 36
<212> TYPE: DNA
<213> ORGANISM: Arabidopsis thaliana

<400> SEQUENCE: 23
gctctagacc tatggcgcca caagaacaag cagttt                       36

<210> SEQ ID NO 24
<211> LENGTH: 36
<212> TYPE: DNA
<213> ORGANISM: Arabidopsis thaliana

<400> SEQUENCE: 24
gcggatcccc ttcacaatcc atttgctagt tttgcc                       36

<210> SEQ ID NO 25
<211> LENGTH: 31
<212> TYPE: DNA
<213> ORGANISM: Rheum tataricum

<400> SEQUENCE: 25
ccggatccaa atggccccag aagagagcag g                            31

<210> SEQ ID NO 26
<211> LENGTH: 35
<212> TYPE: DNA
<213> ORGANISM: Rheum tataricum

<400> SEQUENCE: 26
cgctcgagtt aagtgatcaa tggaaccgaa gacag                        35
```

```
<210> SEQ ID NO 27
<211> LENGTH: 38
<212> TYPE: DNA
<213> ORGANISM: Rhodobacter capsulatus

<400> SEQUENCE: 27
ccgaattccc atgaccctgc aatctcaaac agctaaag                              38

<210> SEQ ID NO 28
<211> LENGTH: 30
<212> TYPE: DNA
<213> ORGANISM: Rhodobacter capsulatus

<400> SEQUENCE: 28
ccactagttt aagcaggtgg atcggcagct                                       30

<210> SEQ ID NO 29
<211> LENGTH: 37
<212> TYPE: DNA
<213> ORGANISM: Saccharomyces cerevisiae

<400> SEQUENCE: 29
ccctcgagat catgccgttt ggaatagaca acaccga                               37

<210> SEQ ID NO 30
<211> LENGTH: 36
<212> TYPE: DNA
<213> ORGANISM: Saccharomyces cerevisiae

<400> SEQUENCE: 30
ccaagcttat cgggctgatt accagacatc ttcttg                                36

<210> SEQ ID NO 31
<211> LENGTH: 36
<212> TYPE: DNA
<213> ORGANISM: Arabidopsis thaliana

<400> SEQUENCE: 31
ccggatcccc atgtcctctt cttcttcttc gtcaac                                36

<210> SEQ ID NO 32
<211> LENGTH: 34
<212> TYPE: DNA
<213> ORGANISM: Arabidopsis thaliana

<400> SEQUENCE: 32
ccctcgaggt gagtgtgtgg cttcaatagt ttcg                                  34

<210> SEQ ID NO 33
<211> LENGTH: 40
<212> TYPE: DNA
<213> ORGANISM: Rhodobacter capsulatus

<400> SEQUENCE: 33
ccgctcgagc ggatgaccct gcaatctcaa acagctaaag                            40

<210> SEQ ID NO 34
<211> LENGTH: 30
<212> TYPE: DNA
<213> ORGANISM: Rhodobacter capsulatus

<400> SEQUENCE: 34
gcggatcctt aagcaggtgg atcggcagct                                       30
```

```
<210> SEQ ID NO 35
<211> LENGTH: 35
<212> TYPE: DNA
<213> ORGANISM: Arabidopsis thaliana

<400> SEQUENCE: 35
tgccatggca atggcgccac aagaacaagc agttt                              35

<210> SEQ ID NO 36
<211> LENGTH: 36
<212> TYPE: DNA
<213> ORGANISM: Arabidopsis thaliana

<400> SEQUENCE: 36
gcggatcccc ttcacaatcc atttgctagt tttgcc                             36

<210> SEQ ID NO 37
<211> LENGTH: 37
<212> TYPE: DNA
<213> ORGANISM: Arabidopsis thaliana

<400> SEQUENCE: 37
ttgcggccgc aaatctcgat cccgcgaaat taatacg                            37

<210> SEQ ID NO 38
<211> LENGTH: 36
<212> TYPE: DNA
<213> ORGANISM: Arabidopsis thaliana

<400> SEQUENCE: 38
cgctcgagcc ttcacaatcc atttgctagt tttgcc                             36
```

METABOLICALLY ENGINEERED CELLS FOR THE PRODUCTION OF RESVERATROL OR AN OLIGOMERIC OR GLYCOSIDICALLY-BOUND DERIVATIVE THEREOF

FIELD OF THE INVENTION

This invention relates generally to the production of the polyphenol resveratrol or an oligomeric or glycosidically bound derivative thereof such as its β-glucoside piceid using microbial cells. Furthermore, it relates to the use of naturally occurring or recombinant micro-organisms that produce resveratrol or such a derivative for production of food, feed and beverages.

BACKGROUND OF THE INVENTION

Production of chemicals from micro-organisms has been an important application of biotechnology. Typically, the steps in developing such a bio-production method may include 1) selection of a proper micro-organism host, 2) elimination of metabolic pathways leading to by-products, 3) deregulation of desired pathways at both enzyme activity level and the transcriptional level, and 4) overexpression of appropriate enzymes in the desired pathways. In preferred aspect, the present invention has employed combinations of the steps above to redirect carbon flow from phenylalanine or tyrosine through enzymes of the plant phenylpropanoid pathway which supplies the necessary precursor for the desired biosynthesis of resveratrol.

Resveratrol (or 3,4,5-trihydroxystilbene) is a phytophenol belonging to the group of stilbene phytoalexins, which are low-molecular-mass secondary metabolites that constitute the active defense mechanism in plants in response to infections or other stress-related events. Stilbene phytoalexins contain the stilbene skeleton (trans-1,2-diphenylethylene) as their common basic structure: that may be supplemented by addition of other groups as well (Hart and Shrimpton, 1979, Hart, 1981). Stilbenes have been found in certain trees (angiosperms, gymnosperms), but also in some herbaceous plants (in species of the Myrtaceae, Vitaceae and Leguminosae families). Said compounds are toxic to pests, especially to fungi, bacteria and insects. Only few plants have the ability to synthesize stilbenes, or to produce them in an amount that provides them sufficient resistance to pests.

The synthesis of the basic stilbene skeleton is pursued by stilbene synthases. So far, two enzymes have been designated as a stilbene synthase; pinosylvine synthase and resveratrol synthase. To date, the groundnut (*Arachis hypogaea*) resveratrol synthase has been characterised in most detail, such that most of the properties are known (Schoppner and Kindl, 1984). Substrates that are used by stilbene synthases are malonyl-CoA, cinnamoyl-CoA or coumaroyl-CoA. These substances occur in every plant because they are used in the biosynthesis of other important plant constituents as well such as flavonoids, flower pigments and lipids.

Resveratrol (FIG. 1 trans-form) consists of two closely connected phenol rings and belongs therefore to the polyphenols. While present in other plants, such as eucalyptus, spruce, and lily, and in other foods such as mulberries and peanuts, resveratrol's most abundant natural sources are *Vitis vinifera*, *-labrusca*, and *-muscadine* (*rotundifolia*) grapes, which are used to make wines. The compound occurs in the vines, roots, seeds, and stalks, but its highest concentration is in the skin (Celotti et al., 1996), which contains 50-100 µg/g. (Jang et al. 1997). During red wine vinification the grape skins are included in the must, in contrast to white wine vinification, and therefore resveratrol is found in small quantities in red wine only. Resveratrol has, besides its antifungal properties, been recognized for its cardioprotective- and cancer chemopreventive activities; it acts as a phytoestrogen, an inhibitor of platelet aggregation (Kopp et al, 1998; Gehm et al 1997; Lobo et al 1995), and an antioxidant (Jang et al., 1997; Huang 1997). These properties explain the so-called French Paradox, i.e. the wine-drinking French have a low incidence of coronary heart disease despite a low-exercise, high-fat diet. Recently it has been shown that resveratrol can also activate the SIR2 gene in yeast and the analogous human gene SIRT1, which both play a key role in extending life span. Ever since, attention is very much focused on the life-span extending properties of resveratrol (Hall, 2003, Couzin, 2004).

American health associations, such as the Life Extension Foundation, are promoting the vast beneficial effects of this drug, and thereby propelling the ideal conditions for a successful commercialisation. Present production processes rely mostly upon extraction of resveratrol, either from the skin of grape berries, or from Knot weed. This is a labour intensive process and generates low yield which, therefore, prompts an incentive for the development of novel, more efficient and high-yielding production processes.

In plants, the phenylpropanoid pathway is responsible for the synthesis of a wide variety of secondary metabolic compounds, including lignins, salicylates, coumarins, hydroxycinnamic amides, pigments, flavonoids and phytoalexins. Indeed formation of resveratrol in plants proceeds through the phenylpropanoid pathway. The amino acid L-phenylalanine is converted into trans-cinnamic acid through the non-oxidative deamination by L-phenylalanine ammonia lyase (PAL) (FIG. 2). Next, trans-cinnamic acid is hydroxylated at the para-position to 4-coumaric acid (4-hydroxycinnamic acid) by cinnamate-4-hydroxylase (C4H), a cytochrome P450 monooxygenase enzyme, in conjunction with NADPH: cytochrome P450 reductase (CPR). The 4-coumaric acid, is subsequently activated to 4-coumaroyl-CoA by the action of 4-coumarate-CoA ligase (4CL). Finally, resveratrol synthase (VST) catalyses the condensation of a phenylpropane unit of 4-coumaroyl-CoA with malonyl CoA, resulting in formation of resveratrol.

Recently, a yeast was disclosed that could produce resveratrol from 4-coumaric acid that is found in small quantities in grape must (Becker et al. 2003). The production of 4-coumaroyl-CoA, and concomitant resveratrol, in laboratory strains of *S. cerevisiae*, was achieved by co-expressing a heterologous coenzyme-A ligase gene, from hybrid poplar, together with the grapevine resveratrol synthase gene (vst1). The other substrate for resveratrol synthase, malonyl-CoA, is already endogenously produced in yeast and is involved in de novo fatty-acid biosynthesis. The study showed that cells of *S. cerevisiae* could produce minute amounts of resveratrol, either in the free form or in the glucoside-bound form, when cultured in synthetic media that was supplemented with 4-coumaric acid.

However, said yeast would not be suitable for a commercial application because it suffers from low resveratrol yield, and requires addition of 4-coumaric acid, which is only present in few industrial media. In order to facilitate and broaden the application of resveratrol as both a pharmaceutical and neutraceutical, it is therefore highly desirable to obtain a yeast that can produce resveratrol directly from glucose, without addition of 4-coumaric acid.

A recent study (Ro and Douglas, 2004) describes the reconstitution of the entry point of the phenylpropanoid pathway in *S. cerevisiae* by introducing PAL, C4H and CPR from Poplar. The purpose was to evaluate whether multienzyme complexes (MECs) containing PAL and C4H are functionally important at this entry point into phenylpropanoid metabolism. By feeding the recombinant yeast with [3H]-phenylalanine it was found that the majority of metabolized [3H]-phenylalanine was incorporated into 4-[3H]-coumaric acid, and that phenylalanine metabolism was highly reduced by inhibiting C4H activity. Moreover, PAL-alone expressers metabolized very little phenylalanine into cinnamic acid. When feeding [3H]-phenylalanine and [14C]-trans-cinnamic acid simultaneously to the triple expressers, no evidence was found for channeling of the endogenously synthesized [3H]-trans-cinnamic acid into 4-coumaric acid. Therefore, efficient carbon flux from phenylalanine to 4-coumaric acid via reactions catalyzed by PAL and C4H does not appear to require channeling through a MEC in yeast, and sheer biochemical coupling of PAL and C4H seems to be sufficient to drive carbon flux into the phenylpropanoid pathway. In yet another study (Hwang et al., 2003) production of plant-specific flavanones by *Escherichia coli* was achieved through expression of an artificial gene cluster that contained three genes of a phenyl propanoid pathway of various heterologous origins; PAL from the yeast *Rhodotorula rubra*, 4CL from the actinomycete *Streptomyces coelicolor*, and chalcone synthase (CHS) from the licorice plant *Glycyrrhiza echinata*. These pathways bypassed C4H, because the bacterial 4CL enzyme ligated coenzyme A to both trans-cinnamic acid and 4-coumaric acid. In addition, the PAL from *Rhodotorula rubra* uses both phenylalanine and tyrosine as the substrates. Therefore, *E. coli* cells containing the gene clusters and grown on glucose, produced small amounts of two flavanones, pinocembrin (0.29 g/l) from phenylalanine and naringenin (0.17 g/l) from tyrosine. In addition, large amounts of their precursors, 4-coumaric acid and trans-cinnamic acid (0.47 and 1.23 mg/liter respectively), were acumulated. Moreover, the yields of these compounds could be increased by addition of phenylalanine and tyrosine.

Whereas the enzyme from dicotylic plants utilizes only phenylalanine efficiently, several studies indicated that PAL from monocotylic plants, and some micro-organisms, utilizes tyrosine as well (Rösler et al., 1997). In such reactions the enzyme activity is designated tyrosine ammonia lyase (TAL, FIG. 3). Conversion of tyrosine by TAL results in the direct formation of 4-coumaric acid without the intermediacy of C4H and CPR. Mostly both activities reside on the same polypeptide and have very similar catalytic efficiencies, in spite of large differences in Km and turnover number. However, most PAL/TAL enzymes from plants prefer phenylalanine rather than tyrosine. The level of TAL activity is mostly lower than PAL activity, but the magnitude of this difference varies over a wide range. For example, the parsley enzyme has a Km for phenylalanine of 15-25 µM and for tyrosine 2.0-8.0 mM with turnover numbers 22 $s^{-1}$ and 0.3 $s^{-1}$ respectively. In contrast, the maize enzyme has a Km for phenylalanine only 15-fold higher than for tyrosine, and turnover numbers about 10-fold higher. Moreover, in the red yeasts, *Rhodotorula glutinis* (*Rhodosporidium toruloides*) and -*rubra*, the TAL catalytic activity is close to the PAL catalytic activity with a ratio of TAL/PAL of approximately 0.58. It is believed that the PAL enzyme in these yeasts degrades phenylalanine as a catabolic function and the trans-cinnamic acid formed is converted to benzoate and other cellular materials, whereas in plants it is thought to be merely a regulatory enzyme in the biosynthesis of lignin, isoflavonoids and other phenylpropanoids.

Recently, an open reading frame was found in the bacterium *Rhodobacter capsulatus* that encodes a hypothetical biosynthetic tyrosine ammonia lyase (TAL) that is involved in the biosynthesis of the chromophore of the photoactive yellow protein (Kyndt et al., 2002). This was the first time that a PAL-homologous gene was found in bacteria. The TAL gene was isolated and overproduced in *Escherichia coli*. The Km and kcat values for the conversion of tyrosine to 4-coumaric acid were 15.6 µM and 27.7 $s^{-1}$ respectively, and for conversion of L-phenylalanine to trans-cinnamic acid were 1277 µM and 15.1 $s^{-1}$ respectively. As a consequence of the smaller Km and a slightly larger kcat, the enzyme shows a strong preference for tyrosine over L-phenylalanine, with a catalytic efficiency (Km/kcat) for tyrosine of approximately 150-fold larger than for phenylalanine. The kinetic studies established that tyrosine, and not L-phenylalanine, is the natural substrate of the enzyme under physiological conditions. Very recently a study described the heterologous coexpression of phenylalanine ammonia lyase, cinnamate-4-hydroxylase, 4-coumarate-Coa-ligase and chalcone synthase, for the production of flavonoids in *E. coli* (Watts et al., 2004). The simultaneous expression of all four genes, however, was not successful because of a nonfunctional cinnamate-4-hydroxylase. The substitution of phenylalanine ammonia lyase and cinnamate-4-hydroxylase by a new tyrosine ammonia lyase that was cloned from *Rhodobacter sphaeroides*, could, however, solved the problem and led to high-level production of the flavonone naringenin. Furthermore, said tyrosine ammonia lyase from *Rhodobacter sphaeroides* is also used for heterologous production of 4-coumaric acid (i.e. para-hydroxycinnamic acid) in *Escherichia coli* (US-A-2004059103). Evenmore, further methods for development of a biocatalyst for conversion of glucose into 4-coumaric acid are described. US-A-2004023357 discloses a tyrosine ammonia lyase from the yeast *Trichosporon cutaneum* for the production of coumaric acid in *Escherichia coli* and *Saccharomyces cerevisiae*. US-A-2001053847 describes the incorporation of the wild type PAL from the yeast *Rhodotorula glutinis* into *E. coli*, underlining the ability of the wildtype PAL to convert tyrosine directly to 4-coumaric acid. Moreover, there is also exemplification of incorporation of the wildtype PAL from the yeast *Rhodotorula glutinis*, plus a plant C4H and CPR into *E. coli* and *S. cerevisiae*. Also described is the development of a biocatalyst through mutagenesis of the wild type yeast PAL *Rhodotorula glutinis* with enhanced TAL activity (US-A-6521748). Neither of the aforementioned patents claim the incorporation of 4CL and VST for the production of resveratrol.

Recently, evidence was shown that the filamentous fungi *A. oryzae* contained the enzyme chalcone synthase (CHS) that is normally involved in the biosynthesis of flavonoids, such as naringenin, in plants (Seshime et al., 2005). Indeed it was also shown that *A. oryzae* contained the major set of genes responsible for phenylpropanoid-flavonoid metabolism, i.e PAL, C4H and 4CL. However, there is no evidence that *A. oryzae* contained a stilbene synthase such as resveratrol synthase.

The present invention now provides a micro-organism having an operative metabolic pathway comprising at least one enzyme activity, said pathway producing 4-coumaric acid and producing resveratrol therefrom or an oligomeric or glycosidically-bound derivative thereof. Such a micro-organism may be naturally occurring and may be isolated by suitable screening procedures, but more preferably is genetically engineered.

Preferably, said resveratrol or derivative is produced in a reaction catalysed by an enzyme in which endogenous malonyl-CoA is a substrate, and preferably said resveratrol is produced from 4-coumaroyl-CoA.

Said resveratrol or derivative is preferably produced from 4-coumaroyl-CoA by a resveratrol synthase which is preferably expressed in said micro-organism from nucleic acid coding for said enzyme which is not native to the micro-organism.

Generally herein, unless the context implies otherwise, references to resveratrol include reference to oligomeric or glycosidically bound derivatives thereof, including particularly piceid.

Thus, in certain preferred embodiments, said resveratrol synthase is a resveratrol synthase (EC 2.3.1.95) from a plant belonging to the genus of *Arachis*, e.g. *A. glabatra, A. hypogaea*, a plant belonging to the genus of *Rheum*, e.g. *R. tataricum*, a plant belonging to the genus of *Vitus*, e.g. *V. labrusca, V. riparaia, V. vinifera*, or any one of the genera *Pinus, Piceea, Lilium, Eucalyptus, Parthenocissus, Cissus, Calochortus, Polygonum, Gnetum, Artocarpus, Nothofagus, Phoenix, Festuca, Carex, Veratrum, Bauhinia* or *Pterolobium*.

Preferably, said 4-coumaric acid is produced from trans-cinnamic acid, suitably by an enzyme in a reaction catalysed by said enzyme in which oxygen is a substrate, NADH or NADPH is a cofactor and $NAD^+$ or $NADP^+$ is a product.

Thus, said 4-coumaric acid may be produced from trans-cinnamic acid by a cinnamate 4-hydroxylase, which preferably is expressed in said micro-organism from nucleic acid coding for said enzyme which is not native to the micro-organism.

In certain preferred embodiments, including those referred to in the paragraphs above, said cinnamate-4-hydroxylase is a cinnamate-4-hydroxylase (EC 1.14.13.11) from a plant or a micro-organism. The plant may belong to the genus of *Arabidopsis*, e.g. *A. thaliana*, a plant belonging to the genus of *Citrus*, e.g. *C. sinensis, C.×paradisi*, a plant belonging to the genus of *Phaseolus*, e.g. *P. vulgaris*, a plant belonging to the genus of *Pinus*, e.g. *P. taeda*, a plant belonging to the genus of *Populus*, e.g. *P. deltoides, P. tremuloides, P. trichocarpa*, a plant belonging to the genus of *Solanum*, e.g. *S. tuberosum*, a plant belonging to the genus of *Vitus*, e.g. *Vitus vinifera*, a plant belonging to the genus of *Zea*, e.g. *Z. mays*, or other plant genera e.g. *Ammi, Avicennia, Camellia, Camptotheca, Catharanthus, Glycine, Helianthus, Lotus, Mesembryanthemum, Physcomitrella, Ruta, Saccharum, Vigna*. The micro-organism might be a fungus belonging to the genus *Aspergillus*, e.g. *A. oryzae*.

Preferably, said 4-coumaric acid is produced from tyrosine in a reaction catalysed by an enzyme in which ammonia is produced and suitably, said 4-coumaric acid is produced from tyrosine by a L-phenylalanine ammonia lyase or a tyrosine ammonia lyase, e.g. tyrosine ammonia lyase (EC 4.3.1.5) from yeast or bacteria. Suitably, the tyrosine ammonia lyase is from the yeast *Rhodotorula rubra* or from the bacterium *Rhodobacter capsulatus*.

Optionally, said tyrosine ammonia lyase is expressed in said micro-organism from nucleic acid coding for said enzyme which is not native to the micro-organism.

Alternatively, said trans-cinnamic acid may be produced from L-phenylalanine in a reaction catalysed by an enzyme in which ammonia is produced and suitably said trans-cinnamic acid is formed from L-phenylalanine by a phenylalanine ammonia lyase.

In certain preferred embodiments, said L-phenylalanine ammonia lyase is a L-phenylalanine ammonia lyase (EC 4.3.1.5) from a plant or a micro-organism. The plant may belong to the genus of *Arabidopsis*, e.g. *A. thaliana*, a plant belonging to the genus of *Brassica*, e.g. *B. napus, B. rapa*, a plant belonging to the genus of Citrus, e.g. *C. reticulata, C. clementinus, C. limon*, a plant belonging to the genus of *Phaseolus*, e.g. *P. coccineus, P. vulgaris*, a plant belonging to the genus of *Pinus*, e.g. *P. banksiana, P. monticola, P. pinaster, P. sylvestris, P. taeda*, a plant belonging to the genus of *Populus*, e.g. *P. balsamifera, P. deltoides, P. Canadensis, P. kitakamiensis, P. tremuloides*, a plant belonging to the genus of *Solanum*, e.g. *S. tuberosum*, a plant belonging to the genus of *Prunus*, e.g. *P. avium, P. persica*, a plant belonging to the genus of *Vitus*, e.g. *Vitus vinifera*, a plant belonging to the genus of *Zea*, e.g. *Z. mays* or other plant genera e.g. *Agastache, Ananas, Asparagus, Bromheadia, Bambusa, Beta, Betula, Cucumis, Camellia, Capsicum, Cassia, Catharanthus, Cicer, Citrullus, Coffea, Cucurbita, Cynodon, Daucus, Dendrobium, Dianthus, Digitalis, Dioscorea, Eucalyptus, Gallus, Ginkgo, Glycine, Hordeum, Helianthus, Ipomoea, Lactuca, Lithospermum, Lotus, Lycopersicon, Medicago, Malus, Manihot, Medicago, Mesembryanthemum, Nicotiana, Olea, Oryza, Pisum, Persea, Petroselinum, Phalaenopsis, Phyllostachys, Physcomitrella, Picea, Pyrus, Quercus, Raphanus, Rehmannia, Rubus, Sorghum, Sphenostylis, Stellaria, Stylosanthes, Triticum, Trifolium, Triticum, Vaccinium, Vigna, Zinnia*. The micro-organism might be a fungus belonging to the genus *Agaricus*, e.g. *A. bisporus*, a fungus belonging to the genus *Aspergillus*, e.g. *A. oryzae, A. nidulans, A. fumigatus*, a fungus belonging to the genus *Ustilago*, e.g. *U. maydis*, a bacterium belonging to the genus *Rhodobacter*, e.g. *R. capsulatus*, a yeast belonging to the genus *Rhodotorula*, e.g. *R. rubra*.

Suitably, said L-phenylalanine ammonia lyase is expressed in said micro-organism from nucleic acid coding for said enzyme which is not native to the micro-organism.

Preferably, 4-coumaroyl-CoA is formed in a reaction catalysed by an enzyme in which ATP and CoA are substrates and ADP is a product and suitably 4-coumaroyl-CoA is formed in a reaction catalysed by a 4-coumarate-CoA ligase.

Said 4-coumarate-CoA ligase may be a 4-coumarate-CoA ligase (EC 6.2.1.12) from a plant, a micro-organism or a nematode. The plant may belong to the genus of *Abies*, e.g. *A. beshanzuensis, B. firma, B. holophylla*, a plant belonging to the genus of *Arabidopsis*, e.g. *A. thaliana*, a plant belonging to the genus of *Brassica*, e.g. *B. napus, B. rapa, B. oleracea*, a plant belonging to the genus of Citrus, e.g. *C. sinensis*, a plant belonging to the genus of *Larix*, e.g. *L. decidua, L. gmelinii, L. griffithiana, L. himalaica, L. kaempferi, L. laricina, L. mastersiana, L. occidentalis, L. potaninii, L. sibirica, L. speciosa*, a plant belonging to the genus of *Phaseolus*, e.g. *P. acutifolius, P. coccineus*, a plant belonging to the genus of *Pinus*, e.g. *P. armandii P. banksiana, P. pinaster*, a plant belonging to the genus of *Populus*, e.g. *P. balsamifera, P. tomentosa, P. tremuloides*, a plant belonging to the genus of *Solanum*, e.g. *S. tuberosum*, a plant belonging to the genus of *Vitus*, e.g. *Vitus vinifera*, a plant belonging to the genus of *Zea*, e.g. *Z. mays*, or other plant genera e.g. *Agastache, Amorpha, Cathaya, Cedrus, Crocus, Festuca, Glycine, Juglans, Keteleeria, Lithospermum, Lolium, Lotus, Lycopersicon, Malus, Medicago, Mesembryanthemum, Nicotiana, Nothotsuga, Oryza, Pelargonium, Petroselinum, Physcomitrella, Picea, Prunus, Pseudolarix, Pseudotsuga, Rosa, Rubus, Ryza, Saccharum, Suaeda, Thellungiella, Triticum, Tsuga*. The micro-organism might be a filamentous fungi belonging to the genus *Aspergillus*, e.g. *A. flavus, A. nidulans, A. oryzae, A. fumigatus*, a filamentous fungus belonging to the genus *Neurospora*, e.g. *N. crassa*, a fungus belonging to the genus *Yarrowia*, e.g. *Y. lipolytica*, a fungus belonging to the genus of *Mycosphaerella*, e.g. *M. graminicola*, a bacterium belonging to the genus of *Mycobacterium*, e.g. *M. bovis, M. leprae, M. tuberculosis*, a bacterium belonging to the genus of *Neisseria*, e.g. *N. meningitidis*, a bacterium belonging to the genus of *Streptomyces*, e.g. *S. coelicolor*, a bacterium belonging to the genus of *Rhodobacter*, e.g. *R. capsulatus*, a nematode belonging to the genus *Ancylostoma*, e.g. *A. ceylanicum*, a nematode belonging to the genus *Caenorhabditis*, e.g. *C. elegans*, a nematode belonging to the genus *Haemonchus*, e.g. *H. contortus*, a nematode belonging to the genus *Lumbricus*, e.g. *L. rubellus*, a nematode belonging to the genus *Meilodogyne*, e.g. *M. hapla*, a nematode belonging to the genus *Strongyloidus*, e.g. *S. rattii, S. stercoralis*, a nematode belonging to the genus *Pristionchus*, e.g. *P. pacificus*.

Optionally, a NADPH:cytochrome P450 reductase (CPR) has been recombinantly introduced into said micro-organism. This may be a plant CPR introduced into a non-plant micro-organism. Alternatively, a native NADPH:cytochrome P450 reductase (CPR) has been overexpressed in said micro-organism.

In certain preferred embodiments, including those referred to in the paragraphs above, said NADPH:cytochrome P450 reductase is a NADPH:cytochrome P450 reductase (EC 1.6.2.4) from a plant belonging to the genus of *Arabidopsis*, e.g. *A. thaliana*, a plant belonging to the genus of Citrus, e.g. *C. sinensis, C.×paradisi*, a plant belonging to the genus of *Phaseolus*, e.g. *P. vulgaris*, a plant belonging to the genus of *Pinus*, e.g. *P. taeda*, a plant belonging to the genus of *Populus*, e.g. *P. deltoides, P. tremuloides, P. trichocarpa*, a plant belonging to the genus of *Solanum*, e.g. *S. tuberosum*, a plant belonging to the genus of *Vitus*, e.g. *Vitus vinifera*, a plant belonging to the genus of *Zea*, e.g. *Z. mays*, or other plant genera e.g. *Ammi, Avicennia, Camellia, Camptotheca, Catharanthus, Glycine, Helianthus, Lotus, Mesembryanthemum, Physcomitrella, Ruta, Saccharum, Vigna*.

Whilst the micro-organism may be naturally occurring, preferably at least one copy of at least one genetic sequence encoding a respective enzyme in said metabolic pathway has been recombinantly introduced into said micro-organism.

Additionally or alternatively to introducing coding sequences coding for a said enzyme, one may provide one or more expression signals, such as promoter sequences, not natively associated with said coding sequence in said organism. Thus, optionally, at least one copy of a genetic sequence encoding a tyrosine ammonia lyase is operatively linked to an expression signal not natively associated with said genetic sequence in said organism, and/or at least one copy of a genetic sequence encoding a L-phenylalanine ammonia lyase is operatively linked to an expression signal not natively associated with said genetic sequence in said organism.

Optionally, at least one copy of a genetic sequence encoding cinnamate 4-hydroxylase, whether native or not, is operatively linked to an expression signal not natively associated with said genetic sequence in said organism.

Optionally, at least one copy of a genetic sequence encoding a 4-coumarate-CoA ligase, whether native or not, is operatively linked to an expression signal not natively associated with said genetic sequence in said organism.

Optionally, at least one copy of a genetic sequence encoding a resveratrol synthase, whether native or not, is operatively linked to an expression signal not natively associated with said genetic sequence in said organism.

Expression signals include nucleotide sequences located upstream (5' non-coding sequences), within, or downstream (3' non-coding sequences) of a coding sequence, and which influence the transcription, RNA processing or stability, or translation of the associated coding sequence. Such sequences may include promoters, translation leader sequences, introns, and polyadenylation recognition sequences.

In certain aspects the invention provides a metabolically engineered micro-organism having an operative metabolic pathway in which a first metabolite is transformed into a second metabolite in a reaction catalysed by a first enzyme, said reaction step producing ammonia, and in which said second metabolite is transformed into a third metabolite in a reaction catalysed by a second enzyme, in which oxygen is a substrate, NADPH or NADH is a cofactor and $NADP^+$ or $NAD^+$ is a product, and in which said third metabolite is transformed into a fourth metabolite in a reaction catalysed by a third enzyme in which ATP and CoA is a substrate, and ADP is a product, and in which said fourth metabolite is transformed into a fifth metabolite in a reaction catalysed by a fourth enzyme in which endogenous malonyl-CoA is a substrate.

The present invention also provides a metabolically engineered micro-organism having an operative metabolic pathway in which a first metabolite is transformed into a said third metabolite catalysed by a first enzyme, said reaction step producing ammonia, without the involvement of said second enzyme, and in which said third metabolite is transformed into a said fourth metabolite in a reaction catalysed by a said third enzyme in which ATP and CoA is a substrate, and ADP is a product, and in which said fourth metabolite is transformed into a said fifth metabolite in a reaction catalysed by a said fourth enzyme in which endogenous malonyl-CoA is a substrate.

The micro-organisms described above include ones containing one or more copies of an heterologous DNA sequence encoding phenylalanine ammonia lyase operatively associated with an expression signal, and containing one or more copies of an heterologous DNA sequence encoding cinnamate-4-hydroxylase operatively associated with an expression signal, and containing one or more copies of an heterologous DNA sequence encoding 4-coumarate-CoA-ligase operatively associated with an expression signal, and containing one or more copies of an heterologous DNA sequence encoding resveratrol synthase operatively associated with an expression signal.

They include also ones lacking cinnamate-4-hydroxylase activity, and containing one or more copies of a heterologous DNA sequence encoding tyrosine ammonia lyase operatively associated with an expression signal, and containing one or more copies of an heterologous DNA sequence encoding 4-coumarate-CoA-ligase operatively associated with an expression signal, and containing one or more copies of an heterologous DNA sequence encoding resveratrol synthase operatively associated with an expression signal.

In the present context the term "micro-organism" relates to microscopic organisms, including bacteria, microscopic fungi, including yeast.

More specifically, the micro-organism may be a fungus, and more specifically a filamentous fungus belonging to the genus of *Aspergillus*, e.g. *A. niger, A. awamori, A. oryzae, A. nidulans*, a yeast belonging to the genus of *Saccharomyces*, e.g. *S. cerevisiae, S. kluyveri, S. bayanus, S. exiguus, S. sevazzi, S. uvarum*, a yeast belonging to the genus *Kluyveromyces*, e.g. *K. lactis K. marxianus* var. *marxianus, K. thermotolerans*, a yeast belonging to the genus *Candida*, e.g. *C. utilis C. tropicalis, C. albicans, C. lipolytica, C. versatilis*, a yeast belonging to the genus *Pichia*, e.g. *P. stipidis, P. pastoris, P. sorbitophila*, or other yeast genera, e.g. *Cryptococcus, Debaromyces, Hansenula, Pichia, Yarrowia, Zygosaccharomyces* or *Schizosaccharomyces*. Concerning other micro-organisms a non-exhaustive list of suitable filamentous fungi is supplied: a species belonging to the genus *Penicillium, Rhizopus, Fusarium, Fusidium, Gibberella, Mucor, Mortierella, Trichoderma*.

Concerning bacteria a non-exhaustive list of suitable bacteria is given as follows: a species belonging to the genus *Bacillus*, a species belonging to the genus *Escherichia*, a species belonging to the genus *Lactobacillus*, a species belonging to the genus *Lactococcus*, a species belonging to the genus *Corynebacterium*, a species belonging to the genus *Acetobacter*, a species belonging to the genus *Acinetobacter*, a species belonging to the genus *Pseudomonas*, etc.

The preferred micro-organisms of the invention may be *S. cerevisiae, A. niger, A. oryzae, E. coli, L. lactis* or *B. subtilis*.

The constructed and engineered micro-organism can be cultivated using commonly known processes, including chemostat, batch, fed-batch cultivations, etc.

Thus, the invention includes a method for producing resveratrol or an oligomeric or glycosidically-bound derivative thereof comprising contacting a non-plant cell with a carbon substrate in the substantial absence of an external source of 4-coumaric acid, said cell having the capacity to produce resveratrol or an oligomeric or glycosidically-bound derivative thereof under the conditions, in which the micro-organism may be selected from the group consisting of fungi and bacteria, especially yeast.

Said carbon substrate is optionally selected from the group of fermentable carbon substrates consisting of monosaccharides, oligosaccharides and polysaccharides, e.g. glucose, fructose, galactose, xylose, arabinose, mannose, sucrose, lactose, erythrose, threose, and/or ribose. Said carbon substrate may additionally or alternatively be selected from the group of non-fermentable carbon substrates including ethanol, acetate, glycerol, and/or lactate. Said non-fermentable carbon substrate may additionally or alternatively be selected from the group of amino acids and may be phenylalanine and/or tyrosine.

In an alternative aspect, the invention includes a method for producing resveratrol or an oligomeric or glycosidically-bound derivative thereof through heterologous expression of nucleotide sequences encoding phenylalanine ammonia lyase, cinnamate 4-hydroxylase, 4-coumarate-CoA ligase and resveratrol synthase and also a method for producing resveratrol through heterologous expression of nucleotide sequences encoding tyrosine ammonia lyase, 4-coumarate-CoA ligase and resveratrol synthase.

Resveratrol or an oligomeric or glycosidically-bound derivative thereof so produced may be used as a nutraceutical in a dairy product or a beverage such as beer.

Resveratrol produced according to the invention may be cis-resveratrol or trans-resveratrol, but it is to be expected that the trans-form will normally predominate.

BRIEF DESCRIPTION OF THE DRAWINGS

To assist in the ready understanding of the above description of the invention reference has been made to the accompanying drawings in which.

Figure 1:
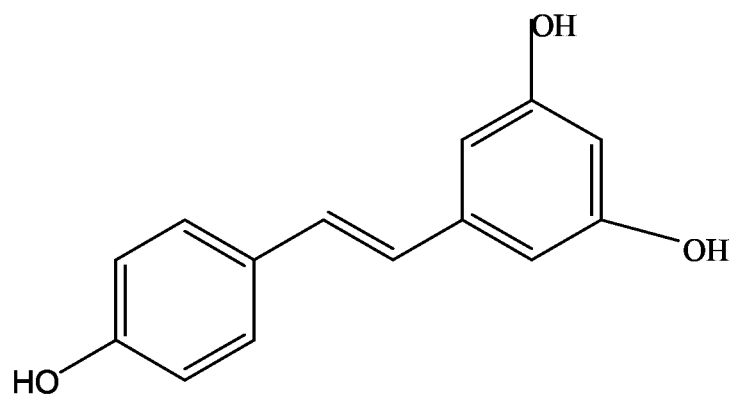
FIG. 1 shows the chemical structure of trans-resveratrol.
Figure 2:
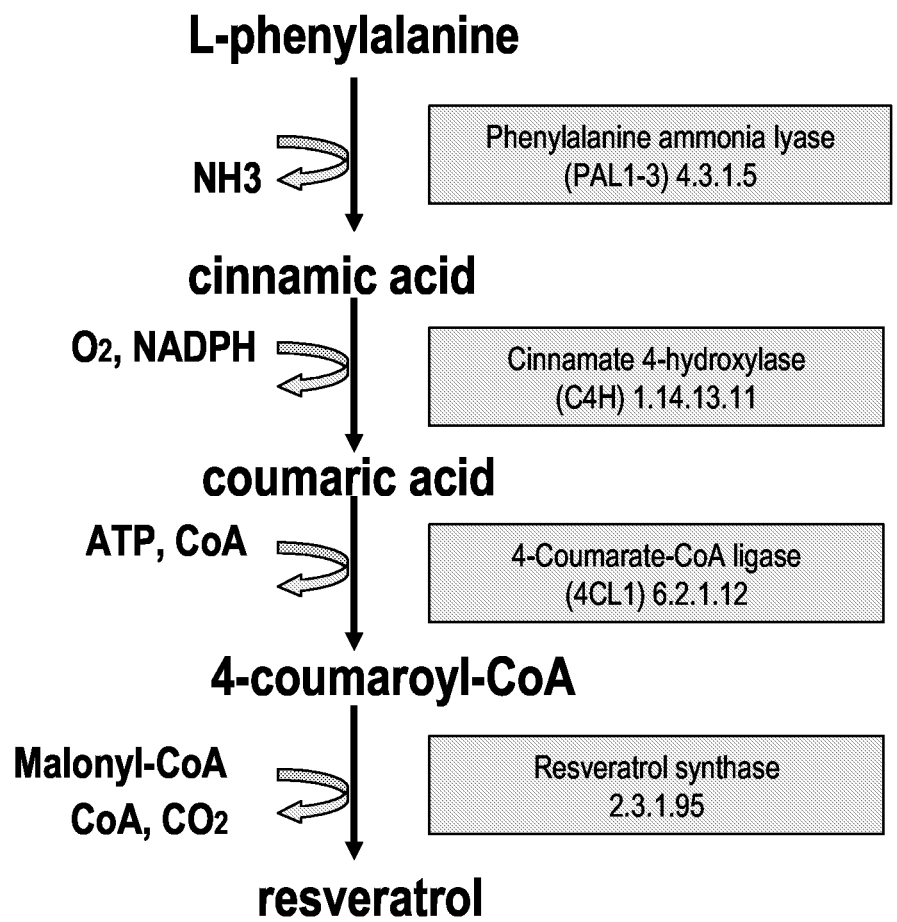
FIG. 2 shows the phenylpropanoid pathway utilising phenylalanine ammonia lyase acting on L-phenylalanine.
Figure 3:
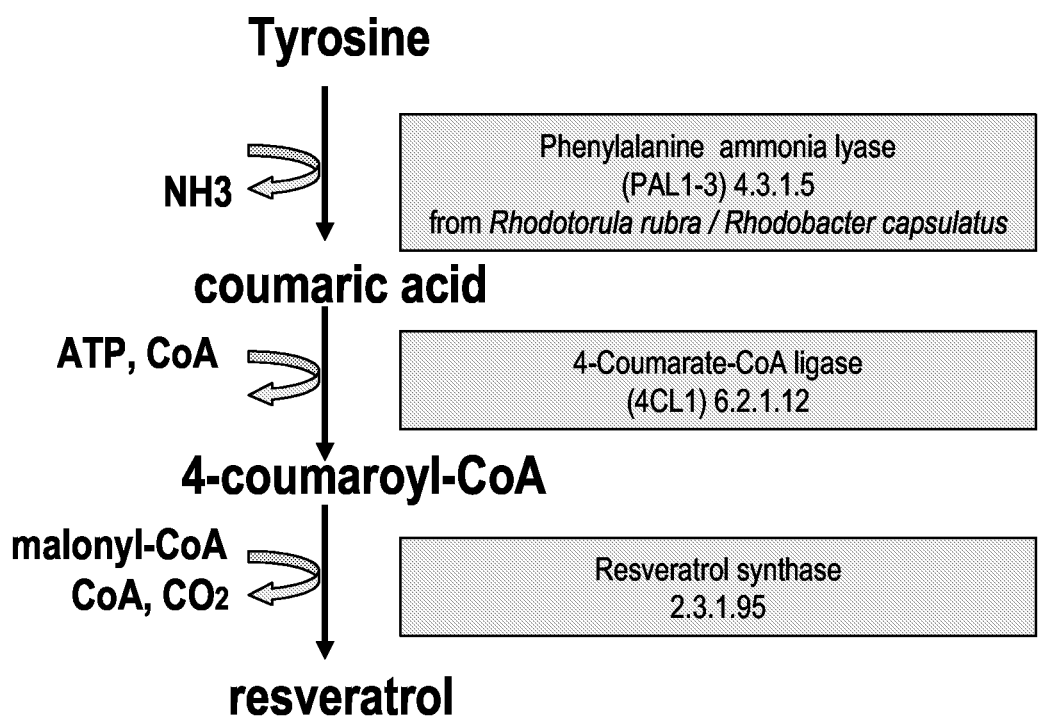
FIG. 3 shows the alternative pathway utilising phenylalanine ammonia lyase acting on L-tyrosine.

The invention will be further described and illustrated by the following non-limiting examples.

EXAMPLES

Example 1

Isolation of Genes Encoding PAL, TAL, C4H, CPR, 4CL, and VST

Phenylalanine ammonia lyase (PAL2) (Cochrane et al., 2004; SEQ ID NO: 1, 2), cinnamate 4-hydroxylase (C4H) (Mizutani et al., 1997; SEQ ID NO: 3, 4) and 4-coumarate:CoenzymeA ligase (4CL1) (Hamberger and Hahlbrock 2004; Ehlting et al., 1999; SEQ ID NO: 5, 6) were isolated via PCR from *A. thaliana* cDNA (BioCat, Heidelberg, Germany) using the primers in table 1. PAL2 and 4CL1 were chosen amongst several *A. thaliana* homologues due to favourable kinetic parameters towards cinnamic acid and coumaroyl-CoA, respectively (Cochrane et al., 2004; Hamberger and Hahlbrock 2004; Ehlting et al., 1999).

The coding sequence of resveratrol synthase (VST) from *Rheum tataricum*(Samappito et al., 2003; SEQ ID NO: 7, 8) and tyrosine ammonia lyase (TAL) from *Rhodobacter capsulatus* (Kyndt et al., 2002; SEQ ID NO: 11, 12) were codon optimized for expression in *S. cerevisiae*using the online service backtranslation tool at www DOT entelechon.com ("." replaced with "DOT" to inactivate URL), yielding sequence SEQ ID NO: 9, 10and SEQ ID NO: 13, 14 respectively. Oligos for the synthetic gene assembly were constructed at MWG Biotech and the synthetic gene was assembled by PCR using a slightly modified method protocol of from Martin et al. (2003) described below.

TABLE 1

Primers and restriction sites for the amplification of genes

| Primer for amplification of gene* (Restriction sites are underlined) | Gene | Restriction site: primer | Restriction site: vector |
|---|---|---|---|
| 5'-CG<u>GAATTC</u>TCATGGATCAAATCGAAGCAATGTT | PAL2 | EcoR1 | EcoR1 |
| 5'-CG<u>ACTAGT</u>TTAGCAAATCGGAATCGGAGC | PAL2 | Spe1 | Spe1 |
| 5'-CG<u>CTCGAG</u>AT ATGGACCTCCTCTTGCTGGA | C4H | Xho1 | Xho1 |

TABLE 1-continued

Primers and restriction sites for the amplification of genes

| Primer for amplification of gene* (Restriction sites are underlined) | Gene | Restriction site: primer | Restriction site: vector |
|---|---|---|---|
| 5'-CG<u>GGTACC</u>TTAACAGTTCCTTGGTTTCATAAC | C4H | Kpn1 | Kpn1 |
| 5'-GC<u>TCTAGA</u>CCT ATGGCGCCACAAGAACAAGCAGTTT | 4CL1 | Xba1 | Spe1 |
| 5'-GC<u>GGATCC</u>CCT TCACAATCCATTTGCTAGTTT TGCC | 4CL1 | BamH1 | BglII |
| 5'-CC<u>GGATCC</u>AAATGGCCCCAGAAGAGAGCAGG | VST | BamH1 | BamH1 |
| 5'-CG <u>CTCGAG</u>TTAAGTGATCAATGGAACCGAAGACAG | VST | Xho1 | Xho1 |
| 5'-CC<u>GAATTC</u>CCATGACCCTGCAATCTCAAACAGCTAAAG | TAL | EcoR1 | EcoR1 |
| 5'-CC<u>ACTAGT</u>TTAAGCAGGTGGATCGGCAGCT | TAL | Spe1 | Spe1 |
| 5'-CC<u>CTCGAG</u>ATCATGCCGTTTGGAATAGACAACACCGA | CPR1 | Xho1 | Xho1 |
| 5'-CC<u>AAGCTT</u>ATCGGGCTGATTACCAGACATCTTCTTG | CPR1 | HindIII | HindIII |
| 5'-CC<u>GGATCC</u>CCATGTCCTCTTCTTCTTCGTCAAC | AR2 | Bamh1 | Bamh1 |
| 5'-CC<u>CTCGAG</u>GTGAGTGTGTGGCTTCAATAGTTT CG | AR2 | Xho1 | Xho1 |

*SEQ ID Nos 19-32

Primers from MWG for the assembly of the synthetic gene were dissolved in milliQ-water to a concentration of 100 pmole/µl. An aliquot of 5 µl of each primer was combined in a totalmix and then diluted 10-fold with milliQ water. The gene was assembled via PCR using 5 µl diluted totalmix per 50 µl as template for fusion DNA polymerase (Finnzymes). The PCR programme was as follows: Initial 98° C. for 30 s., and then 30 cycles with 98° C. for 10 s., 40° C. for 1 min. and 72° C. at 1 min./1000 basepairs, and a final 72° C. for 5 min. From the resulting PCR reaction, 20 µl was purified on 1% agarose gel. The result was a PCR smear and the regions around the wanted size were cut out from agarose gel and purified using the QiaQuick Gel Extraction Kit (Qiagen). A final PCR with the outer primers (for TAL and VST) in table 1 rendered the required TAL and VST genes. Point mutations were corrected using either the Quickchange site directed mutagenesis II kit (Stratagene, La Jolla, Calif.), or using PCR from overlapping error free DNA stretches from several different E. coli subclones.

NADPH:Cytochrome P450 reductase (CPR) from A. thaliana (AR2) (Mizutani and Ohta, 1998; SEQ ID NO: 17, 18) and from S. cerevisiae (CPR1) (Aoyama et al., 1978; SEQ ID NO: 15, 16), were isolated from A. thaliana cDNA (BioCat, Heidelberg, Germany) and S. cerevisae genomic DNA, respectively, using the primers in table 1.

Example 2

Construction of a Yeast Vector for Expression of PAL

The gene encoding PAL, isolated as described in example 1, was reamplified by PCR using forward- and reverse primers, with 5' overhangs containing EcoR1 and Spe1 restriction sites (table 1). The amplified PAL PCR product was digested with EcoR1/Spe1 and ligated into EcoR1/Spe1 digested pESC-URA vector (Stratagene), resulting in vector pESC-URA-PAL. The sequence of the gene was verified by sequencing of two different clones.

Example 3

Construction of a Yeast Vector for Expression of PAL and C4H

The gene encoding C4H, isolated as described in example 1, was amplified by PCR using the forward- and reverse primers, with 5' overhangs containing Xho1 and Kpn1 restriction sites. The amplified C4H PCR-product was digested with Xho1/Kpn1 and ligated into similarly digested pESC-URA-PAL vector. The resulting plasmid, pESC-URA-PAL-C4H, contained the genes encoding PAL and C4H under the control of the divergent GAL1/GAL10 promoter. The sequence of the gene encoding C4H was verified by sequencing of two different clones.

Example 4

Construction of a Yeast Vector for Expression of 4CL

The gene encoding 4CL was isolated as described in example 1. The amplified 4CL PCR-product was digested with Xba1/BamH1 and ligated into Spe1/BglII digested pESC-TRP vector (Stratagene), resulting in vector pESC-TRP-4CL. Two different clones of pESC-TRP-4CL were sequenced to verify the sequence of the cloned gene.

Example 5

Construction of a Yeast Vector for Expression of 4CL and VST

The gene encoding VST was isolated as described in example 1. The amplified synthetic VST gene was digested with BamH1/Xho1 and ligated into BamH1/Xho1 digested pESC-TRP-4CL (example 4). The resulting plasmid, pESC-TRP-4CL-VST, contained the genes encoding 4CL and VST under the control of the divergent GAL1/GAL10 promoter. The sequence of the gene encoding VST was verified by sequencing of two different clones of pESC-TRP-4CL-VST.

Example 6

Construction of a Yeast Vector for Expression of TAL

The gene encoding TAL was isolated as described in example 1. The amplified synthetic TAL gene was digested with EcoR1/Spe1 and ligated into EcoR1/Spe1-digested pESC-URA vector. The resulting plasmid, pESC-URA-TAL, contained the gene encoding for TAL under the control of the divergent GAL1/GAL10 promoter. The sequence was verified by sequencing of two different clones of pESC-URA-TAL.

Example 7

Construction of a Yeast Vector for Overexpression of S. cerevisiae Endogenous CPR The gene encoding CPR from S. cerevisiae (CPR1) was isolated as described in example 1. The amplified CPR1 gene was digested with Xho1/HindIII and ligated into Xho1/HindIII-digested pESC-LEU vector (Stratagene), resulting in vector pESC-LEU-CPR1. The sequence was verified by sequencing of two different clones of pESC-LEU-CPR1.

Example 8

Construction of a Yeast Vector for Overexpression of A. thaliana CPR (AR2)

The gene encoding CPR from A. thaliana (AR2) was isolated as described in example 1. The amplified AR2 gene was digested with BamH1/Xho1 and ligated into BamH1/Xho1 digested pESC-LEU vector (Stratagene), resulting in vector pESC-LEU-AR2. The sequence was verified by sequencing of two different clones of pESC-LEU-AR2.

Example 9

Expression of the Pathway to Resveratrol in the Yeast S. cerevisiae Using PAL, C4H, 4CL and VST Yeast strains containing the appropriate genetic markers were transformed with the vectors described in examples 2, 3, 4, 5, 6, 7 and 8, separately or in combination. The transformation of the yeast cell was conducted in accordance with methods known in the art, for instance, by using competent cells or by electroporation (see, e.g., Sambrook et al., 1989). Transformants were selected on medium lacking uracil and/or tryptophan and streak purified on the same medium.

S. cerevisiae strain CEN.PK 113-5D (MATa ura3) was transformed separately with the vector pESC-URA-PAL (example 2), yielding the strain FSSC-PAL, and with pESC-URA-PAL-C4H (example 3), resulting in the strain FSSC-PALC4H. S. cerevisiae strain FS01267 (MATa trp1 ura3) was co-transformed with pESC-URA-PAL-C4H and pESC-TRP-4CL (example 4), and the transformed strain was named FSSC-PALC4H4CL. The same strain was also co-transformed with pESC-URA-PAL-C4H and pESC-TRP-4CL-VST (example 5), resulting in the strain FSSC-PALC4H4CLVST.

Example 10

Expression of the Pathway to Resveratrol in S. cerevisiae Using TAL, 4CL and VST S. cerevisiae strain CEN.PK 113-5D (MATa ura3) was transformed separately with the vector pESC-URA-TAL (example 6), yielding the strain FSSC-TAL. S. cerevisiae strain FS01267 (MATa trp1 ura3) was co-transformed with pESC-URA-TAL (example 6) and pESC-TRP-4CL (example 4), and the transformed strain was named FSSC-TAL4CL. The same strain was also co-transformed with pESC-URA-TAL and pESC-TRP-4CL-VST (example 5), resulting in the strain FSSC-TAL4CLVST. Transformants were selected on medium lacking uracil and or tryptophan and streak purified on the same medium.

Example 11

Expression of the Pathway to Resveratrol in S. cerevisiae with Overexpressed Endogenous CPR S. cerevisiae strain FS01277 (MATa ura3 leu2 trp1) was co-transformed with vectors pESC-URA-PAL-C4H (example 3), pESC-TRP-4CL (example 4), and pESC-LEU-CPR1 (example 7). The transformed strain was named FSSC-PALC4H4CLVSTCPR. Transformants were selected on medium lacking uracil and/or tryptophan and streak purified on the same medium.

Example 12

Expression of the Pathway to Resveratrol in S. Cerevisiae with Overexpressed A. Thaliana CPR (AR2)

S. cerevisiae strain FS01277 (MATa ura3 leu2 trp1) was co-transformed with vectors pESC-URA-PAL-C4H (example 3), pESC-TRP-4CL (example 4), and pESC-LEU-AR2 (example 8). The transformed strain was named FSSC-PALC4H4CLVSTAR2. Transformants were selected on medium lacking uracil and or tryptophan and streak purified on the same medium.

Example 13

Fermentation with Recombinant Yeast Strains in Shake Flasks

The recombinant yeast strains were inoculated from agar plates with a sterile inoculation loop and grown in 200 ml defined mineral medium (Verduyn et al, 1992) that contained vitamins, trace elements, 5 g/l glucose and 40 g/l or 100 g/l galactose. The 500 ml stoppered shake flasks were incubated for three days at 30° C. and 160 rpm.

Example 14

Extraction of Resveratrol

Cells were harvested by centrifugation 5000 g for 5 minutes. An aliquot of 50 ml of supernatant was extracted once with 20 ml ethyl acetate. The ethyl acetate was freeze dried and the dry product redissolved in 0.7 ml methanol and filtered into HPLC vials.

The cell pellet from 200 ml medium was dissolved in 1 to 2 ml water and divided into 3 fastprep tubes and broken with glass beads. The crude extracts from the three tubes were pooled into 10 ml 100% methanol in a 50 ml sartorius tube and extracted on a rotary chamber for 48 hours in a dark cold room at 4° C. After 48 hours the cell debris was removed via centrifugation for 5 min. at 5000 g and the methanol was removed by freeze-drying overnight. The dried residue was redissolved in 1 ml phosphate-citrate buffer pH 5.4 and 10 units beta-glucosidase from almonds was added (Sigma) to release resveratrol from putatively glucoside-bound forms. The mixture was incubated for three hours at 37° C. and then extracted twice with 1 ml ethyl acetate. The combined ethyl acetate was freeze dried and the dry residue was redissolved in 0.7 ml methanol and filtered into HPLC vials.

Example 15

Analysis of Resveratrol

Thin Layer Chromatography

A method based upon thin layer chromatography that enabled the quick separation of cinnamic, coumaric and resveratrol on the same TLC-plate was developed for quick screening analysis. An aliquot of 1 ml culture containing both cells and supernatant were extracted with 500 microliter ethyl acetate and centrifuged for 30 s. at 13000 rpm with a microcentrifuge. The ethyl acetate was dried and redissolved in methanol. The extracts were analyzed on Silica G plates (0.2 mm Alugram SIL G/UV$_{254}$, Macherey-Nagel) containing a fluorescent indicator. The mobile phase was a mixture of chloroform, ethyl acetate and formic acid (25:10:1).
HPLC For quantitative analysis of cinnamic acid, coumaric acid, and resveratrol, samples were subjected to separation by high-performance liquid chromatography (HPLC) Agilent Series 1100 system (Hewlett Packard) prior to uv-diode-array detection at λ=306 nm. A Phenomenex (Torrance, Calif., USA) Luna 3 micrometer C18 (100×2.00 mm) column was used at 40° C. As mobile phase a gradient of acetonitrile and milliq water (both containing 50 ppm trifluoroacetic acid) was used at a flow of 0.4 ml/min. The gradient profile was linear from 15% acetonitrile to 100% acetonitrile over 20 min. The elution times were approximately 3.4 min. for coumaric acid, 5.5 min. for free trans-resveratrol and 6.8 min. for cinnamic acid.

Figure 4:
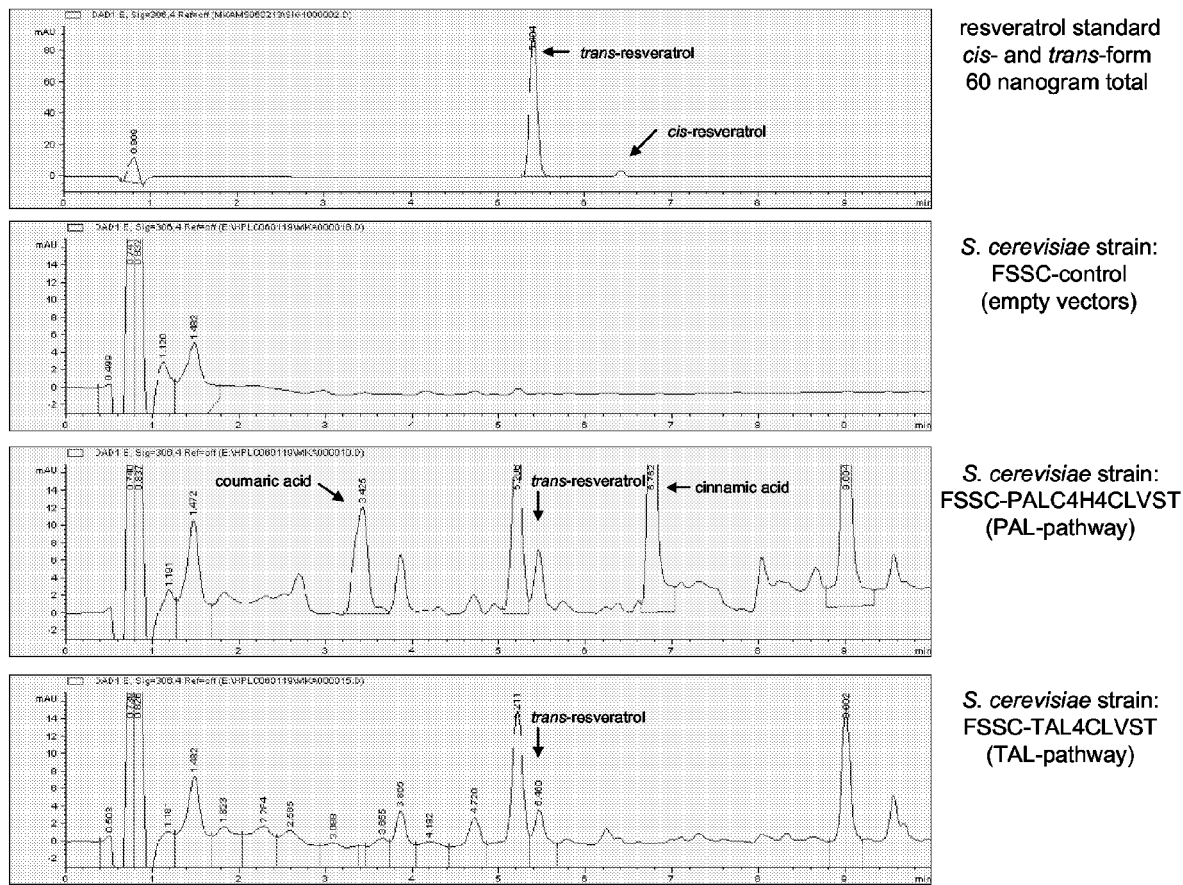
FIG. 4 shows the HPLC-chromatograms of extracts of *S. cerevisiae* strains FSSC-PALC4H4CLVST, FSSC-TAL4CLVST, grown on 100 g/l galactose. A chromatogram of 60 nanogram of pure resveratrol is included.
Figure 5:
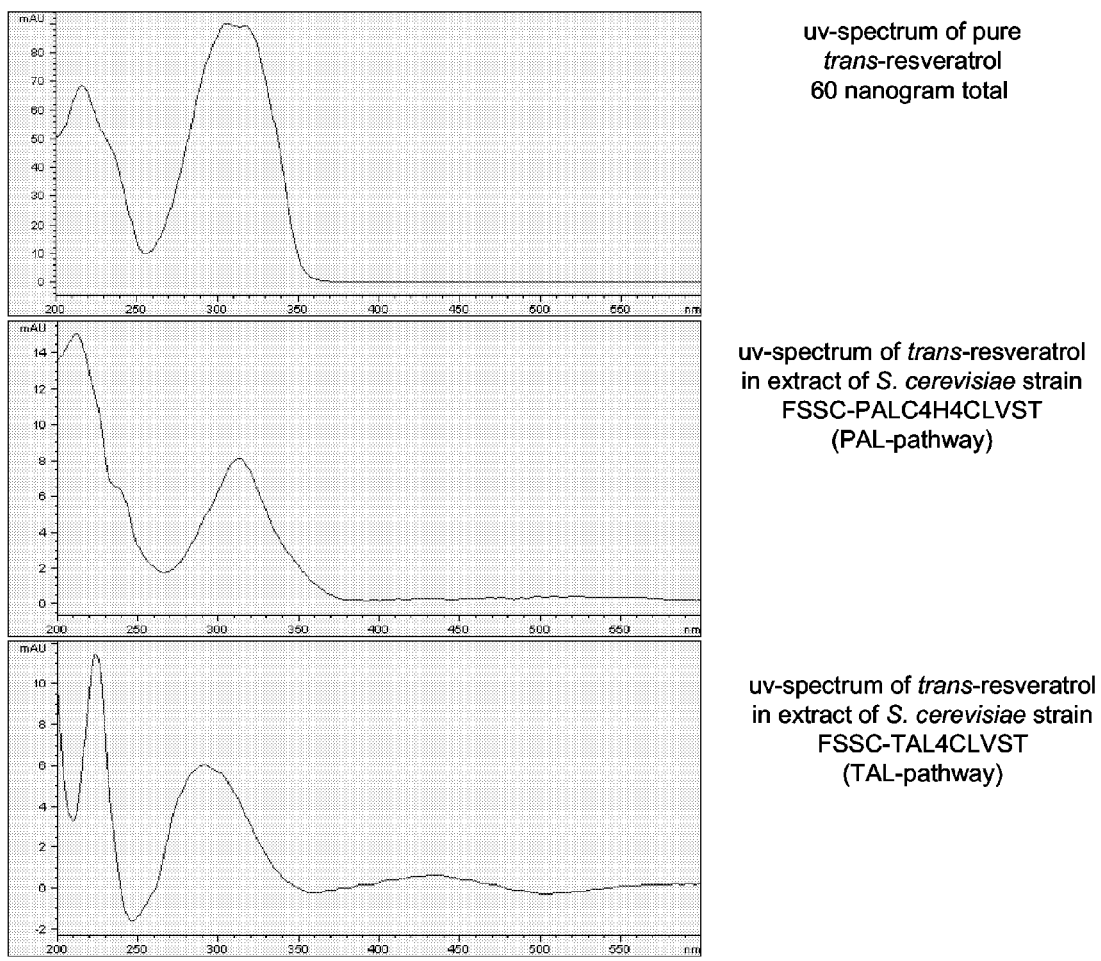
FIG. 5 shows the UV absorption spectrum for pure trans-resveratrol and trans-resveratrol produced by *S. cerevisiae* strain FSSC-PALC4H4CLVST, grown on 100 g/l galactose.

Pure resveratrol standard was purchased from Cayman chemical company, whereas pure coumaric acid and cinnamic acid standards were purchased from and Sigma.
Results Strains FSSC-PALC4H4CLVST and FSSC-TAL4CLVST, were cultivated on 100 g/l galactose as described in example 13, and analyzed for their content of intracellular resveratrol according to example 14 and 15. Additionally, a control strain FSSC-control was included that contained the empty vectors pESC-URA and pESC-TRP only. The HPLC-analysis showed that strains FSSC-PALC4H4CLVST and FSSC-TAL4CLVST contained a component with a retention time of 5.5 min. that was identical to trans-resveratrol (FIG. 4). Said result was confirmed by the UV absorption spectra that were similar to the absorption spectrum of pure trans-resveratrol (FIG. 5) as well, with a $\lambda_{max}$ of approximately 306 nm.

The results, therefore, demonstrated the presence of an active phenyl-propanoid pathway in *S. cerevisiae* that led to in vivo production of trans-resveratrol. The production of resveratrol can most likely be improved by cultivating the strains under well-defined growth conditions in batch- and continuous cultures, and/or optimizing the expression/activities of the individual enzymes.

Example 16

Construction of a Bacterial Vector for Expression of TAL in *Escherichia coli*

The gene encoding TAL, isolated as described in Example 1, was reamplified by PCR from the plasmid pESC-URA-TAL (example 6) using the forward primer 5'-CCG CTCGAG CGG ATG ACC CTG CAA TCT CAA ACA GCT AAA G-3' SEQ ID NO 33 and the reverse primer 5'-GC GGATCC TTA AGC AGG TGG ATC GGC AGC T-3' SEQ ID NO 34 with 5' overhangs containing the restriction sites XhoI and BamHI, respectively. The introduction of restriction sites at the 5' and 3' ends of the gene allowed ligation of the restricted PCR product into a pET16b vector (Novagen), digested with XhoI and BamHI to yield pET16b-TAL. The pET16b vector contained both the ampicillin resistance gene, and the T7 promoter. Hence, above procedure resulted in a vector with an antibiotic selection marker that contained the gene encoding for TAL under the control of the T7 promoter. The sequence of the gene encoding TAL was verified by sequencing of one clone of pET16b-TAL.

Example 17

Construction of a Bacterial Vector for Expression of 4CL and VST in *Escherichia coli*

The gene encoding VST, isolated as described in example 1, was cut out with the restriction enzymes BamHI and XhoI from the digested plasmid pESC-TRP-4CL-VST (example 5), which contains the genes encoding 4CL and VST. The VST gene was ligated into a pET26b vector (Novagen), containing the kanamycin resistance gene, digested with BamHI and SalI to yield pET26b-VST. The restriction enzymes XhoI and SalI have compatible ends, which enabled proper ligation. The pET26b vector contained both the kanamycin resistance gene, and the T7 promoter. Hence, above procedure resulted in a vector with an antibiotic selection marker that contained the gene encoding for VST under the control of the T7 promoter.

The gene encoding for 4CL, isolated as described in example 1, was reamplified by PCR from the plasmid pESC-URA-4CL-VST (example 5) using the forward primer 5'-TG CCATGG CA ATGGCGCCAC AAGAACAAGC AGTTT-3' SEQ ID NO 35 and the reverse primer 5'-GC GGATCC CCT TCA CAA TCC ATT TGC TAG TTT TGCC-3' SEQ ID NO 36 with 5' overhangs containing the restriction sites NcoI and BamHI, respectively. The introduction of restriction sites at the 5' and 3' ends of the gene allowed ligation of the restricted PCR product into a pET16b vector (Novagen) digested with NcoI and BamHI. The resulting plasmid, pET16b-4CL, contained the gene encoding for 4CL under the control of the T7 promoter. Both the T7 promoter and the gene encoding for 4CL were reamplified as one fragment by PCR from the plasmid pET16b-4CL using the forward primer 5'-TT GCG-GCCGC AAA TCT CGA TCC CGC GAA ATT AAT ACG-3' SEQ ID NO 37 and the reverse primer 5'-CG CTCGAG CCT TCA CAA TCC ATT TGC TAG TTT TGCC-3' SEQ ID NO 38 with 5' overhangs, containing the restriction sites NotI and XhoI, respectively. The introduction of restriction sites at the 5' and 3' ends of the DNA fragment allowed ligation of the restricted PCR product into the plasmid pET26b-VST that was digested with NotI and XhoI before ligation. The resulting plasmid, pET26b-VST-4CL, contained the two genes 4CL and VST that each were under control of an individual T7 promoter.

Example 18

Expression of the Pathway to Resveratrol in *Escherichia coli*, Using TAL, 4CL and VST The transformation of the bacterial cell was conducted in accordance with methods known in the art, for instance, by using competent cells or by electroporation (see, e.g., Sambrook et al., 1989). The E. coli strain BL21 (DE3) (Novagen) was co-transformed with the two vectors pET16b-TAL (example 16) and pET26b-VST-4CL (Example 17), resulting in strain FSEC-TAL4CLVST. In addition, E. coli strain BL21 (DE3) was co-transformed with the two empty vectors pET16b (Novagen) and pET26b (Novagen), resulting in strain FSEC-control, which was used as a control strain. Transformants were selected on Luria-Bertani (LB) medium with 100 µg/ml ampicillin and 60 µg/ml kanamycin.

Example 19

Fermentation with Recombinant *Escherichia coli* Strains in Shake Flasks

Pre-cultures of *Escherichia coli* BL21 (DE3) were grown in glass tubes at 160 rpm and 37° C. in 7 ml of LB medium containing 100 µg/ml ampicillin and 60 µg/ml kanamycin. Exponentially growing precultures were used for inoculation of 500 ml baffled shake flasks that contained 200 ml LB medium supplemented with 50 g/l glucose, 5 g/l $K_2HPO_4$, 80 µg/ml ampicillin and 50 µg/ml kanamycin, which were incubated at 160 rpm and 37° C. After 5 hours, isopropyl β-thiogalactopyranoside (IPTG) was added at a final concentration of 1 mM, as an inducer of the T7 promoter that was in front of each of the three genes TAL, 4CL and VST. After an incubation period of 48 hours at 37° C., the cells were harvested and subjected to extraction procedures and analysed for the presence of produced resveratrol.

Example 20

Extraction and Analysis of Resveratrol in *Escherichia coli*

Figure 6:
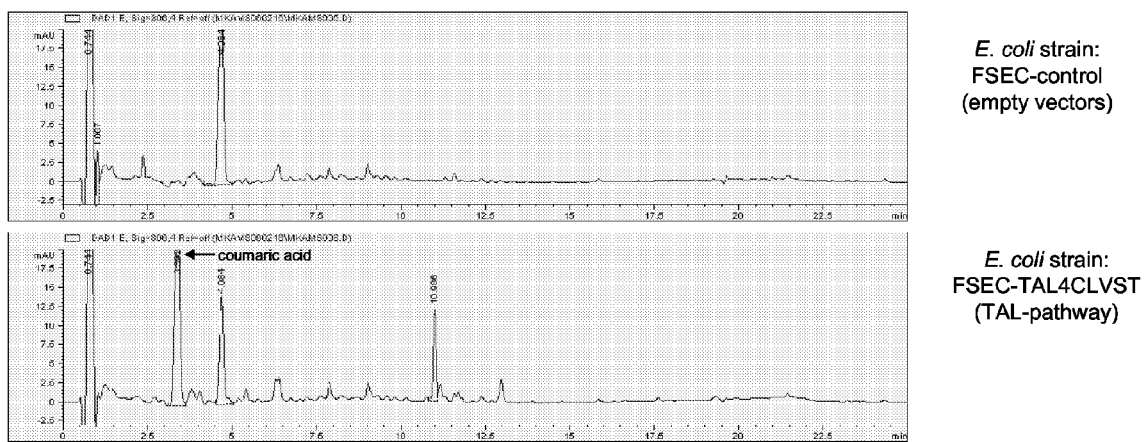
FIG. 6 shows the HPLC-chromatograms of extracts from *E. coli* strains FSEC-TAL4CLVST and FSEC-control, grown on 50 g/l glucose.
Figure 7:
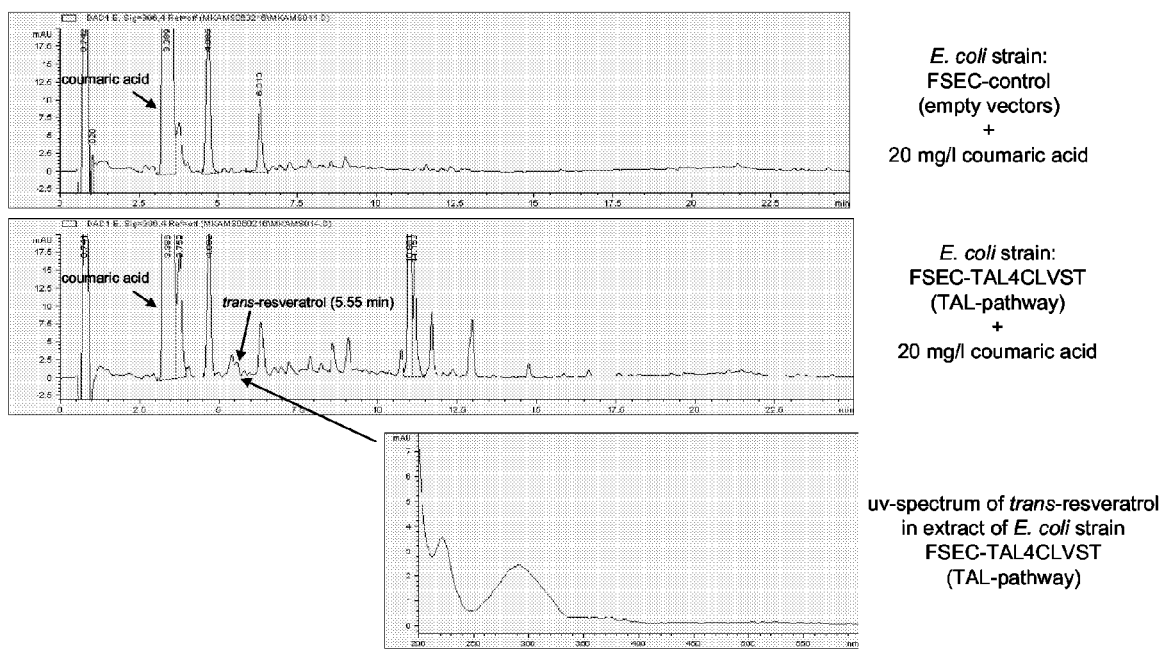
FIG. 7 shows the HPLC-chromatograms of extracts from *E. coli* strains FSEC-TAL4CLVST and FSEC-control, grown on 50 g/l glucose with addition of 20 mg/l coumaric acid. The UV absorption spectrum for trans-resveratrol produced in strain FSEC-TAL4CLVST is included.

Extraction and analysis was performed using the methods as described in example 14 and 15.
Results
Strain FSEC-TAL4CLVST and FSEC-control, were cultivated on 50 g/l glucose as described in example 19, and analyzed for their content of intracellular resveratrol according to example 14 and 15. The HPLC-analysis showed that strain FSEC-TAL4CLVST did contain considerable amounts of a component with a retention time of 3.4 min., which is identical to coumaric acid (FIG. 6). However, the extract did not contain a component that eluted at the same time as trans-resveratrol. Said result, therefore, indicated that the tyrosine ammonia lyase (TAL) was active indeed, but did not lead to production of detectable amounts of resveratrol. The lack of resveratrol formation, however, could be the result of; i) a non-functional coumarate-CoA ligase (4CL); ii) a non-functional resveratrol synthase (VST); iii) too low levels of coumaric acid, caused by either non-optimal cultivation conditions, or non-optimal expression/activity of TAL, or branching of coumaric acid into other products. To evaluate said hypotheses, the strains were grown on similar media as described in example 19 but now in the presence of 20 mg/l of coumaric acid. The subsequent HPLC-analysis of extracts of FSEC-TAL4CLVST indeed showed a cluster of peaks around the same retention time as trans-resveratrol, which was not observed in extracts of FS-control (FIG. 6). Indeed, the UV absorption spectrum of the peak with a retention time of 5.5 min. was similar to the spectrum of pure trans-resveratrol (FIG. 7), whereas no such spectrum could be obtained for peaks in the control strain. The results, therefore, strongly suggest the presence of an active phenylpropanoid pathway in *Escherichia coli*, which can lead to production of resveratrol. Most likely the production of resveratrol without addition of coumaric acid can be achieved by cultivating the strains under well-defined growth conditions in batch- and continuous cultures, and/or optimizing the expression/activities of the individual enzymes.

Example 21

Construction of a Bacterial Vector for Expression of PAL and C4H in *Lactococcus lactis*

The plasmid pSH71 and derivatives thereof, which is used in the following examples, is a bifunctional shuttle vector with multiple origins of replication from *Escherichia coli* and *Lactococcus lactis*. With that, the host range specificity traverses *Escherichia coli* and other species of lactic acid bacteria. Though transformations in *Lactoccus lactis* usually proceed without problems, putative difficult transformations in other species of lactic acid bacteria can, therefore, be overcome by using *Escherichia coli* as an intermediate host for the construction of recombinant plasmids. The plasmid contains one or more marker genes to allow the microorganism that harbour them to be selected from those which do not. The selection system that is used for *Lactococcus lactis* is based upon dominant markers, e.g. resistance against erythromycin and chloramphenicol, but systems based upon genes involved in carbohydrate metabolism, peptidases and food grade markers, have also been described. In addition, the plasmid contains promoter- and terminator sequences that allow the expression of the recombinant genes. Suitable promoters are taken from genes of *Lactococcus lactis* e.g. lacA. Furthermore, the plasmid contains suitable unique restriction sites to facilitate the cloning of DNA fragments and subsequent identification of recombinants.

In the examples below the plasmid contains either the erythromycine resistance gene, designated as pSH71-ERY$^r$, or the chloramphenicol resistance gene, designated as pSH71-CM$^r$ The gene encoding PAL, isolated as described in example 1, is reamplified by PCR from the plasmid pESC-URA-PAL-C4H (example 3), using forward- and reverse primers, with 5' overhangs containing suitable restriction sites. The introduction of said restriction sites at the 5' and 3' ends of the gene allows ligation of the restricted PCR product into a digested pSH71-ERY$^r$ vector that contains the lacA promoter from *Lactococcus lactis*. The resulting plasmid, pSH71-ERY$^r$-PAL, contains the gene encoding PAL under the control of the lacA promoter from *Lactococcus lactis*.

The gene encoding C4H, isolated as described in example 1, is reamplified by PCR from the plasmid pESC-URA-PAL-C4H (example 3) using forward- and reverse primers, with 5' overhangs containing suitable restriction sites. The introduction of said restriction sites at the 5' and 3' ends of the gene allows ligation of the restricted PCR product into a digested pSH71-CM$^r$ vector to yield pSH71-CM$^r$-C4H. The lacA promoter and the gene encoding C4H are reamplified as one fragment by PCR from the plasmid pSH71-CM$^r$-C4H using forward- and reverse primers, with 5' overhangs containing suitable restriction sites. The introduction of said restriction sites at the 5' and 3' ends of the DNA fragment allows ligation of the restricted PCR product into the digested plasmid pSH71-ERY$_r$-PAL. The resulting plasmid, pSH71-ERY$_r$-PAL-C4H, contains the genes encoding PAL and C4H that are each under the control of an individual lacA promoter. The sequence of the genes encoding PAL and C4H is verified by sequencing of two different clones of pSH71-ERY$^r$-PAL-C4H.

Example 22

Construction of a Bacterial Vector for Expression of TAL in *Lactococcus lactis*

The gene encoding for TAL, isolated as described in example 1, is reamplified by PCR from the plasmid pESC-URA-TAL (example 6) using forward- and reverse primers, with 5' overhangs containing suitable restriction sites. The introduction of said restriction sites at the 5' and 3' ends of the gene allows ligation of the restricted PCR product into a digested pSH71-ERY$^r$ vector. The resulting plasmid, pSH71-ERY$^r$-TAL, contains the gene encoding for TAL under the control of the lacA promoter from *Lactococcus lactis*. The sequence of the gene encoding for TAL is verified by sequencing of two different clones of pSH71-ERY$^r$-TAL.

Example 23

Construction of a Bacterial Vector for Expression of 4CL and VST in *Lactococcus lactis*

The gene encoding 4CL, isolated as described in example 1, is reamplified by PCR from the plasmid pESC-TRP-4CL-VST (example 5), using forward- and reverse primers, with 5' overhangs containing suitable restriction sites. The introduction of said restriction sites at the 5' and 3' ends of the gene allows ligation of the restricted PCR product into a digested pSH71-CM$^r$ vector. The resulting plasmid, pSH71-CM$^r$-4CL, contains the gene encoding for 4CL under the control of the lacA promoter from *Lactobacillus lactis*.

The gene encoding VST, isolated as described in example 1, is reamplified by PCR from the plasmid pESC-TRP-4CL-VST (example 5) using forward- and reverse primers, with 5' overhangs containing suitable restriction sites. The introduction of said restriction sites at the 5' and 3' ends of the gene allows ligation of the restricted PCR product into a digested pSH71-ERY$^r$ vector. The resulting plasmid, pSH71-ERY$^r$-VST, contains the gene encoding VST under the control of the lacA promoter from *Lactococcus lactis*. The lacA promoter and the gene encoding VST are reamplified as one fragment by PCR from the plasmid pSH71-ERY$^r$-VST using forward- and reverse primers, with 5' overhangs containing suitable restriction sites. The introduction of said restriction sites at the 5' and 3' ends of the DNA fragment allows ligation of the restricted PCR product into the digested plasmid pSH71-CM$^r$-4CL. The resulting plasmid, pSH71-CM$^r$-4CL-VST, contains the genes encoding 4CL and VST that are each under the control of their individual lacA promoter. The sequence of the genes encoding 4CL and VST is verified by sequencing of two different clones of pSH71-CM$^r$-4CL-VST.

Example 24

Expression of the Pathway to Resveratrol in *Lactococcus lactis*

*Lactococcus lactis* strains are transformed with the vectors described in examples 21, 22 and 23, separately or in combination. The transformation of the bacterial cell is conducted in accordance with methods known in the art, for instance, by using competent cells or by electroporation (see, e.g., Sambrook et al., 1989). Transformants are selected on medium containing the antibiotics erythromycin and chloramphenicol and streak purified on the same medium.

*Lactococcus lactis* strain MG1363 is transformed separately with the vector pSH71-ERY$^r$-TAL (example 22), yielding the strain FSLL-TAL; with pSH71-ERY$^r$-PAL-C4H (example 21), yielding the strain FSLL-PALC4H and with pSH71-CM$^r$-4CL-VST (example 23), yielding strain FSLL-4CLVST. In addition, *Lactococcus lactis* strain MG1363 is co-transformed with pSH71-ERY$^r$-TAL (example 22) and pSH71-CM$^r$-4CL-VST (example 23), and the transformed strain is named FSLL-TAL4CLVST. The same strain is also co-transformed with pSH71-ERY$^r$-PAL-C4H (example 21), and pSH71-CM$^r$-4CL-VST (example 23), resulting in the strain FSLL-PALC4H4CLVST.

Example 25

Fermentation with Recombinant *Lactococcus lactis* Strains in Fermentors

The recombinant yeast strains can be grown in fermenters operated as batch, fed-batch or chemostat cultures.
Batch and Fed-Batch Cultivations The microorganism is grown in a baffled bioreactor with a working volume of 1.5 liters under anaerobic, aerobic or microaerobic conditions. All cultures are incubated at 30° C., at 350 rpm. A constant pH of 6.6 is maintained by automatic addition of 10 M KOH. Cells are grown on lactose in defined MS10 medium supplemented with the following components to allow growth under aerobic conditions: $MnSO_4$ ($1.25 \times 10^{-5}$ g/l), thiamine (1 mg/l), and DL-6,8-thioctic acid (2.5 mg/l). The lactose concentration is, for example 50 g/l. The bioreactors are inoculated with cells from precultures grown at 30° C. in shake flasks on the medium described above buffered with threefold-higher concentrations of $K_2HPO_4$ and $KH_2PO_4$. Anaerobic conditions are ensured by flushing the medium with $N_2$ (99.998% pure) prior to inoculation and by maintaining a constant flow of 50 ml/min of $N_2$ through the headspace of the bioreactor during cultivation. The bioreactors used for microaerobic and aerobic cultivation are equipped with polarographic oxygen sensors that are calibrated with air (DOT, 100%) and $N_2$ (DOT, 0%). Aerobic conditions are obtained by sparging the bioreactor with air at a rate of 1 vvm to ensure that the DOT is more than 80%. During microaerobic experiments the DOT is kept constant 5% by sparging the reactor with gas composed of a mixture of $N_2$ and atmospheric air, at a rate of 0.25 vvm.
Chemostat Cultures In chemostat cultures the cells can be grown in, for example, 1-L working-volume Applikon laboratory fermentors at 30° C. and 350 rpm. The dilution rate (D) can be set at different values, e.g. at 0.050 h$^{-1}$, 0.10 h$^{-1}$, 0.15 h$^{-1}$, or 0.20 h$^{-1}$. The pH is kept constant, e.g at 6.6, by automatic addition of 5 M KOH, using the growth medium described above, supplemented with antifoam (50 µl/l). The concentration of lactose can be set at different values, e.g. is 3.0 g/l 6.0 g/l, 12.0 g/l, 15.0 g/l or 18.0 g/l. The bioreactor is inoculated to an initial biomass concentration of 1 mg/l and the feed pump is turned on at the end of the exponential growth phase.

An anaerobic steady state is obtained by introducing 50 ml/min of $N_2$ (99.998% pure) into the headspace of the bioreactor. Different anoxic steady states can obtained by sparging the reactor with 250 ml/min of gas composed of $N_2$ (99.998% pure) and atmospheric air at various ratios. The oxygen electrode is calibrated by sparging the bioreactor with air (100% DOT) and with $N_2$ (0% DOT).

For all conditions, the gas is sterile filtered before being introduced into the bioreactor. The off gas is led through a condenser cooled to lower than −8° C. and analyzed for its volumetric content of $CO_2$ and $O_2$ by means of an acoustic gas analyser.

Cultivations are considered to be in steady state after at least 5 residence times, and if the concentrations of biomass and fermentation end products remain unchanged (less than 5% relative deviation) over the last two residence times.

Example 26

Extraction and Analysis of Resveratrol in Lactococcus Lactis

Extraction and analysis is performed using the methods as described in examples 14 and 15.

Example 27

Construction of a Fungal Vector for Expression of PAL and C4H in Species Belonging to the Genus Aspergillus The plasmid that is used in the following examples, is derived from pARp1 that contains the AMA1 initiating replication sequence from Aspergillus nidulans, which also sustains autonomous plasmid replication in A. niger and A. oryzae (Gems et al., 1991). Moreover, the plasmid is a shuttle vector, containing the replication sequence of Escherichia coli, and the inherent difficult transformations in Aspergillus niger and Aspergillus oryzae can therefore overcome by using Escherichia coli as an intermediate host for the construction of recombinant plasmids. The plasmid contains one or more marker genes to allow the microorganism that harbour them to be selected from those which do not. The selection system can be either based upon dominant markers e.g. resistance against hygromycin B, phleomycin and bleomycin, or heterologous markers e.g amino acids and the pyrG gene. In addition the plasmid contains promoter- and terminator sequences that allow the expression of the recombinant genes. Suitable promoters are taken from genes of Aspergillus nidulans e.g. alcA, glaA, amy, niaD, and gpdA. Furthermore, the plasmid contains suitable unique restriction sites to facilitate the cloning of DNA fragments and subsequent identification of recombinants.

The plasmid used in the following examples contains the strong constitutive gpdA-promoter and auxotropic markers, all originating from Aspergillus nidulans; the plasmid containing the gene methG that is involved in methionine biosynthesis, is designated as pAMA1-MET; the plasmid containing the gene hisA that is involved in histidine biosynthesis, is designated as pAMA1-HIS.

The gene encoding PAL, isolated as described in example 1, is reamplified by PCR from the plasmid pESC-URA-PAL-C4H (example 3), using forward- and reverse primers, with 5' overhangs containing suitable restriction sites. The introduction of said restriction sites at the 5' and 3' ends of the gene allows ligation of the restricted PCR product into a digested pAMA1-MET vector that contains the gpdA promoter from Aspergillus nidulans. The resulting plasmid, pAMA1-MET-PAL contains the gene encoding PAL under the control of the gpdA promoter from Aspergillus nidulans.

The gene encoding C4H, isolated as described in example 1, is reamplified by PCR from the plasmid pESC-URA-PAL-C4H (example 3) using forward- and reverse primers, with 5' overhangs containing suitable restriction sites. The introduction of said restriction sites at the 5' and 3' ends of the gene allows ligation of the restricted PCR product into a digested pAMA1-HIS vector to yield pAMA1-HIS-C4H. The gpdA promoter and the gene encoding C4H are reamplified as one fragment by PCR from the plasmid pAMA1-HIS-C4H using forward- and reverse primers, with 5' overhangs containing suitable restriction sites. The introduction of said restriction sites at the 5' and 3' ends of the DNA fragment allows ligation of the restricted PCR product into the digested plasmid pAMA1-MET-PAL. The resulting plasmid, pAMA1-MET-PAL-C4H, contains the genes encoding PAL and C4H that are each under the control of an individual pgdA promoter from Aspergillus nidulans. The sequence of the genes encoding PAL and C4H is verified by sequencing of two different clones of pAMA1-MET-PAL-C4H.

Example 28

Construction of a Fungal Vector for Expression of TAL in Species Belonging to the Genus Aspergillus The gene encoding for TAL, isolated as described in example 1, is reamplified by PCR from the plasmid pESC-URA-TAL (example 6) using forward- and reverse primers, with 5' overhangs containing suitable restriction sites. The introduction of said restriction sites at the 5' and 3' ends of the gene allows ligation of the restricted PCR product into a digested pAMA1-MET vector. The resulting plasmid, pAMA1-MET-TAL, contains the gene encoding for TAL under the control of the gpdA promoter from Aspergillus nidulans. The sequence of the gene encoding for TAL is verified by sequencing of two different clones of pAMA1-MET-TAL.

Example 29

Construction of a Fungal Vector for Expression of 4CL and VST in species belonging to the genus Aspergillus The gene encoding 4CL, isolated as described in example 1, is reamplified by PCR from the plasmid pESC-TRP-4CL-VST (example 5), using forward- and reverse primers, with 5' overhangs containing suitable restriction sites. The introduction of said restriction sites at the 5' and 3' ends of the gene allows ligation of the restricted PCR product into a digested pAMA1-HIS vector that contains the gpdA promoter from Aspergillus nidulans. The resulting plasmid, pAMA1-HIS-4CL contains the gene encoding 4CL under the control of the gpdA promoter from Aspergillus nidulans.

The gene encoding VST, isolated as described in example 1, is reamplified by PCR from the plasmid pESC-TRP-4CL-VST (example 5) using forward- and reverse primers, with 5' overhangs containing suitable restriction sites. The introduction of said restriction sites at the 5' and 3' ends of the gene allows ligation of the restricted PCR product into a digested pAMA1-MET vector to yield pAMA1-MET-VST. The gpdA promoter and the gene encoding VST are reamplified as one fragment by PCR from the plasmid pAMA1-MET-VST using forward- and reverse primers, with 5' overhangs containing suitable restriction sites. The introduction of said restriction sites at the 5' and 3' ends of the DNA fragment allows ligation of the restricted PCR product into the digested plasmid pAMA1-HIS-4CL. The resulting plasmid, pAMA1-HIS-4CL-VST, contains the genes encoding 4CL and VST that are each under the control of an individual pgdA promoter from Aspergillus nidulans. The sequence of the genes encoding 4CL and VST is verified by sequencing of two different clones of pAMA1-HIS-4CL-VST.

Example 30

Expression of the Pathway to Resveratrol in *Aspergillus niger*

*Aspergillus niger* strains are transformed with the vectors described in examples 27, 28 and 29, separately or in combination. The transformation of the fungal cell is conducted in accordance with methods known in the art, for instance, by electroporation or by conjugation (see, e.g., Sambrook et al., 1989). Transformants are selected on minimal medium lacking methionine and/or histidine.

A strain of *Aspergilus niger* that is auxotrophic for histidine and methionine, for instance, strain FGSC A919 (see www.fgsc DOT net)("." replaced with "DOT" to inactivate URL), is transformed separately with the vector pAMA1-MET-TAL (example 28), yielding the strain FSAN-TAL; with pAMA1-MET-PAL-C4H (example 27), yielding the strain FSAN-PALC4H and with pAMA1-HIS-4CL-VST (example 29), yielding strain FSAN-4CLVST. In addition, *Aspergillus niger* strain FGSC A919 is co-transformed with pAMA1-MET-TAL (example 28) and pAMA1-HIS-4CL-VST (example 29), and the transformed strain is named FSAN-TAL4CLVST. The same strain is also co-transformed with pAMA1-MET-PAL-C4H (example 27), and pAMA1-HIS-4CL-VST (example 29), resulting in the strain FSAN-PALC4H4CLVST.

Example 31

Expression of the Pathway to Resveratrol in *Aspergillus oryzae*

A strain of *Aspergillus oryzae* that contains a native set of genes encoding for PAL, C4H and 4CL (Seshime et al., 2005) and that is auxotrophic for methionine, is transformed with the vector pAMA1-MET-VST (example 29), yielding the strain FSAO-VST. The transformation of the fungal cell is conducted in accordance with methods known in the art, for instance, by electroporation or by conjugation (see, e.g., Sambrook et al., 1989). Transformants are selected on minimal medium lacking methionine.

Example 32

Fermentation with Recombinant Strains of *Aspergillus niger* and *Aspergillus oryzae* in Fermentors The recombinant yeast strains can be grown in fermenters operated as batch, fed-batch or chemostat cultures.

Batch and Fed-Batch Cultivations

The microorganism is grown in a baffled bioreactor with a working volume of 1.5 liters under aerobic conditions. All cultures are incubated at 30° C., at 500 rpm. A constant pH of 6.0 is maintained by automatic addition of 10 M KOH, and aerobic conditions are obtained by sparging the bioreactor with air at a rate of 1 vvm to ensure that the DOT is more than 80%. Cells are grown on glucose in defined medium consisting of the following components to allow growth in batch cultivations: 7.3 g/l $(NH_4)_2SO_4$, 1.5 g/l $KH_2PO_4$, 1.0 g/l $MgSO_4.7H_2O$, 1.0 g/l NaCl, 0.1 g/l $CaCl_2.2H_2O$, 0.1 ml/l Sigma antifoam, 7.2 mg/l $ZnSO_4.7H_2O$, 1.3 mg/l $CuSO_4.5H_2O$, 0.3 mg/l $NiCl_2.6H_2O$, 3.5 mg/l $MnCl_2.4H_2O$ and 6.9 mg/l $FeSO_4.7H_2O$. The glucose concentration is, for example, 10-20-, 30-, 40- or 50 g/l. To allow growth in fed-batch cultivations the medium is composed of: 7.3 g/l $(NH_4)_2SO_4$, 4.0 g/l $KH_2PO_4$, 1.9 g/l $MgSO_4.7H_2O$, 1.3 g/l NaCl, 0.10 g/l $CaCl_2.2H_2O$, 0.1 ml/l Sigma antifoam, 7.2 mg/l $ZnSO_4.7H_2O$, 1.3 mg/l $CuSO_4.5H_2O$, 0.3 mg/l $NiCl_2.6H_2O$, 3.5 mg/l $MnCl_2.4H_2O$ and 6.9 mg/l $FeSO_4.H_2O$ in the batch phase. The reactor is then fed with, for example, 285 g/kg glucose and 42 g/kg $(NH_4)_2SO_4$.

Free mycelium from a pre-batch is used for inoculating the batch- and fed-batch cultures. A spore concentration of $2.10^9$ spores/l is used for inoculation of the pre-batch culture at pH 2.5. Spores are obtained by propagation of freeze-dried spores onto 29 g rice to which the following components are added: 6 ml 15 g/l sucrose, 2.3 g/l $(NH_4)_2SO_4$, 1.0 g/l $KH_2PO_4$, 0.5 g/l $MgSO_4.7H_2O$, 0.50 g/l NaCl, 14.3 mg/l $ZnSO_4.7H_2O$, 2.5 mg/$CuSO_4.5H_2O$, 0.50 mg/l $NiCl_2.6H_2O$, and 13.8 mg/l $FeSO_4.7H_2O$. The spores are propagated at 30° C. for 7-14 days to yield a black layer of spores on the rice grains and are harvested by adding 100 ml of 0.1% Tween 20 in sterile water. For all conditions, the gas is sterile filtered before being introduced into the bioreactor. The off gas is led through a condenser cooled to lower than −8° C. and analyzed for its volumetric content of $CO_2$ and $O_2$ by means of an acoustic gas analyser.

Chemostat Cultures

In chemostat cultures the cells can be grown in, for example, 1.5-L working-volume Biostat B laboratory fermentors at 30° C. and 500 rpm. A constant pH of 6.0 is maintained by automatic addition of 10 M KOH, and aerobic conditions are obtained by sparging the bioreactor with air at a rate of 1 vvm to ensure that the DOT is more than 80%. The dilution rate (D) can be set at different values, e.g. at 0.050 $h^{-1}$, 0.10 $h^{-1}$, 0.15 $h^{-1}$, or 0.20 $h^{-1}$. The pH is kept constant, e.g at 6.6, by automatic addition of 10 M KOH, using a minimal growth medium with the following components: 2.5 g/l $(NH_4)_2SO_4$, 0.75 g/l $KH_2PO_4$, 1.0 g/l $MgSO_4.7H_2O$, 1.0 g/l NaCl, 0.1 g/l $CaCl_2.2H_2O$, 0.1 ml/l Sigma antifoam, 7.2 mg/l $ZnSO_4.7H_2O$, 1.3 mg/l $CuSO_4.5H_2O$, 0.3 mg/l $NiCl_2.6H_2O$, 3.5 mg/l $MnCl_2.4H_2O$ and 6.9 mg/l $FeSO_4.7H_2O$. The concentration of glucose can be set at different values, e.g. is 3.0 g/l 6.0 g/l, 12.0 g/l, 15.0 g/l or 18.0 g/l. The bioreactor is inoculated with free mycelium from a pre-batch culture as described above, and the feed pump is turned on at the end of the exponential growth phase.

For all conditions, the gas is sterile filtered before being introduced into the bioreactor. The off gas is led through a condenser cooled to lower than −8° C. and analyzed for its volumetric content of $CO_2$ and $O_2$ by means of an acoustic gas analyser.

Cultivations are considered to be in steady state after at least 5 residence times, and if the concentrations of biomass glucose and composition of the off-gas remain unchanged (less than 5% relative deviation) over the last two residence times.

Example 33

Extraction and Analysis of Resveratrol in *Aspergillus niger* and *Aspergillus oryzae*

Extraction and analysis is performed using the methods as described in examples 14 and 15.

References

U.S. Pat. No. 6,521,748

Patent no. US-A-2001053847

Patent no. US-A-2004059103

Patent no. US-A-2004023357

Allina, S. M., Pri-Hadash, A., Theilmann, D. A., Ellis, B. E. and Douglas, C. J. (1998) 4-coumarate: Coenzyme A ligase in hybrid poplar. Properties of enzymes, cDNA cloning, and analysis of recombinant clones. Plant Physiol. 116, 743-754.

Aoyama, Y., Yoshida, Y., Kubota, S., Kumaoka, H. and Furumichi, A. (1978). NADPH-cytochrome P-450 reductase of yeast microsomes. Arch. Biochem. Biophys. 185, 362-369.

Becker J V, Armstrong G O, van der Merwe M J, Lambrechts M G, Vivier M A, Pretorius I S. (2003). Metabolic engineering of *Saccharomyces cerevisiae* for the synthesis of the wine-related antioxidant resveratrol. FEMS Yeast Res. 4, 79-85.

Blanquet, S., Meunier, J. P., Minekus, M., Marol-Bonnin, S., and Alric, M. (2003). Recombinant *Saccharomyces cerevisiae* Expressing P450 in Artificial Digestive Systems: a Model for Biodetoxication in the Human Digestive Environment. Appl. Environ. Microbiol. 69, 2884-2892.

Celotti E and others. (1996). Resveratrol content of some wines obtained from dried Valpolicella grapes: Recioto and Amarone. Journal of Chromatography A 730, 47-52.

Cochrane, F. C., Davin, L. B. and Lewis N. G. (2004). The *Arabidopsis* phenylalanine ammonia lyase gene family: kinetic characterization of the four PAL isoforms. Phytochemistry 65, 1557-1564.

Couzin, J. (2004) Aging Research's Family Feud. Science 303, 1276-1279.

Ehlting, J., Büttner, D., Wang, Q., Douglas, C. J., Somssich, I. E. and Kombrink, E. (1999). Three 4-coumarate:coenzyme A ligases in *Arabidopsis thaliana* represents two evolutionary divergent classes in angiosperms. The plant journal. 19, 9-20.

Filpula, D., Vaslet, C. A., Levy, A., Sykes, A. and Strausberg, R. L. Nucleotide sequence of gene for phenylalanine ammonia-lyase from *Rhodotorula rubra*. (1988). Nucleic Acids Res. 16, 11381.

Gehm, B. D., McAndrews, J. M., Chien, P. Y. and Jameson, J. L. (1997). Resveratrol, a polyphenolic compound found in grapes and wine, is an agonist for the estrogen receptor. Proc. Natl. Acad. Sci. USA 94, 14138-14143.

Gems, D., Johnstone, I. L. and Clutterbuck, A. J. (1991). An autonomously replicating plasmid transforms *Aspergillus nidulans* at high frequency. Gene 98, 61-67.

Hain, R., Reif, H. J., Krause, E., Langebartels, R., Kindl, H., Vornam, B., Wiese, W., Schmelzer, E., Schreier, P. H., Stocker, R. H. and Stenzel, K. (1993). Disease resistance results from foreign phytoalexin expression in a novel plant. Nature 361, 153-156.

Hwang E I, Kaneko M, Ohnishi Y, Horinouchi S. (2003). Production of plant-specific flavanones by *Escherichia coli* containing an artificial gene cluster. Appl. Environ. Microbiol. 69, 2699-706.

Huang, M-T. (1997). Diet for cancer prevention. Food Sci. 24, 713-727

Hart, J. H. (1981) Annu. Rev. Phytopathology 19, 437-458.

Hart, J. H., Shrimpton, D. M. (1979) Phytopathology 69, 1138-1143.

Hall, S. S. (2003) In Vino Vitalis? Compounds Activate Life-Extending Genes. Science 301, 1165.

Hamberger, B. and Hahlbrock, K. (2004). The 4-coumarate: CoA ligase gene family in *Arabidopsis thaliana* comprises one rare, sinapate-activating and three commonly occurring isoenzymes. Proc. Natl. Acad. Sci. USA. 101, 2209-2214.

Jang, M., Cai, L., Udeani, G O., Slowing, K V., Thomas, C F., Beecher, C W W., Fong, H H S., Farnsworth, N R., Kinghorn, A D., Mehta, R G., Moon, R C., Pezzuto, J M. (1997). Cancer Chemopreventive Activity of Resveratrol, a Natural Product Derived from Grapes. Science 275, 218-220.

Jeandet, P. Bessis, R., Maume, B. F., Meunier, P., Peyron, D. and Trollat, P. (1995). Effect of Enological Practices on the Resveratrol Isomer Content of Wine J. Agric. Food Chem. 43, 316-319.

Jeandet, P. Bessis, R., Sbaghi, M. and Meunier, P. (1994). Occurence of a resveratrol β-D-glucoside in wine: Preliminary studies. Vitis 33, 183-184.

Koopmann, E., Logemann, E. and Hahlbrock, K. (1999). Regulation and Functional Expression of Cinnamate 4-Hydroxylase from Parsley. Plant Physiol. 119, 49-55.

Kopp, P. (1998). Resveratrol, a phytooestrogen found in red wine. A possible explanation for the conundrum of the "French Paradox"? Eur. J. Endocrinol. 138, 619-620.

Kyndt J A, Meyer T E, Cusanovich M A, Van Beeumen J J. (2002). Characterization of a bacterial tyrosine ammonia lyase, a biosynthetic enzyme for the photoactive yellow protein. FEBS Lett. 512, 240-244.

LaGrange, D. C., Pretorius, I. S. and Van Zyl, W. H. (1997). Cloning of the *Bacillus pumilus* beta-xylosidase gene (xynB) and its expression in *Saccharomyces cerevisiae*. Appl. Microbiol. Biotechnol. 47, 262-266.

Lin X., Kaul S., Rounsley S. D., Shea T. P., Benito M.-I., Town C. D., Fujii C. Y., Mason T. M., Bowman C. L., Barnstead M. E., Feldblyum T. V., Buell C. R., Ketchum K. A., Lee J. J., Ronning C. M., Koo H. L., Moffat K. S., Cronin L. A., Shen M., Pai G., Van Aken S., Umayam L., Tallon L. J., Gill J. E., Adams M. D., Carrera A. J., Creasy T. H., Goodman H. M., Somerville C. R., Copenhaver G. P., Preuss D., Nierman W. C., White O., Eisen J. A., Salzberg S. L., Fraser C. M., Venter J. C. (1999). Sequence and analysis of chromosome 2 of the plant *Arabidopsis thaliana*. Nature 402, 761-768.

Lobo, R. A. (1995). Benefits and risks of estrogen replacement therapy. Am. J. Obstet. Gynecol. 173, 982-989.

Martin, V. J. J., Pitera, D. J., Withers, S. T., Newman, J. D. and Keasling, J. D. (2003). Engineering a mevalonate pathway in *Escherichia coli* for production of terpenoids. Nature biotechnology 21, 796-802.

Mizutani, M., Ohta, D. and Sato, R. (1997). Isolation of a cDNA and a genomic clone encoding cinnamate 4-hydroxylase from *Arabidopsis* and its expression manner in planta. Plant Physiol. 113, 755-763.

Ro, D. K., Mah, N., Ellis, B. E. and Douglas, C. J. (2001). Functional Characterization and Subcellular Localization of Poplar (*Populus trichocarpa*×*Populus deltoides*) Cinnamate 4-Hydroxylase. Plant Physiol. 126, 317-329.

Ro D. K., Douglas C. J. (2004). Reconstitution of the entry point of plant phenylpropanoid metabolism in yeast (*Saccharomyces cerevisiae*): implications for control of metabolic flux into the phenylpropanoid pathway. J. Biol. Chem. 279, 2600-2607.

Rosler J, Krekel F, Amrhein N, Schmid J. (1997). Maize phenylalanine ammonia-lyase has tyrosine ammonia-lyase activity. Plant Physiol. 113, 175-179. activity. Plant physiol. 113, 175-179.

Samappito, S., Page, J. E., Schmidt, J., De-Eknamkul, W. and Kutchan, T. M. (2003). Aromatic and pyrone polyketides synthesized by a stilbene synthase from *Rheum tataricum*. Phytochemistry 62, 313-323.

Sambrook, J., Fritsch, E. F. and Maniatis, T. (1989). Molecular Cloning, A Laboratory Manual, 2d edition, Cold Spring Harbor, N.Y.

Schoppner, A.; Kindl, H. (1984) Purification and properties of a stilbene synthase from induced cell suspension cultures of peanut. J. Biol. Chem. 259, 6806-6811.

Seshime, Y., Juvvadi, P. R., Fujii, I. and Kitamoto, K. (2005). Genomic evidences for the existence of a phenylpropanoid metabolic pathway in *Aspergillus oryzae*. Biochem Biophys Res Commun. 337, 747-51.

Urban P., Mignotte, C., Kazmaier M., Delorme F. And Pompon D. (1997). Cloning, Yeast Expression, and Characterization of the Coupling of Two Distantly Related *Arabidopsis thaliana* NADPH-Cytochrome 450 Reductases with P450 CYP73A5. J. Biol. Chem. 272, 19176-19186.

Watts, K. T., Lee, P. C. and Schmidt-Dannert, C. (2004). Exploring recombinant flavonoid biosynthesis in metabolically engineered *Escherichia coli*. Chembiochem 5, 500-507.

The following is a summary of the nucleotide and amino acid sequences appearing herein:

SEQ ID NO: 1 is a nucleotide sequence from *Arabidopsis thaliana* encoding a phenylalanine ammonia lyase (PAL2).
SEQ ID NO: 2 is the amino acid sequence encoded by SEQ ID NO: 1.
SEQ ID NO: 3 is a nucleotide sequence from *Arabidopsis thaliana* encoding a cinnamate 4-hydroxylase (C4H).
SEQ ID NO: 4 is the amino acid sequence encoded by SEQ ID NO: 3.
SEQ ID NO: 5 is a nucleotide sequence from *Arabidopsis thaliana* encoding a 4-coumarate:CoenzymeA ligase (4CL1).
SEQ ID NO: 6 is the amino acid sequence encoded by SEQ ID NO: 5.
SEQ ID NO: 7 is a nucleotide sequence from *Rheum tataricum* encoding a resveratrol synthase (VST).
SEQ ID NO: 8 is the amino acid sequence encoded by SEQ ID NO: 7.
SEQ ID NO: 9 is a nucleotide sequence from *Rheum tataricum* encoding a resveratrol synthase (VST), which is codon-optimized for expression in *S. cerevisiae*.
SEQ ID NO: 10 is the amino acid sequence encoded by SEQ ID NO: 9.
SEQ ID NO: 11 is a nucleotide sequence from *Rhodobacter capsulatus* encoding a tyrosine ammonia lyase (TAL).
SEQ ID NO: 12 is the amino acid sequence encoded by SEQ ID NO: 11.
SEQ ID NO: 13 is a nucleotide sequence from *Rhodobacter capsulatus* encoding a tyrosine ammonia lyase (TAL), which is codon-optimized for expression in *S. cerevisiae*.
SEQ ID NO: 14 is the amino acid sequence encoded by SEQ ID NO: 13.
SEQ ID NO: 15 is a nucleotide sequence from *S. cerevisiae* encoding a NADPH:cytochrome P450 reductase (CPR1).
SEQ ID NO: 16 is the amino acid sequence encoded by SEQ ID NO: 15.
SEQ ID NO: 17 is a nucleotide sequence from *Arabidopsis thalianus* encoding a NADPH:cytochrome P450 reductase (AR2).
SEQ ID NO: 18 is the amino acid sequence encoded by SEQ ID NO: 17.
SEQ ID NOs 19-32 are primer sequences appearing in Table 1, Example 1.
SEQ ID NOs 33-34 are primer sequences appearing in Example 16.
SEQ ID NOs 35-38 are primer sequences appearing in Example 17

The invention claimed is:

1. An isolated or non-naturally occurring micro-organism, wherein the micro-organism has an engineered operative metabolic pathway producing resveratrol, or an oligomeric or glycosidically-bound derivative thereof, wherein the engineered operative metabolic pathway produces:
   a) 4-coumaric acid from L-phenylalanine catalysed by a phenylalanine ammonia lyase and a cinnamate 4-hydroxylase expressed in the micro-organism or from tyrosine catalysed by a phenylalanine ammonia lyase or a tyrosine ammonia lyase expressed in said micro-organism; and
   b) 4-coumaroyl-CoA from 4-coumaric acid catalysed by a 4-coumarate-CoA ligase expressed in said micro-organism;
   wherein the micro-organism is cultured in a media with a carbon substrate and does not require an external source of phenylalanine, tyrosine, cinnamic acid or coumaric acid, and resveratrol is produced from the 4-coumaroyl-CoA by a resveratrol synthase expressed in the micro-organism.

2. The micro-organism as claimed in claim 1, wherein said resveratrol is produced in a reaction catalysed by an enzyme in which endogenous malonyl-CoA is a substrate.

3. The micro-organism as claimed in claim 1, wherein said resveratrol synthase is expressed in said micro-organism from a nucleic acid coding for said enzyme which is not native to the micro-organism.

4. The micro-organism as claimed in claim 1, wherein said cinnamate 4-hydroxylase is expressed in said micro-organism from a nucleic acid coding for said enzyme which is not native to the micro-organism.

5. The micro-organism as claimed in claim 1, wherein said phenylalanine ammonia lyase is expressed in said micro-organism from a nucleic acid coding for said enzyme which is not native to the micro-organism.

6. The micro-organism as claimed in claim 1, wherein a native NADPH:cytochrome P450 reductase (CPR) is overexpressed in said micro-organism or wherein the micro-organism comprises a recombinant CPR.

7. The micro-organism as claimed in claim 1, wherein at least one copy of a genetic sequence encoding the tyrosine ammonia lyase is operatively linked to an expression signal not natively associated with said genetic sequence in said organism.

8. The micro-organism as claimed in claim 1, wherein at least one copy of a genetic sequence encoding the phenylalanine ammonia lyase is operatively linked to an expression signal not natively associated with said genetic sequence in said organism.

9. The micro-organism as claimed in claim 1, wherein at least one copy of a genetic sequence encoding the cinnamate 4-hydroxylase is operatively linked to an expression signal not natively associated with said genetic sequence in said organism.

10. The micro-organism as claimed in claim 1, wherein at least one copy of a genetic sequence encoding the 4-coumarate-CoA ligase is operatively linked to an expression signal not natively associated with said genetic sequence in said organism.

11. The micro-organism as claimed in claim 1, wherein at least one copy of a genetic sequence encoding the resveratrol synthase is operatively linked to an expression signal not natively associated with said genetic sequence in said organism.

12. The micro-organism as claimed in claim 1, containing one or more copies of an heterologous DNA sequence encoding phenylalanine ammonia lyase operatively associated with an expression signal, and containing one or more copies of an heterologous DNA sequence encoding cinnamate-4-hydroxylase operatively associated with an expression signal, and containing one or more copies of an heterologous DNA sequence encoding 4-coumarate CoA-ligase operatively associated with an expression signal, and containing one or more copies of an heterologous DNA sequence encoding resveratrol synthase operatively associated with an expression signal.

13. The micro-organism as claimed in claim 1, lacking cinnamate-4-hydroxylase activity, and containing one or more copies of a heterologous DNA sequence encoding tyrosine ammonia lyase operatively associated with an expression signal, and containing one or more copies of an heterologous DNA sequence encoding 4-coumarate CoA-ligase operatively associated with an expression signal, and containing one or more copies of an heterologous DNA sequence encoding resveratrol synthase operatively associated with an expression signal.

14. The micro-organism of claim 1, comprising expressible nucleotide sequences encoding, and said micro-organism is capable of producing, phenylalanine or tyrosine ammonia lyase, cinnamate 4-hydroxylase, 4-coumarate-CoA ligase and resveratrol synthase.

15. The micro-organism of claim 1, wherein said 4-coumaric acid is produced from trans-cinnamic acid by cinnamate 4-hydroxylase, or said 4-coumaric acid is produced from tyrosine by phenylalanine ammonia lyase or tyrosine ammonia lyase, and 4-coumaroyl-CoA is formed in a reaction catalysed by an enzyme in which ATP and CoA are substrates and ADP is a product catalysed by 4-coumarate-CoA ligase.

16. The microorganism of claim 1 which is a bacterium.

17. The microorganism of claim 16 which is a bacterium belonging to a genus selected from the group consisting of *Bacillus, Escherichia, Lactobacillus, Lactococcus, Corynebacterium, Acetobacter, Acinetobacter,* and *Pseudomonas*.

18. The microorganism of claim 16 which is an *Escherichia coli*.

19. The microorganism of claim 1 which is a yeast belonging to a genus selected from the group consisting of *Saccharomyces, Kluyveromyces, Pichia, Debaromyces, Hansenula, Pichia, Zygosaccharomyces* and *Schizosaccharomyces*.

20. The microorganism of claim 1 which is a yeast belonging to the genus *Saccharomyces*.

21. The microorganism of claim 1 which is a *Saccharomyces cerevisiae*.

22. The microorganism of claim 1 which is a filamentous fungus belonging to a genus selected from the group consisting of *Rhizopus, Fusidium, Gibberella*, and *Trichoderma*.

23. The microorganism of claim 1, wherein the microorganism is capable of producing 0.44-0.53 µg of resveratrol per gram dry weight.

* * * * *